(12) United States Patent
Hariton et al.

(10) Patent No.: US 12,611,305 B2
(45) Date of Patent: Apr. 28, 2026

(54) MINIMALLY-INVASIVE DELIVERY SYSTEMS

(71) Applicant: CARDIOVALVE LTD., Or Yehuda (IL)

(72) Inventors: Ilia Hariton, Zichron Yaakov (IL);
Boaz Harari, Ganey Tikva (IL);
Maxim Karalnik, Karmiel (IL);
Michael Albitov, Kiryat Ono (IL);
Meni Iamberger, Kfar Saba (IL)

(73) Assignee: CARDIOVALVE LTD., Or Yehuda (IL)

( * ) Notice: Subject to any disclaimer, the term of this patent is extended or adjusted under 35 U.S.C. 154(b) by 120 days.

(21) Appl. No.: 18/765,724

(22) Filed: Jul. 8, 2024

(65) Prior Publication Data

US 2024/0423796 A1 Dec. 26, 2024

Related U.S. Application Data

(63) Continuation of application No. 17/181,722, filed on Feb. 22, 2021, now Pat. No. 12,053,379, which is a (Continued)

(30) Foreign Application Priority Data

Aug. 1, 2016 (GB) ...................................... 1613219

(51) Int. Cl.
*A61F 2/24* (2006.01)
*A61F 2/966* (2013.01)
*A61F 2/958* (2013.01)

(52) U.S. Cl.
CPC .......... *A61F 2/2436* (2013.01); *A61F 2/2433* (2013.01); *A61F 2/966* (2013.01); *A61F 2002/9583* (2013.01)

(58) Field of Classification Search
CPC ............................. A61F 2/2436; A61F 2/2496
See application file for complete search history.

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CA 2822801 8/2006
CA 2671966 6/2008
(Continued)

OTHER PUBLICATIONS

An Office Action dated Nov. 23, 2012, which issued during the prosecution of U.S. Appl. No. No. 13/033,852.
(Continued)

*Primary Examiner* — Alexander J Orkin
(74) *Attorney, Agent, or Firm* — Sughrue Mion, PLLC

(57) ABSTRACT

A method includes delivering an implant to a heart of a patient using a delivery tool that includes a nosepiece that is fixed to a shaft and distal to an implant, and an expandable element proximal to the nosepiece. Maximally-expanded, the expandable element (i) has an expanded external diameter at its widest part that is smaller than the expanded internal diameter of a lumen of the frame of the implant and (ii) tapers proximally away from the widest part and from the nosepiece. In a compressed state of the implant a portion of the expandable element is disposed within the lumen of the frame. The method includes, following implantation of the implant, withdrawing the expandable element proximally through the lumen of the implant, between leaflets of the implant, and out of the lumen. Other applications are also described.

17 Claims, 16 Drawing Sheets

Related U.S. Application Data continuation of application No. 16/318,025, filed as application No. PCT/IL2017/050849 on Aug. 1, 2017, now Pat. No. 10,952,850.

(56) References Cited

U.S. PATENT DOCUMENTS

| | | |
|---|---|---|
| 3,840,018 A | 10/1974 | Heifetz |
| 3,874,388 A | 4/1975 | King et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,222,126 A | 9/1980 | Boretos et al. |
| 4,261,342 A | 4/1981 | Aranguren |
| 4,275,469 A | 6/1981 | Gabbay |
| 4,340,091 A | 7/1982 | Skelton et al. |
| 4,423,525 A | 1/1984 | Vallana et al. |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,853,986 A | 8/1989 | Allen |
| 4,892,541 A | 1/1990 | Alonso |
| 4,917,698 A | 4/1990 | Carpenter et al. |
| 4,961,738 A | 10/1990 | Mackin |
| 4,972,494 A | 11/1990 | White et al. |
| 4,994,077 A | 2/1991 | Dobben |
| 5,061,277 A | 10/1991 | Carpentier et al. |
| 5,078,739 A | 1/1992 | Martin |
| 5,089,006 A | 2/1992 | Stiles |
| 5,104,407 A | 4/1992 | Lam et al. |
| 5,108,420 A | 4/1992 | Marks |
| 5,201,757 A | 4/1993 | Heyn et al. |
| 5,201,880 A | 4/1993 | Wright |
| 5,258,008 A | 11/1993 | Wilk |
| 5,275,622 A | 1/1994 | Lazarus et al. |
| 5,300,034 A | 4/1994 | Behnke |
| 5,306,296 A | 4/1994 | Wright et al. |
| 5,314,473 A | 5/1994 | Godin |
| 5,325,845 A | 7/1994 | Adair |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,450,860 A | 9/1995 | O'Connor |
| 5,473,812 A | 12/1995 | Morris et al. |
| 5,477,856 A | 12/1995 | Lundquist |
| 5,593,424 A | 1/1997 | Northrup, III |
| 5,601,572 A | 2/1997 | Middleman et al. |
| 5,607,444 A | 3/1997 | Lam |
| 5,607,470 A | 3/1997 | Milo |
| 5,626,609 A | 5/1997 | Zvenyatsky et al. |
| 5,647,857 A | 7/1997 | Anderson et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,713,948 A | 2/1998 | Uflacker |
| 5,716,370 A | 2/1998 | Williamson et al. |
| 5,716,397 A | 2/1998 | Myers |
| 5,716,417 A | 2/1998 | Girard et al. |
| 5,728,116 A | 3/1998 | Rosenman |
| 5,730,150 A | 3/1998 | Peppel et al. |
| 5,741,297 A | 4/1998 | Simon |
| 5,749,371 A | 5/1998 | Zadini et al. |
| 5,749,920 A | 5/1998 | Quiachon et al. |
| 5,765,682 A | 6/1998 | Bley et al. |
| 5,766,151 A | 6/1998 | Valley et al. |
| 5,776,140 A | 7/1998 | Cottone |
| 5,810,882 A | 9/1998 | Bolduc |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,868,777 A | 2/1999 | Lam |
| 5,873,906 A | 2/1999 | Lau et al. |
| 5,876,373 A | 3/1999 | Giba et al. |
| 5,906,619 A | 5/1999 | Olson et al. |
| 5,935,098 A | 8/1999 | Blaisdell et al. |
| 5,954,766 A | 9/1999 | Zadno-Azizi et al. |
| 5,957,949 A | 9/1999 | Leonhardt et al. |
| 5,957,953 A | 9/1999 | DiPoto et al. |
| 5,961,440 A | 10/1999 | Schweich et al. |
| 5,961,539 A | 10/1999 | Northrup, III et al. |
| 5,961,549 A | 10/1999 | Nguyen et al. |
| 5,980,565 A | 11/1999 | Jayaraman |
| 5,984,959 A | 11/1999 | Robertson |
| 6,010,530 A | 1/2000 | Goicoechea |
| 6,019,787 A | 2/2000 | Richard et al. |
| 6,042,554 A | 3/2000 | Rosenman |
| 6,042,607 A | 3/2000 | Williamson, IV |
| 6,045,497 A | 4/2000 | Schweich et al. |
| 6,050,936 A | 4/2000 | Schweich et al. |
| 6,059,715 A | 5/2000 | Schweich et al. |
| 6,059,827 A | 5/2000 | Fenton |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern |
| 6,110,200 A | 8/2000 | Hinnenkamp |
| 6,113,612 A | 9/2000 | Swanson et al. |
| 6,120,534 A | 9/2000 | Ruiz |
| 6,126,686 A | 10/2000 | Badylak et al. |
| 6,143,024 A | 11/2000 | Campbell et al. |
| 6,152,937 A | 11/2000 | Peterson et al. |
| 6,159,240 A | 12/2000 | Sparer |
| 6,165,119 A | 12/2000 | Schweich et al. |
| 6,165,183 A | 12/2000 | Kuehn et al. |
| 6,165,210 A | 12/2000 | Lau et al. |
| 6,174,332 B1 | 1/2001 | Loch |
| 6,183,411 B1 | 2/2001 | Mortier et al. |
| 6,187,020 B1 | 2/2001 | Zegdi et al. |
| 6,187,040 B1 | 2/2001 | Wright |
| 6,193,686 B1 | 2/2001 | Estrada et al. |
| 6,193,745 B1 | 2/2001 | Fogarty et al. |
| 6,217,610 B1 | 4/2001 | Carpentier et al. |
| 6,221,102 B1 | 4/2001 | Baker et al. |
| 6,231,602 B1 | 5/2001 | Carpentier et al. |
| 6,251,092 B1 | 6/2001 | Qin et al. |
| 6,254,609 B1 | 7/2001 | Vrba et al. |
| 6,264,700 B1 | 7/2001 | Kilcoyne et al. |
| 6,271,278 B1 | 8/2001 | Park et al. |
| 6,287,339 B1 | 9/2001 | Vasquez et al. |
| 6,296,656 B1 | 10/2001 | Bodluc et al. |
| 6,312,465 B1 | 11/2001 | Griffin et al. |
| 6,315,784 B1 | 11/2001 | Djurovic |
| 6,319,281 B1 | 11/2001 | Patel |
| 6,332,893 B1 | 12/2001 | Mortier et al. |
| 6,334,873 B1 | 1/2002 | Lane et al. |
| 6,346,074 B1 | 2/2002 | Roth |
| 6,350,278 B1 | 2/2002 | Lenker et al. |
| 6,352,561 B1 | 3/2002 | Leopold et al. |
| 6,391,036 B1 | 5/2002 | Berg et al. |
| 6,398,758 B1 | 6/2002 | Jacobsen et al. |
| 6,402,780 B2 | 6/2002 | Williamson, IV |
| 6,406,420 B1 | 6/2002 | McCarthy et al. |
| 6,406,493 B1 | 6/2002 | Tu et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,451,054 B1 | 9/2002 | Stevens |
| 6,454,799 B1 | 9/2002 | Schreck |
| 6,458,153 B1 | 10/2002 | Bailey et al. |
| 6,461,366 B1 | 10/2002 | Seguin |
| 6,470,892 B1 | 10/2002 | Forsell |
| 6,478,807 B1 | 11/2002 | Foreman et al. |
| 6,482,228 B1 | 11/2002 | Norred |
| 6,491,711 B1 | 12/2002 | Durcan |
| 6,503,274 B1 | 1/2003 | Howanec et al. |

(56) References Cited

U.S. PATENT DOCUMENTS

| | | | |
|---|---|---|---|
| 6,511,491 B2 | 1/2003 | Grudem et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,540,782 B1 | 4/2003 | Snyders |
| 6,547,801 B1 | 4/2003 | Dargent et al. |
| 6,551,350 B1 | 4/2003 | Thornton et al. |
| 6,554,845 B1 | 4/2003 | Fleenor et al. |
| 6,558,396 B1 | 5/2003 | Inoue |
| 6,558,418 B2 | 5/2003 | Carpentier et al. |
| 6,564,805 B2 | 5/2003 | Garrison et al. |
| 6,565,603 B2 | 5/2003 | Cox |
| 6,569,196 B1 | 5/2003 | Vesely |
| 6,569,198 B1 | 5/2003 | Wilson et al. |
| 6,579,297 B2 | 6/2003 | Bicek et al. |
| 6,582,464 B2 | 6/2003 | Gabbay |
| 6,589,160 B2 | 7/2003 | Schweich et al. |
| 6,602,263 B1 | 8/2003 | Swanson et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,616,675 B1 | 9/2003 | Evard et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. et al. |
| 6,629,921 B1 | 10/2003 | Schweich et al. |
| 6,651,671 B1 | 11/2003 | Donlon et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,699,256 B1 | 3/2004 | Logan et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,456 B2 | 3/2004 | Langberg et al. |
| 6,711,444 B2 | 3/2004 | Koblish |
| 6,712,836 B1 | 3/2004 | Berg et al. |
| 6,716,244 B2 | 4/2004 | Klaco |
| 6,718,985 B2 | 4/2004 | Hlavka et al. |
| 6,719,781 B1 | 4/2004 | Kim |
| 6,719,786 B2 | 4/2004 | Ryan et al. |
| 6,719,788 B2 | 4/2004 | Cox |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,749,630 B2 | 6/2004 | McCarthy et al. |
| 6,752,813 B2 | 6/2004 | Goldfarb et al. |
| 6,755,857 B2 | 6/2004 | Peterson et al. |
| 6,764,310 B1 | 7/2004 | Ichihashi et al. |
| 6,764,510 B2 | 7/2004 | Vidlund et al. |
| 6,764,514 B1 | 7/2004 | Li et al. |
| 6,764,518 B2 | 7/2004 | Godin |
| 6,767,362 B2 | 7/2004 | Schreck |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,821,297 B2 | 11/2004 | Snyders |
| 6,830,585 B1 | 12/2004 | Artof et al. |
| 6,830,638 B2 | 12/2004 | Boylan et al. |
| 6,849,084 B2 | 2/2005 | Rabkin et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,884,257 B1 | 4/2005 | Cox |
| 6,893,459 B1 | 5/2005 | Macoviak |
| 6,893,460 B1 | 5/2005 | Spenser et al. |
| 6,908,482 B2 | 6/2005 | McCarthy et al. |
| 6,918,917 B1 | 7/2005 | Nguyen et al. |
| 6,926,715 B1 | 8/2005 | Hauck et al. |
| 6,926,730 B1 | 8/2005 | Nguyen et al. |
| 6,939,370 B2 | 9/2005 | Hartley et al. |
| 6,951,571 B1 | 10/2005 | Srivastava |
| 6,960,217 B2 | 11/2005 | Bolduc |
| 6,964,684 B2 | 11/2005 | Ortiz et al. |
| 6,964,686 B2 | 11/2005 | Gordon |
| 6,974,476 B2 | 12/2005 | McGuckin et al. |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,918 B2 | 2/2006 | Soltesz et al. |
| 6,997,951 B2 | 2/2006 | Solem et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,041,132 B2 | 5/2006 | Quijano et al. |
| 7,074,236 B2 | 7/2006 | Rabkin et al. |
| 7,077,850 B2 | 7/2006 | Kortenbach |
| 7,077,861 B2 | 7/2006 | Spence |
| 7,077,862 B2 | 7/2006 | Vidlund et al. |
| 7,087,064 B1 | 8/2006 | Hyde |
| 7,101,336 B2 | 9/2006 | Miller |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,137,184 B2 | 11/2006 | Schreck |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,656 B2 | 2/2007 | Khairkhahan |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,252,682 B2 | 8/2007 | Seguin |
| 7,261,686 B2 | 8/2007 | Couvillon, Jr. |
| 7,288,097 B2 | 10/2007 | Seguin |
| 7,288,111 B1 | 10/2007 | Holloway et al. |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,316,716 B2 | 1/2008 | Egan |
| 7,329,279 B2 | 2/2008 | Haug et al. |
| 7,329,280 B2 | 2/2008 | Bolling et al. |
| 7,335,213 B1 | 2/2008 | Hyde et al. |
| 7,351,256 B2 | 4/2008 | Hojeibane et al. |
| 7,361,190 B2 | 4/2008 | Shoulian et al. |
| 7,364,588 B2 | 4/2008 | Mathis et al. |
| 7,374,571 B2 | 5/2008 | Pease et al. |
| 7,374,573 B2 | 5/2008 | Gabbay |

(56)                    References Cited

U.S. PATENT DOCUMENTS

| | | | |
|---|---|---|---|
| 7,377,938 B2 | 5/2008 | Sarac et al. |
| 7,377,941 B2 | 5/2008 | Rhee et al. |
| 7,381,218 B2 | 6/2008 | Schreck |
| 7,381,219 B2 | 6/2008 | Salahieh et al. |
| 7,390,329 B2 | 6/2008 | Westra et al. |
| 7,404,824 B1 | 7/2008 | Webler et al. |
| 7,422,603 B2 | 9/2008 | Lane |
| 7,429,269 B2 | 9/2008 | Schwammenthal |
| 7,431,692 B2 | 10/2008 | Zollinger et al. |
| 7,442,204 B2 | 10/2008 | Schwammenthal |
| 7,442,207 B2 | 10/2008 | Rafiee |
| 7,445,630 B2 | 11/2008 | Lashinski et al. |
| 7,452,376 B2 | 11/2008 | Lim et al. |
| 7,455,677 B2 | 11/2008 | Vargas et al. |
| 7,455,688 B2 | 11/2008 | Furst et al. |
| 7,455,690 B2 | 11/2008 | Cartledge et al. |
| 7,462,162 B2 | 12/2008 | Phan et al. |
| 7,481,838 B2 | 1/2009 | Carpentier et al. |
| 7,485,142 B2 | 2/2009 | Milo |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,527,647 B2 | 5/2009 | Spence |
| 7,530,995 B2 | 5/2009 | Quijano et al. |
| 7,549,983 B2 | 6/2009 | Roue et al. |
| 7,556,632 B2 | 7/2009 | Zadno |
| 7,556,646 B2 | 7/2009 | Yang et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,582,111 B2 | 9/2009 | Krolik et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,597,711 B2 | 10/2009 | Drews et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,611,534 B2 | 11/2009 | Kapadia et al. |
| 7,618,449 B2 | 11/2009 | Tremulis et al. |
| 7,621,948 B2 | 11/2009 | Hermann et al. |
| 7,625,403 B2 | 12/2009 | Krivoruchko |
| 7,632,302 B2 | 12/2009 | Vreeman et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,648,528 B2 | 1/2010 | Styrc |
| 7,655,015 B2 | 2/2010 | Goldfarb et al. |
| 7,666,204 B2 | 2/2010 | Thornton et al. |
| 7,682,319 B2 | 3/2010 | Martin |
| 7,682,369 B2 | 3/2010 | Seguin |
| 7,682,380 B2 | 3/2010 | Thornton et al. |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,708,775 B2 | 5/2010 | Rowe et al. |
| 7,717,951 B2 | 5/2010 | Flagle et al. |
| 7,717,952 B2 | 5/2010 | Case et al. |
| 7,717,955 B2 | 5/2010 | Lane et al. |
| 7,722,666 B2 | 5/2010 | Lafontaine |
| 7,731,741 B2 | 6/2010 | Eidenschink |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,753,922 B2 | 7/2010 | Starksen |
| 7,753,924 B2 | 7/2010 | Starksen et al. |
| 7,753,949 B2 | 7/2010 | Lamphere et al. |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,080 B2 | 8/2010 | Bei et al. |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,296 B2 | 10/2010 | Goldfarb et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,368 B2 | 1/2011 | Zollinger et al. |
| 7,871,432 B2 | 1/2011 | Bergin |
| 7,871,433 B2 | 1/2011 | Lattouf |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,988,725 B2 | 8/2011 | Gross et al. |
| 7,992,567 B2 | 8/2011 | Hirotsuka et al. |
| 7,993,368 B2 | 8/2011 | Gambale et al. |
| 7,993,392 B2 | 8/2011 | Righini et al. |
| 7,993,393 B2 | 8/2011 | Carpentier et al. |
| 7,993,397 B2 | 8/2011 | Lashinski |
| 8,002,825 B2 | 8/2011 | Letac et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,103 B2 | 10/2011 | Burriesci |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,592 B2 | 11/2011 | Goldfarb et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,070,805 B2 | 12/2011 | Vidlund |
| 8,075,611 B2 | 12/2011 | Milwee et al. |

(56)  References Cited

U.S. PATENT DOCUMENTS

| | | | |
|---|---|---|---|
| 8,075,616 | B2 | 12/2011 | Solem |
| 8,080,054 | B2 | 12/2011 | Rowe |
| 8,083,793 | B2 | 12/2011 | Lane et al. |
| D652,927 | S | 1/2012 | Braido et al. |
| D653,341 | S | 1/2012 | Braido et al. |
| 8,092,518 | B2 | 1/2012 | Schreck |
| 8,092,520 | B2 | 1/2012 | Quadri |
| 8,092,521 | B2 | 1/2012 | Figulla et al. |
| 8,100,964 | B2 | 1/2012 | Spence |
| 8,105,377 | B2 | 1/2012 | Liddicoat |
| 8,109,996 | B2 | 2/2012 | Stacchino et al. |
| 8,118,866 | B2 | 2/2012 | Herrmann et al. |
| 8,123,800 | B2 | 2/2012 | McCarthy |
| 8,123,801 | B2 | 2/2012 | Milo |
| 8,133,270 | B2 | 3/2012 | Kheradvar et al. |
| 8,136,218 | B2 | 3/2012 | Millwee et al. |
| 8,137,398 | B2 | 3/2012 | Tuval et al. |
| 8,142,492 | B2 | 3/2012 | Forster et al. |
| 8,142,493 | B2 | 3/2012 | Spence et al. |
| 8,142,494 | B2 | 3/2012 | Rahdert et al. |
| 8,142,495 | B2 | 3/2012 | Hasenkam et al. |
| 8,142,496 | B2 | 3/2012 | Berreklouw |
| 8,142,497 | B2 | 3/2012 | Friedman |
| 8,147,504 | B2 | 4/2012 | Ino et al. |
| 8,147,542 | B2 | 4/2012 | Maisano et al. |
| 8,152,844 | B2 | 4/2012 | Rao |
| 8,157,852 | B2 | 4/2012 | Bloom et al. |
| 8,157,853 | B2 | 4/2012 | Laske et al. |
| 8,157,860 | B2 | 4/2012 | McNamara et al. |
| 8,163,008 | B2 | 4/2012 | Wilson et al. |
| 8,163,013 | B2 | 4/2012 | Machold et al. |
| 8,163,014 | B2 | 4/2012 | Lane et al. |
| D660,433 | S | 5/2012 | Braido et al. |
| D660,967 | S | 5/2012 | Braido et al. |
| 8,167,894 | B2 | 5/2012 | Miles et al. |
| 8,167,932 | B2 | 5/2012 | Bourang et al. |
| 8,167,935 | B2 | 5/2012 | McGuckin, Jr. et al. |
| 8,172,896 | B2 | 5/2012 | McNamara et al. |
| 8,172,898 | B2 | 5/2012 | Alferness et al. |
| 8,177,836 | B2 | 5/2012 | Lee et al. |
| 8,182,528 | B2 | 5/2012 | Salahieh et al. |
| 8,187,299 | B2 | 5/2012 | Goldfarb et al. |
| 8,187,324 | B2 | 5/2012 | Webler et al. |
| 8,202,315 | B2 | 6/2012 | Hlavka et al. |
| 8,206,439 | B2 | 6/2012 | Gomez-Duran |
| 8,211,169 | B2 | 7/2012 | Lane et al. |
| 8,216,256 | B2 | 7/2012 | Raschdorf, Jr. et al. |
| 8,216,301 | B2 | 7/2012 | Bonhoeffer et al. |
| 8,221,492 | B2 | 7/2012 | Case et al. |
| 8,221,493 | B2 | 7/2012 | Boyle et al. |
| 8,226,710 | B2 | 7/2012 | Nguyen et al. |
| 8,226,711 | B2 | 7/2012 | Mortier et al. |
| 8,231,670 | B2 | 7/2012 | Salahieh et al. |
| 8,231,671 | B2 | 7/2012 | Kim |
| 8,235,933 | B2 | 8/2012 | Keren et al. |
| 8,236,045 | B2 | 8/2012 | Benichou et al. |
| 8,236,049 | B2 | 8/2012 | Rowe et al. |
| 8,241,351 | B2 | 8/2012 | Cabiri |
| 8,252,042 | B2 | 8/2012 | McNamara et al. |
| 8,252,050 | B2 | 8/2012 | Maisano et al. |
| 8,252,051 | B2 | 8/2012 | Chau et al. |
| 8,252,052 | B2 | 8/2012 | Salahieh et al. |
| 8,257,390 | B2 | 9/2012 | Carley et al. |
| 8,262,725 | B2 | 9/2012 | Subramanian |
| 8,267,988 | B2 | 9/2012 | Hamer et al. |
| 8,277,501 | B2 | 10/2012 | Chalekian et al. |
| 8,277,502 | B2 | 10/2012 | Miller et al. |
| 8,287,584 | B2 | 10/2012 | Salahieh et al. |
| 8,287,591 | B2 | 10/2012 | Keidar et al. |
| 8,298,280 | B2 | 10/2012 | Yadin et al. |
| 8,303,608 | B2 | 11/2012 | Goldfarb et al. |
| 8,303,653 | B2 | 11/2012 | Bonhoeffer et al. |
| 8,308,798 | B2 | 11/2012 | Pintor et al. |
| 8,313,525 | B2 | 11/2012 | Tuval et al. |
| 8,317,853 | B2 | 11/2012 | Agnew |
| 8,317,855 | B2 | 11/2012 | Gregorich et al. |
| 8,323,334 | B2 | 12/2012 | Deem et al. |
| 8,323,335 | B2 | 12/2012 | Rowe et al. |
| 8,328,868 | B2 | 12/2012 | Paul et al. |
| 8,333,777 | B2 | 12/2012 | Schaller et al. |
| 8,337,541 | B2 | 12/2012 | Quadri et al. |
| 8,343,173 | B2 | 1/2013 | Starksen et al. |
| 8,343,174 | B2 | 1/2013 | Goldfarb et al. |
| 8,343,213 | B2 | 1/2013 | Salahieh et al. |
| 8,348,999 | B2 | 1/2013 | Kheradvar et al. |
| 8,349,002 | B2 | 1/2013 | Milo |
| 8,353,956 | B2 | 1/2013 | Miller et al. |
| 8,357,195 | B2 | 1/2013 | Kuehn |
| 8,361,144 | B2 | 1/2013 | Fish et al. |
| 8,366,767 | B2 | 2/2013 | Zhang |
| 8,372,140 | B2 | 2/2013 | Hoffman et al. |
| 8,377,119 | B2 | 2/2013 | Drews et al. |
| 8,382,829 | B1 | 2/2013 | Call et al. |
| 8,388,680 | B2 | 3/2013 | Starksen et al. |
| 8,393,517 | B2 | 3/2013 | Milo |
| 8,398,708 | B2 | 3/2013 | Meiri et al. |
| 8,403,981 | B2 | 3/2013 | Forster et al. |
| 8,403,983 | B2 | 3/2013 | Quadri et al. |
| 8,408,214 | B2 | 4/2013 | Spenser |
| 8,414,644 | B2 | 4/2013 | Quadri et al. |
| 8,425,593 | B2 | 4/2013 | Braido et al. |
| 8,430,926 | B2 | 4/2013 | Kirson |
| 8,430,934 | B2 | 4/2013 | Das |
| 8,444,689 | B2 | 5/2013 | Zhang |
| 8,449,599 | B2 | 5/2013 | Chau et al. |
| 8,449,625 | B2 | 5/2013 | Campbell et al. |
| 8,454,686 | B2 | 6/2013 | Alkhatib |
| 8,460,365 | B2 | 6/2013 | Haverkost et al. |
| 8,460,370 | B2 | 6/2013 | Zakay et al. |
| 8,460,371 | B2 | 6/2013 | Hlavka et al. |
| 8,460,372 | B2 | 6/2013 | Mcnamara et al. |
| 8,474,460 | B2 | 7/2013 | Barrett et al. |
| 8,475,491 | B2 | 7/2013 | Milo |
| 8,480,732 | B2 | 7/2013 | Subramanian |
| 8,500,800 | B2 | 8/2013 | Maisano et al. |
| 8,500,821 | B2 | 8/2013 | Sobrino-Serrano et al. |
| 8,512,400 | B2 | 8/2013 | Tran et al. |
| 8,518,107 | B2 | 8/2013 | Tsukashima et al. |
| 8,523,881 | B2 | 9/2013 | Cabiri et al. |
| 8,523,940 | B2 | 9/2013 | Richardson et al. |
| 8,529,431 | B2 | 9/2013 | Baker et al. |
| 8,539,662 | B2 | 9/2013 | Stacchino et al. |
| 8,540,767 | B2 | 9/2013 | Zhang |
| 8,545,544 | B2 | 10/2013 | Spenser et al. |
| 8,545,553 | B2 | 10/2013 | Zipory et al. |
| 8,551,160 | B2 | 10/2013 | Figulla et al. |
| 8,551,161 | B2 | 10/2013 | Dolan |
| 8,562,672 | B2 | 10/2013 | Bonhoeffer et al. |
| 8,568,475 | B2 | 10/2013 | Nguyen et al. |
| 8,579,964 | B2 | 11/2013 | Lane et al. |
| 8,579,965 | B2 | 11/2013 | Bonhoeffer et al. |
| 8,585,755 | B2 | 11/2013 | Chau et al. |
| 8,585,756 | B2 | 11/2013 | Bonhoeffer et al. |
| 8,591,460 | B2 | 11/2013 | Wilson et al. |
| 8,591,570 | B2 | 11/2013 | Revuelta et al. |
| 8,591,576 | B2 | 11/2013 | Hasenkam et al. |
| 8,608,797 | B2 | 12/2013 | Gross et al. |
| 8,623,075 | B2 | 1/2014 | Murray et al. |
| 8,623,080 | B2 | 1/2014 | Fogarty et al. |
| 8,628,569 | B2 | 1/2014 | Benichou et al. |
| 8,628,570 | B2 | 1/2014 | Seguin |
| 8,628,571 | B1 | 1/2014 | Hacohen et al. |
| 8,641,727 | B2 | 2/2014 | Starksen et al. |
| 8,652,202 | B2 | 2/2014 | Alon et al. |
| 8,652,203 | B2 | 2/2014 | Quadri et al. |
| 8,652,204 | B2 | 2/2014 | Quill et al. |
| 8,657,872 | B2 | 2/2014 | Seguin |
| 8,663,322 | B2 | 3/2014 | Keranen |
| 8,673,020 | B2 | 3/2014 | Sobrino-Serrano et al. |
| 8,679,174 | B2 | 3/2014 | Ottma et al. |
| 8,685,086 | B2 | 4/2014 | Navia et al. |
| 8,690,939 | B2 | 4/2014 | Miller et al. |
| 8,696,611 | B2 | 4/2014 | Nitzan et al. |
| 8,696,742 | B2 | 4/2014 | Pintor et al. |

(56)          References Cited

U.S. PATENT DOCUMENTS

| | | | |
|---|---|---|---|
| 8,715,342 | B2 | 5/2014 | Zipory et al. |
| 8,728,097 | B1 | 5/2014 | Sugimoto et al. |
| 8,728,155 | B2 | 5/2014 | Montorfano et al. |
| 8,734,467 | B2 | 5/2014 | Miller et al. |
| 8,734,507 | B2 | 5/2014 | Keranen |
| 8,740,920 | B2 | 6/2014 | Goldfarb et al. |
| 8,740,962 | B2 | 6/2014 | Finch et al. |
| 8,747,460 | B2 | 6/2014 | Tuval et al. |
| 8,771,345 | B2 | 7/2014 | Tuval et al. |
| 8,778,021 | B2 | 7/2014 | Cartledge |
| 8,784,472 | B2 | 7/2014 | Eidenschink |
| 8,784,479 | B2 | 7/2014 | Antonsson et al. |
| 8,784,481 | B2 | 7/2014 | Alkhatib et al. |
| 8,790,367 | B2 | 7/2014 | Nguyen et al. |
| 8,790,394 | B2 | 7/2014 | Miller et al. |
| 8,795,298 | B2 | 8/2014 | Hernlund et al. |
| 8,795,355 | B2 | 8/2014 | Alkhatib |
| 8,795,356 | B2 | 8/2014 | Quadri et al. |
| 8,795,357 | B2 | 8/2014 | Yohanan et al. |
| 8,801,776 | B2 | 8/2014 | House et al. |
| 8,808,366 | B2 | 8/2014 | Braido et al. |
| 8,808,368 | B2 | 8/2014 | Maisano et al. |
| 8,808,371 | B2 | 8/2014 | Cartledge |
| 8,834,551 | B2 | 9/2014 | Mcguckin, Jr. |
| 8,840,663 | B2 | 9/2014 | Salahieh et al. |
| 8,840,664 | B2 | 9/2014 | Karapetian et al. |
| 8,845,717 | B2 | 9/2014 | Khairkhahan et al. |
| 8,845,722 | B2 | 9/2014 | Gabbay |
| 8,845,723 | B2 | 9/2014 | Spence et al. |
| 8,852,261 | B2 | 10/2014 | White |
| 8,852,272 | B2 | 10/2014 | Gross et al. |
| 8,858,623 | B2 | 10/2014 | Miller et al. |
| 8,864,822 | B2 | 10/2014 | Spence et al. |
| 8,870,948 | B1 | 10/2014 | Erzberger et al. |
| 8,870,949 | B2 | 10/2014 | Rowe |
| 8,870,950 | B2 | 10/2014 | Hacohen |
| 8,876,800 | B2 | 11/2014 | Behan |
| 8,888,843 | B2 | 11/2014 | Khairkhahan et al. |
| 8,894,702 | B2 | 11/2014 | Quadri et al. |
| 8,900,294 | B2 | 12/2014 | Paniagua et al. |
| 8,900,295 | B2 | 12/2014 | Migliazza et al. |
| 8,906,083 | B2 | 12/2014 | Obermiller et al. |
| 8,911,455 | B2 | 12/2014 | Quadri et al. |
| 8,911,461 | B2 | 12/2014 | Traynor et al. |
| 8,911,489 | B2 | 12/2014 | Ben-Muvhar |
| 8,911,493 | B2 | 12/2014 | Rowe et al. |
| 8,911,494 | B2 | 12/2014 | Hammer et al. |
| 8,926,695 | B2 | 1/2015 | Gross et al. |
| 8,926,696 | B2 | 1/2015 | Cabiri et al. |
| 8,926,697 | B2 | 1/2015 | Gross et al. |
| 8,932,343 | B2 | 1/2015 | Alkhatib et al. |
| 8,932,348 | B2 | 1/2015 | Solem et al. |
| 8,940,042 | B2 | 1/2015 | Miller et al. |
| 8,940,044 | B2 | 1/2015 | Hammer et al. |
| 8,945,177 | B2 | 2/2015 | Dell et al. |
| 8,945,211 | B2 | 2/2015 | Sugimoto |
| 8,951,285 | B2 | 2/2015 | Sugimoto et al. |
| 8,951,286 | B2 | 2/2015 | Sugimoto et al. |
| 8,961,595 | B2 | 2/2015 | Alkhatib |
| 8,979,922 | B2 | 3/2015 | Jayasinghe et al. |
| 8,986,370 | B2 | 3/2015 | Annest |
| 8,986,373 | B2 | 3/2015 | Chau et al. |
| 8,986,375 | B2 | 3/2015 | Garde et al. |
| 8,992,599 | B2 | 3/2015 | Thubrikar et al. |
| 8,992,604 | B2 | 3/2015 | Gross et al. |
| 8,992,608 | B2 | 3/2015 | Haug et al. |
| 8,998,982 | B2 | 4/2015 | Richter et al. |
| 9,005,155 | B2 | 4/2015 | Sugimoto |
| 9,005,273 | B2 | 4/2015 | Salahieh et al. |
| 9,011,468 | B2 | 4/2015 | Ketai et al. |
| 9,011,520 | B2 | 4/2015 | Miller et al. |
| 9,011,527 | B2 | 4/2015 | Li et al. |
| 9,011,530 | B2 | 4/2015 | Reich et al. |
| 9,017,399 | B2 | 4/2015 | Gross et al. |
| D730,520 | S | 5/2015 | Braido et al. |
| D730,521 | S | 5/2015 | Braido et al. |
| 9,023,100 | B2 | 5/2015 | Quadri et al. |
| 9,034,032 | B2 | 5/2015 | McLean et al. |
| 9,034,033 | B2 | 5/2015 | McLean et al. |
| 9,039,757 | B2 | 5/2015 | McLean et al. |
| D732,666 | S | 6/2015 | Nguyen et al. |
| 9,050,188 | B2 | 6/2015 | Schweich et al. |
| 9,060,858 | B2 | 6/2015 | Thornton et al. |
| 9,072,603 | B2 | 7/2015 | Tuval et al. |
| 9,084,676 | B2 | 7/2015 | Chau et al. |
| 9,095,434 | B2 | 8/2015 | Rowe |
| 9,119,719 | B2 | 9/2015 | Zipory et al. |
| 9,125,632 | B2 | 9/2015 | Loulmet et al. |
| 9,125,738 | B2 | 9/2015 | Figulla et al. |
| 9,125,740 | B2 | 9/2015 | Morriss et al. |
| 9,132,006 | B2 | 9/2015 | Spenser et al. |
| 9,132,009 | B2 | 9/2015 | Hacohen et al. |
| 9,138,312 | B2 | 9/2015 | Tuval et al. |
| 9,155,619 | B2 | 10/2015 | Liu et al. |
| 9,173,646 | B2 | 11/2015 | Fabro |
| 9,173,659 | B2 | 11/2015 | Bodewadt et al. |
| 9,173,738 | B2 | 11/2015 | Murray et al. |
| 9,180,005 | B1 | 11/2015 | Lashinski et al. |
| 9,180,009 | B2 | 11/2015 | Majkrzak et al. |
| 9,192,472 | B2 | 11/2015 | Gross et al. |
| 9,216,076 | B2 | 12/2015 | Mitra et al. |
| 9,220,594 | B2 | 12/2015 | Braido et al. |
| 9,226,820 | B2 | 1/2016 | Braido et al. |
| 9,226,825 | B2 | 1/2016 | Starksen et al. |
| 9,226,839 | B1 | 1/2016 | Kariniemi et al. |
| 9,232,995 | B2 | 1/2016 | Kovalsky et al. |
| 9,241,790 | B2 | 1/2016 | Lane et al. |
| 9,241,791 | B2 | 1/2016 | Braido et al. |
| 9,241,792 | B2 | 1/2016 | Benichou et al. |
| 9,241,794 | B2 | 1/2016 | Braido et al. |
| 9,248,014 | B2 | 2/2016 | Lane et al. |
| 9,265,608 | B2 | 2/2016 | Miller et al. |
| 9,277,994 | B2 | 3/2016 | Miller et al. |
| 9,277,995 | B2 | 3/2016 | Celermajer et al. |
| 9,289,290 | B2 | 3/2016 | Alkhatib et al. |
| 9,289,291 | B2 | 3/2016 | Gorman et al. |
| 9,295,550 | B2 | 3/2016 | Nguyen et al. |
| 9,295,551 | B2 | 3/2016 | Straubinger et al. |
| 9,295,552 | B2 | 3/2016 | McLean et al. |
| 9,301,836 | B2 | 4/2016 | Buchbinder et al. |
| 9,308,087 | B2 | 4/2016 | Lane et al. |
| 9,320,591 | B2 | 4/2016 | Bolduc |
| D755,384 | S | 5/2016 | Pesce et al. |
| 9,326,852 | B2 | 5/2016 | Spenser |
| 9,326,876 | B2 | 5/2016 | Acosta et al. |
| 9,345,573 | B2 | 5/2016 | Nyuli et al. |
| 9,351,830 | B2 | 5/2016 | Gross et al. |
| 9,358,107 | B2 | 6/2016 | Nguyen et al. |
| 9,387,078 | B2 | 7/2016 | Gross et al. |
| 9,393,110 | B2 | 7/2016 | Levi et al. |
| 9,393,111 | B2 | 7/2016 | Ma et al. |
| 9,421,098 | B2 | 8/2016 | Gifford et al. |
| 9,427,303 | B2 | 8/2016 | Liddy et al. |
| 9,427,316 | B2 | 8/2016 | Schweich, Jr. et al. |
| 9,439,757 | B2 | 9/2016 | Wallace et al. |
| 9,445,893 | B2 | 9/2016 | Vaturi |
| 9,463,102 | B2 | 10/2016 | Kelly |
| 9,474,599 | B2 | 10/2016 | Keränen |
| 9,474,638 | B2 | 10/2016 | Robinson et al. |
| 9,480,559 | B2 | 11/2016 | Vidlund et al. |
| 9,492,273 | B2 | 11/2016 | Wallace et al. |
| 9,498,314 | B2 | 11/2016 | Behan |
| 9,498,332 | B2 | 11/2016 | Hacohen et al. |
| 9,510,947 | B2 | 12/2016 | Straubinger et al. |
| 9,532,870 | B2 | 1/2017 | Cooper et al. |
| 9,554,897 | B2 | 1/2017 | Lane et al. |
| 9,554,899 | B2 | 1/2017 | Granada et al. |
| 9,561,103 | B2 | 2/2017 | Granada et al. |
| 9,566,152 | B2 | 2/2017 | Schweich et al. |
| 9,572,665 | B2 | 2/2017 | Lane et al. |
| 9,597,182 | B2 | 3/2017 | Straubinger et al. |
| 9,629,715 | B2 | 4/2017 | Nitzan et al. |
| 9,629,716 | B2 | 4/2017 | Seguin |
| 9,649,480 | B2 | 5/2017 | Sugimoto et al. |

(56) References Cited

U.S. PATENT DOCUMENTS

| | | | |
|---|---|---|---|
| 9,662,203 B2 | 5/2017 | Sheahan et al. |
| 9,681,948 B2 | 6/2017 | Levi et al. |
| 9,681,952 B2 | 6/2017 | Hacohen et al. |
| 9,707,382 B2 | 7/2017 | Nitzan et al. |
| 9,713,696 B2 | 7/2017 | Yacoby et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,901,443 B2 | 2/2018 | Morriss et al. |
| 9,974,651 B2 | 5/2018 | Hariton et al. |
| 9,987,132 B1 | 6/2018 | Hariton et al. |
| 9,993,360 B2 | 6/2018 | Shalev et al. |
| 10,010,414 B2 | 7/2018 | Cooper et al. |
| 10,016,271 B2 | 7/2018 | Morriss et al. |
| 10,039,638 B2 | 8/2018 | Bruchman et al. |
| 10,045,845 B2 | 8/2018 | Hacohen et al. |
| 10,076,415 B1 | 9/2018 | Metchik et al. |
| 10,098,732 B1 | 10/2018 | Hariton et al. |
| 10,105,222 B1 | 10/2018 | Metchik et al. |
| 10,111,751 B1 | 10/2018 | Metchik et al. |
| 10,117,744 B2 | 11/2018 | Ratz et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,206,668 B2 | 2/2019 | Mcgoldrick et al. |
| 10,226,341 B2 | 3/2019 | Gross et al. |
| 10,231,831 B2 | 3/2019 | Hacohen |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,258,471 B2 | 4/2019 | Lutter et al. |
| 10,292,816 B2 | 5/2019 | Raanani et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,350,062 B2 | 7/2019 | Peterson et al. |
| 10,357,360 B2 | 7/2019 | Hariton et al. |
| 10,368,988 B2 | 8/2019 | Jones |
| 10,376,361 B2 | 8/2019 | Gross et al. |
| 10,390,952 B2 | 8/2019 | Hariton et al. |
| 10,426,610 B2 | 10/2019 | Hariton et al. |
| 10,426,614 B2 | 10/2019 | Hariton et al. |
| 10,449,047 B2 | 10/2019 | Hariton et al. |
| 10,456,256 B2 | 10/2019 | Braido et al. |
| 10,463,487 B2 | 11/2019 | Hariton et al. |
| 10,463,488 B2 | 11/2019 | Hariton et al. |
| 10,492,907 B2 | 12/2019 | Duffy |
| 10,492,908 B2 | 12/2019 | Hammer et al. |
| 10,507,105 B2 | 12/2019 | Hariton et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,903 B2 | 1/2020 | Hariton et al. |
| 10,524,910 B2 | 1/2020 | Hammer et al. |
| 10,531,866 B2 | 1/2020 | Hariton et al. |
| 10,531,872 B2 | 1/2020 | Hacohen et al. |
| 10,537,426 B2 | 1/2020 | Iamberger et al. |
| 10,548,726 B2 | 2/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,610,359 B2 | 4/2020 | Hacohen |
| 10,631,871 B2 | 4/2020 | Goldfarb et al. |
| 10,631,982 B2 | 4/2020 | Hammer et al. |
| 10,631,984 B2 | 4/2020 | Nyuli et al. |
| 10,646,342 B1 | 5/2020 | Marr et al. |
| 10,660,751 B2 | 5/2020 | Hacohen |
| 10,667,908 B2 | 6/2020 | Hariton et al. |
| 10,667,912 B2 | 6/2020 | Dixon et al. |
| 10,682,227 B2 | 6/2020 | Hariton et al. |
| 10,695,173 B2 | 6/2020 | Gross et al. |
| 10,695,177 B2 | 6/2020 | Hariton et al. |
| 10,702,380 B2 | 7/2020 | Morriss et al. |
| 10,702,385 B2 | 7/2020 | Hacohen |
| 10,722,354 B2 | 7/2020 | Cohen-tzemach et al. |
| 10,722,360 B2 | 7/2020 | Hariton et al. |
| 10,736,742 B2 | 8/2020 | Hariton et al. |
| 10,758,342 B2 | 9/2020 | Chau et al. |
| 10,758,344 B2 | 9/2020 | Hariton et al. |
| 10,779,939 B2 | 9/2020 | Hariton et al. |
| 10,799,345 B2 | 10/2020 | Hariton et al. |
| 10,813,760 B2 | 10/2020 | Metchik et al. |
| 10,820,998 B2 | 11/2020 | Marr et al. |
| 10,835,377 B2 | 11/2020 | Hacohen et al. |
| 10,842,627 B2 | 11/2020 | Delgado et al. |
| 10,849,748 B2 | 12/2020 | Hariton et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,864,078 B2 | 12/2020 | Hariton et al. |
| 10,874,514 B2 | 12/2020 | Dixon et al. |
| 10,881,511 B2 | 1/2021 | Hariton et al. |
| 10,888,421 B2 | 1/2021 | Hariton et al. |
| 10,888,422 B2 | 1/2021 | Hariton et al. |
| 10,888,425 B2 | 1/2021 | Delgado et al. |
| 10,888,644 B2 | 1/2021 | Ratz et al. |
| 10,905,548 B2 | 2/2021 | Hariton et al. |
| 10,905,549 B2 | 2/2021 | Hariton et al. |
| 10,905,552 B2 | 2/2021 | Dixon et al. |
| 10,905,554 B2 | 2/2021 | Cao |
| 10,918,481 B2 | 2/2021 | Hariton et al. |
| 10,918,483 B2 | 2/2021 | Metchik et al. |
| 10,925,595 B2 | 2/2021 | Hacohen et al. |
| 10,925,732 B2 | 2/2021 | Delgado et al. |
| 10,945,843 B2 | 3/2021 | Delgado et al. |
| 10,945,844 B2 | 3/2021 | McCann et al. |
| 10,952,850 B2 | 3/2021 | Hariton et al. |
| 10,959,846 B2 | 3/2021 | Marr et al. |
| 10,973,636 B2 | 4/2021 | Hariton et al. |
| 10,993,809 B2 | 5/2021 | McCann et al. |
| 11,065,114 B2 | 7/2021 | Raanani et al. |
| 11,065,117 B2 | 7/2021 | Zeng |
| 11,083,582 B2 | 8/2021 | McCann et al. |
| 11,135,059 B2 | 10/2021 | Hammer et al. |
| 11,147,672 B2 | 10/2021 | McCann et al. |
| 11,179,240 B2 | 11/2021 | Delgado et al. |
| 11,246,704 B2 | 2/2022 | Hariton et al. |
| 11,291,545 B2 | 4/2022 | Hacohen |
| 11,291,546 B2 | 4/2022 | Gross et al. |
| 11,291,547 B2 | 4/2022 | Gross et al. |
| 11,291,844 B2 | 4/2022 | Gross |
| 11,298,117 B2 | 4/2022 | Hariton et al. |
| 11,304,804 B2 | 4/2022 | Hariton et al. |
| 11,304,805 B2 | 4/2022 | Hariton et al. |
| 11,304,806 B2 | 4/2022 | Hariton et al. |
| 11,318,014 B2 | 5/2022 | Hariton et al. |
| 11,318,015 B2 | 5/2022 | Hariton et al. |
| 11,337,802 B2 | 5/2022 | Hariton et al. |
| 11,337,803 B2 | 5/2022 | Hariton et al. |
| 11,337,804 B2 | 5/2022 | Hariton et al. |
| 11,382,746 B2 | 7/2022 | Hariton et al. |
| 11,389,297 B2 | 7/2022 | Franklin et al. |
| 11,426,155 B2 | 8/2022 | Hacohen et al. |
| 11,517,429 B2 | 12/2022 | Gross et al. |
| 11,517,436 B2 | 12/2022 | Hacohen |
| 11,534,298 B2 | 12/2022 | Hariton et al. |

(56)                    References Cited

U.S. PATENT DOCUMENTS

| | | |
|---|---|---|
| 11,571,298 B2 | 2/2023 | Hariton et al. |
| 11,779,458 B2 | 10/2023 | Hariton et al. |
| 11,793,633 B2 | 10/2023 | Hariton et al. |
| 11,793,635 B2 | 10/2023 | Hariton et al. |
| 11,793,638 B2 | 10/2023 | Hariton et al. |
| 11,801,135 B2 | 10/2023 | Hariton et al. |
| 12,053,379 B2 | 8/2024 | Hariton et al. |
| 12,090,048 B2 | 9/2024 | Hariton et al. |
| 2001/0002445 A1 | 5/2001 | Vesely |
| 2001/0005787 A1 | 6/2001 | Oz et al. |
| 2001/0021872 A1 | 9/2001 | Bailey et al. |
| 2001/0021874 A1 | 9/2001 | Carpentier et al. |
| 2001/0044656 A1 | 11/2001 | Williamson et al. |
| 2001/0056295 A1 | 12/2001 | Solem |
| 2002/0013571 A1 | 1/2002 | Goldfarb et al. |
| 2002/0022862 A1 | 2/2002 | Grafton et al. |
| 2002/0029080 A1 | 3/2002 | Mortier et al. |
| 2002/0032481 A1 | 3/2002 | Gabbay |
| 2002/0042621 A1 | 4/2002 | Liddicoat et al. |
| 2002/0082525 A1 | 6/2002 | Oslund et al. |
| 2002/0087048 A1 | 7/2002 | Brock et al. |
| 2002/0099436 A1 | 7/2002 | Thornton et al. |
| 2002/0103532 A1 | 8/2002 | Langberg et al. |
| 2002/0151916 A1 | 10/2002 | Muramatsu et al. |
| 2002/0151961 A1 | 10/2002 | Lashinski et al. |
| 2002/0151970 A1 | 10/2002 | Garrison et al. |
| 2002/0169358 A1 | 11/2002 | Mortier et al. |
| 2002/0173841 A1 | 11/2002 | Ortiz et al. |
| 2002/0177894 A1 | 11/2002 | Acosta et al. |
| 2002/0177904 A1 | 11/2002 | Huxel et al. |
| 2002/0198586 A1 | 12/2002 | Inoue |
| 2003/0009236 A1 | 1/2003 | Godin |
| 2003/0018358 A1 | 1/2003 | Saadat |
| 2003/0036791 A1 | 2/2003 | Philipp et al. |
| 2003/0050693 A1 | 3/2003 | Quijano et al. |
| 2003/0050694 A1 | 3/2003 | Yang et al. |
| 2003/0060846 A1 | 3/2003 | Egnelov et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0074059 A1 | 4/2003 | Nguyen et al. |
| 2003/0078465 A1 | 4/2003 | Pai et al. |
| 2003/0078653 A1 | 4/2003 | Vesely et al. |
| 2003/0083742 A1 | 5/2003 | Spence et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidlund et al. |
| 2003/0158578 A1 | 8/2003 | Pantages et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0010272 A1 | 1/2004 | Manetakis et al. |
| 2004/0019377 A1 | 1/2004 | Taylor et al. |
| 2004/0024451 A1 | 2/2004 | Johnson et al. |
| 2004/0030382 A1 | 2/2004 | St. Goar et al. |
| 2004/0039414 A1 | 2/2004 | Carley et al. |
| 2004/0039436 A1 | 2/2004 | Spenser et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0093060 A1 | 5/2004 | Seguin et al. |
| 2004/0122448 A1 | 6/2004 | Levine |
| 2004/0122503 A1 | 6/2004 | Campbell et al. |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133267 A1 | 7/2004 | Lane |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0143315 A1 | 7/2004 | Bruun et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka et al. |
| 2004/0176788 A1 | 9/2004 | Opolski |
| 2004/0176839 A1 | 9/2004 | Huynh et al. |
| 2004/0181287 A1 | 9/2004 | Gellman |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0236419 A1 | 11/2004 | Milo |
| 2004/0249433 A1 | 12/2004 | Freitag |
| 2004/0249453 A1 | 12/2004 | Cartledge et al. |
| 2004/0260317 A1 | 12/2004 | Bloom et al. |
| 2004/0260389 A1 | 12/2004 | Case et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0021056 A1 | 1/2005 | St. Goar et al. |
| 2005/0027305 A1 | 2/2005 | Shiu et al. |
| 2005/0027348 A1 | 2/2005 | Case et al. |
| 2005/0038494 A1 | 2/2005 | Eidenschink |
| 2005/0055038 A1 | 3/2005 | Kelleher et al. |
| 2005/0055086 A1 | 3/2005 | Stobie |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075726 A1 | 4/2005 | Svanidze et al. |
| 2005/0075727 A1 | 4/2005 | Wheatley |
| 2005/0075731 A1 | 4/2005 | Artof et al. |
| 2005/0080430 A1 | 4/2005 | Wright et al. |
| 2005/0080474 A1 | 4/2005 | Andreas et al. |
| 2005/0085900 A1 | 4/2005 | Case et al. |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137681 A1 | 6/2005 | Shoemaker et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137695 A1 | 6/2005 | Salahieh et al. |
| 2005/0137697 A1 | 6/2005 | Salahieh et al. |
| 2005/0137699 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0182483 A1 | 8/2005 | Osborne et al. |
| 2005/0182486 A1 | 8/2005 | Gabbay |
| 2005/0187613 A1 | 8/2005 | Bolduc et al. |

(56)                    References Cited

U.S. PATENT DOCUMENTS

| | | |
|---|---|---|
| 2005/0192596 A1 | 9/2005 | Jugenheimer et al. |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0203618 A1 | 9/2005 | Sharkawy et al. |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256532 A1 | 11/2005 | Nayak et al. |
| 2005/0256566 A1 | 11/2005 | Gabbay |
| 2005/0267478 A1 | 12/2005 | Corradi et al. |
| 2005/0267573 A9 | 12/2005 | Macoviak et al. |
| 2005/0273138 A1 | 12/2005 | To et al. |
| 2005/0288776 A1 | 12/2005 | Shaoulian et al. |
| 2005/0288778 A1 | 12/2005 | Shaoulian et al. |
| 2005/0288781 A1 | 12/2005 | Moaddeb et al. |
| 2006/0004439 A1 | 1/2006 | Spenser et al. |
| 2006/0004442 A1 | 1/2006 | Spenser et al. |
| 2006/0004443 A1 | 1/2006 | Liddicoat et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041189 A1 | 2/2006 | Vancaillie |
| 2006/0041319 A1 | 2/2006 | Taylor et al. |
| 2006/0047297 A1 | 3/2006 | Case |
| 2006/0052867 A1 | 3/2006 | Revuelta et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0089627 A1 | 4/2006 | Burnett et al. |
| 2006/0095009 A1 | 5/2006 | Lampropoulos et al. |
| 2006/0106423 A1 | 5/2006 | Weisel et al. |
| 2006/0111773 A1 | 5/2006 | Rittgers et al. |
| 2006/0116750 A1 | 6/2006 | Herbert et al. |
| 2006/0116757 A1 | 6/2006 | Lashinski et al. |
| 2006/0122692 A1 | 6/2006 | Gilad et al. |
| 2006/0129166 A1 | 6/2006 | Lavelle |
| 2006/0135964 A1 | 6/2006 | Vesley |
| 2006/0149280 A1 | 7/2006 | Harvine et al. |
| 2006/0149360 A1 | 7/2006 | Schwammenthal et al. |
| 2006/0149368 A1 | 7/2006 | Spence |
| 2006/0155357 A1 | 7/2006 | Melsheimer |
| 2006/0161250 A1 | 7/2006 | Shaw |
| 2006/0161265 A1 | 7/2006 | Levine et al. |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0184240 A1 | 8/2006 | Jimenez et al. |
| 2006/0184242 A1 | 8/2006 | Lichtenstein |
| 2006/0190036 A1 | 8/2006 | Wendel et al. |
| 2006/0190038 A1 | 8/2006 | Carley et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212107 A1 | 9/2006 | Case et al. |
| 2006/0212111 A1 | 9/2006 | Case et al. |
| 2006/0216404 A1 | 9/2006 | Seyler et al. |
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0247763 A1 | 11/2006 | Slater |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0271175 A1 | 11/2006 | Woolfson |
| 2006/0282150 A1 | 12/2006 | Olson et al. |
| 2006/0282161 A1 | 12/2006 | Huyn et al. |
| 2006/0287661 A1 | 12/2006 | Bolduc et al. |
| 2006/0287716 A1 | 12/2006 | Banbury et al. |
| 2006/0287719 A1 | 12/2006 | Rowe et al. |
| 2007/0001627 A1 | 1/2007 | Lin et al. |
| 2007/0008018 A1 | 1/2007 | Nagashima et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027528 A1 | 2/2007 | Agnew |
| 2007/0027533 A1 | 2/2007 | Douk |
| 2007/0027536 A1 | 2/2007 | Mihaljevic et al. |
| 2007/0027549 A1 | 2/2007 | Godin |
| 2007/0038221 A1 | 2/2007 | Fine et al. |
| 2007/0038293 A1 | 2/2007 | St. et al. |
| 2007/0038295 A1 | 2/2007 | Case et al. |
| 2007/0043435 A1 | 2/2007 | Seguin et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0055340 A1 | 3/2007 | Pryor |
| 2007/0056346 A1 | 3/2007 | Spenser et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0078510 A1 | 4/2007 | Ryan |
| 2007/0080188 A1 | 4/2007 | Spence et al. |
| 2007/0083168 A1 | 4/2007 | Whiting et al. |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198082 A1 | 8/2007 | Kapadia et al. |
| 2007/0198097 A1 | 8/2007 | Zegdi |
| 2007/0208550 A1 | 9/2007 | Cao et al. |
| 2007/0213582 A1 | 9/2007 | Zollinger et al. |
| 2007/0213810 A1 | 9/2007 | Newhauser et al. |
| 2007/0213813 A1 | 9/2007 | Von Segesser et al. |
| 2007/0219558 A1 | 9/2007 | Deutsch |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0233239 A1 | 10/2007 | Navia et al. |
| 2007/0239208 A1 | 10/2007 | Crawford |
| 2007/0239265 A1 | 10/2007 | Birdsall et al. |
| 2007/0239272 A1 | 10/2007 | Navia et al. |
| 2007/0239273 A1 | 10/2007 | Allen |
| 2007/0244546 A1 | 10/2007 | Francis |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |

(56)           References Cited

U.S. PATENT DOCUMENTS

| | | |
|---|---|---|
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004688 A1 | 1/2008 | Spenser et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Mackoviak et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086138 A1 | 4/2008 | Stone et al. |
| 2008/0086164 A1 | 4/2008 | Rowe et al. |
| 2008/0086203 A1 | 4/2008 | Roberts |
| 2008/0086204 A1 | 4/2008 | Rankin |
| 2008/0091257 A1 | 4/2008 | Andreas et al. |
| 2008/0091261 A1 | 4/2008 | Long et al. |
| 2008/0097523 A1 | 4/2008 | Bolduc et al. |
| 2008/0097595 A1 | 4/2008 | Gabbay |
| 2008/0103581 A1 | 5/2008 | Goto |
| 2008/0132989 A1 | 6/2008 | Snow et al. |
| 2008/0140003 A1 | 6/2008 | Bei et al. |
| 2008/0140116 A1 | 6/2008 | Bonutti |
| 2008/0140189 A1 | 6/2008 | Nguyen et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195126 A1 | 8/2008 | Solem |
| 2008/0195200 A1 | 8/2008 | Vidlund et al. |
| 2008/0200980 A1 | 8/2008 | Robin et al. |
| 2008/0208265 A1 | 8/2008 | Frazier et al. |
| 2008/0208328 A1 | 8/2008 | Antocci et al. |
| 2008/0208330 A1 | 8/2008 | Keranen |
| 2008/0208332 A1 | 8/2008 | Lamphere et al. |
| 2008/0221672 A1 | 9/2008 | Lamphere et al. |
| 2008/0234813 A1 | 9/2008 | Heuser |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0294234 A1 | 11/2008 | Hartley et al. |
| 2008/0294248 A1 | 11/2008 | Yang et al. |
| 2008/0300629 A1 | 12/2008 | Surti |
| 2009/0005863 A1 | 1/2009 | Goetz et al. |
| 2009/0036966 A1 | 2/2009 | O'Connor et al. |
| 2009/0043153 A1 | 2/2009 | Zollinger et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082844 A1 | 3/2009 | Zacharias et al. |
| 2009/0088836 A1 | 4/2009 | Bishop et al. |
| 2009/0088837 A1 | 4/2009 | Gillinov et al. |
| 2009/0099554 A1 | 4/2009 | Forster et al. |
| 2009/0099650 A1 | 4/2009 | Bolduc et al. |
| 2009/0099653 A1 | 4/2009 | Suri et al. |
| 2009/0105794 A1 | 4/2009 | Ziarno et al. |
| 2009/0105816 A1 | 4/2009 | Olsen et al. |
| 2009/0112159 A1 | 4/2009 | Slattery et al. |
| 2009/0125098 A1 | 5/2009 | Chuter |
| 2009/0125102 A1 | 5/2009 | Cartledge |
| 2009/0149872 A1 | 6/2009 | Gross et al. |
| 2009/0157175 A1 | 6/2009 | Benichou |
| 2009/0163934 A1 | 6/2009 | Raschdorf, Jr. et al. |
| 2009/0171363 A1 | 7/2009 | Chocron |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0177277 A1 | 7/2009 | Milo |
| 2009/0177278 A1 | 7/2009 | Spence |
| 2009/0192601 A1 | 7/2009 | Rafiee et al. |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0248143 A1 | 10/2009 | Laham |
| 2009/0248148 A1 | 10/2009 | Shaolian et al. |
| 2009/0254103 A1 | 10/2009 | Deustch |
| 2009/0259306 A1 | 10/2009 | Rowe |
| 2009/0259307 A1 | 10/2009 | Gross et al. |
| 2009/0264859 A1 | 10/2009 | Mas |
| 2009/0264994 A1 | 10/2009 | Saadat |
| 2009/0264995 A1 | 10/2009 | Subramanian |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0287304 A1 | 11/2009 | Dahlgren et al. |
| 2009/0299409 A1 | 12/2009 | Coe et al. |
| 2009/0299449 A1 | 12/2009 | Styrc |
| 2009/0306768 A1 | 12/2009 | Quardi |
| 2009/0319037 A1 | 12/2009 | Rowe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0022823 A1 | 1/2010 | Goldfarb et al. |
| 2010/0023117 A1 | 1/2010 | Yoganathan et al. |
| 2010/0023118 A1 | 1/2010 | Medlock et al. |
| 2010/0023120 A1 | 1/2010 | Holecek et al. |
| 2010/0030014 A1 | 2/2010 | Ferrazzi |
| 2010/0036479 A1 | 2/2010 | Hill et al. |
| 2010/0036484 A1 | 2/2010 | Hariton et al. |
| 2010/0042147 A1 | 2/2010 | Janovsky et al. |
| 2010/0049306 A1 | 2/2010 | House et al. |
| 2010/0049313 A1 | 2/2010 | Alon et al. |
| 2010/0063542 A1 | 3/2010 | Van Der Burg et al. |
| 2010/0063550 A1 | 3/2010 | Felix et al. |
| 2010/0063586 A1 | 3/2010 | Hasenkam et al. |
| 2010/0069852 A1 | 3/2010 | Kelley |
| 2010/0076499 A1 | 3/2010 | McNamara et al. |
| 2010/0076548 A1 | 3/2010 | Konno |
| 2010/0082094 A1 | 4/2010 | Quadri et al. |
| 2010/0094248 A1 | 4/2010 | Nguyen et al. |
| 2010/0100167 A1 | 4/2010 | Bortlein et al. |
| 2010/0114180 A1 | 5/2010 | Rock |
| 2010/0114299 A1 | 5/2010 | Ben-Muvhar et al. |
| 2010/0121349 A1 | 5/2010 | Meier |
| 2010/0130992 A1 | 5/2010 | Machold et al. |
| 2010/0131054 A1 | 5/2010 | Tuval et al. |
| 2010/0137979 A1 | 6/2010 | Tuval et al. |
| 2010/0152845 A1 | 6/2010 | Bloom et al. |
| 2010/0160958 A1 | 6/2010 | Clark |
| 2010/0161036 A1 | 6/2010 | Pintor et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |

(56) References Cited

U.S. PATENT DOCUMENTS

| | | |
|---|---|---|
| 2010/0174358 A1 | 7/2010 | Rabkin et al. |
| 2010/0174363 A1 | 7/2010 | Castro |
| 2010/0179574 A1 | 7/2010 | Longoria et al. |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0185277 A1 | 7/2010 | Braido et al. |
| 2010/0198347 A1 | 8/2010 | Zakay et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234935 A1 | 9/2010 | Bashiri et al. |
| 2010/0234940 A1 | 9/2010 | Dolan |
| 2010/0249908 A1 | 9/2010 | Chau et al. |
| 2010/0249915 A1 | 9/2010 | Zhang |
| 2010/0249917 A1 | 9/2010 | Zhang |
| 2010/0249920 A1 | 9/2010 | Bolling et al. |
| 2010/0256737 A1 | 10/2010 | Pollock et al. |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0280606 A1 | 11/2010 | Naor |
| 2010/0286628 A1 | 11/2010 | Gross |
| 2010/0286767 A1 | 11/2010 | Zipory et al. |
| 2010/0305475 A1 | 12/2010 | Hinchliffe et al. |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004210 A1 | 1/2011 | Johnson et al. |
| 2011/0004227 A1 | 1/2011 | Goldfarb et al. |
| 2011/0004296 A1 | 1/2011 | Lutter et al. |
| 2011/0004298 A1 | 1/2011 | Lee et al. |
| 2011/0004299 A1 | 1/2011 | Navia et al. |
| 2011/0011917 A1 | 1/2011 | Loulmet |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0026208 A1 | 2/2011 | Otsuro et al. |
| 2011/0029066 A1 | 2/2011 | Gilad et al. |
| 2011/0029067 A1 | 2/2011 | Mcguckin, Jr. et al. |
| 2011/0029072 A1 | 2/2011 | Gabbay |
| 2011/0035000 A1 | 2/2011 | Nieminen et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066231 A1 | 3/2011 | Cartledge et al. |
| 2011/0066233 A1 | 3/2011 | Thornton et al. |
| 2011/0067770 A1 | 3/2011 | Pederson et al. |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087146 A1 | 4/2011 | Ryan et al. |
| 2011/0087322 A1 | 4/2011 | Letac et al. |
| 2011/0093002 A1 | 4/2011 | Rucker et al. |
| 2011/0093063 A1 | 4/2011 | Schreck |
| 2011/0098525 A1 | 4/2011 | Kermode et al. |
| 2011/0098802 A1 | 4/2011 | Braido et al. |
| 2011/0098805 A1 | 4/2011 | Dwork et al. |
| 2011/0106245 A1 | 5/2011 | Miller et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0113768 A1 | 5/2011 | Bauer et al. |
| 2011/0118830 A1 | 5/2011 | Liddicoat et al. |
| 2011/0118832 A1 | 5/2011 | Punjabi |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144703 A1 | 6/2011 | Krause et al. |
| 2011/0144742 A1 | 6/2011 | Madrid et al. |
| 2011/0166636 A1 | 7/2011 | Rowe |
| 2011/0166649 A1 | 7/2011 | Gross et al. |
| 2011/0172784 A1 | 7/2011 | Richter |
| 2011/0178597 A9 | 7/2011 | Navia et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0202130 A1 | 8/2011 | Cartledge et al. |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0230941 A1 | 9/2011 | Markus |
| 2011/0230961 A1 | 9/2011 | Langer et al. |
| 2011/0238088 A1 | 9/2011 | Bodluc et al. |
| 2011/0238094 A1 | 9/2011 | Thomas et al. |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Weimeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257433 A1 | 10/2011 | Walker |
| 2011/0257633 A1 | 10/2011 | Cartledge et al. |
| 2011/0257721 A1 | 10/2011 | Tabor |
| 2011/0257728 A1 | 10/2011 | Kuehn |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0276062 A1 | 11/2011 | Bolduc |
| 2011/0276128 A1 | 11/2011 | Cao et al. |
| 2011/0282361 A1 | 11/2011 | Miller et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288435 A1 | 11/2011 | Christy et al. |
| 2011/0288632 A1 | 11/2011 | White |
| 2011/0288634 A1 | 11/2011 | Tuval et al. |
| 2011/0288635 A1 | 11/2011 | Miller et al. |
| 2011/0295354 A1 | 12/2011 | Bueche et al. |
| 2011/0295363 A1 | 12/2011 | Girard et al. |
| 2011/0301498 A1 | 12/2011 | Maenhout et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319988 A1 | 12/2011 | Schankereli et al. |
| 2011/0319989 A1 | 12/2011 | Lane et al. |

(56) References Cited

U.S. PATENT DOCUMENTS

| | | |
|---|---|---|
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022557 A1 | 1/2012 | Cabiri et al. |
| 2012/0022629 A1 | 1/2012 | Perera et al. |
| 2012/0022633 A1 | 1/2012 | Olson et al. |
| 2012/0022637 A1 | 1/2012 | Ben-Movhar et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035703 A1 | 2/2012 | Lutter et al. |
| 2012/0035712 A1 | 2/2012 | Maisano et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053680 A1 | 3/2012 | Bolling et al. |
| 2012/0053682 A1 | 3/2012 | Kovalsky et al. |
| 2012/0053688 A1 | 3/2012 | Fogarty et al. |
| 2012/0059337 A1 | 3/2012 | Eilat |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078355 A1 | 3/2012 | Zipory et al. |
| 2012/0078357 A1 | 3/2012 | Conklin |
| 2012/0078359 A1 | 3/2012 | Li et al. |
| 2012/0083832 A1 | 4/2012 | Delaloye et al. |
| 2012/0083839 A1 | 4/2012 | Letac et al. |
| 2012/0083874 A1 | 4/2012 | Dale et al. |
| 2012/0083879 A1 | 4/2012 | Eberhardt et al. |
| 2012/0089022 A1 | 4/2012 | House et al. |
| 2012/0089223 A1 | 4/2012 | Nguyen et al. |
| 2012/0095552 A1 | 4/2012 | Spence et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0109155 A1 | 5/2012 | Robinson et al. |
| 2012/0123511 A1 | 5/2012 | Brown |
| 2012/0123529 A1 | 5/2012 | Levi et al. |
| 2012/0123530 A1 | 5/2012 | Carpentier et al. |
| 2012/0123531 A1 | 5/2012 | Tsukashima et al. |
| 2012/0130301 A1 | 5/2012 | McNamara et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0136436 A1 | 5/2012 | Cabiri et al. |
| 2012/0143323 A1 | 6/2012 | Hasenkam et al. |
| 2012/0150218 A1 | 6/2012 | Sandgren et al. |
| 2012/0150290 A1 | 6/2012 | Gabbay |
| 2012/0158021 A1 | 6/2012 | Morrill |
| 2012/0165915 A1 | 6/2012 | Melsheimer et al. |
| 2012/0165930 A1 | 6/2012 | Gifford, III et al. |
| 2012/0179086 A1 | 7/2012 | Shank et al. |
| 2012/0179244 A1 | 7/2012 | Schankereli et al. |
| 2012/0191182 A1 | 7/2012 | Hauser et al. |
| 2012/0197292 A1 | 8/2012 | Chin-Chen et al. |
| 2012/0197388 A1 | 8/2012 | Khairkhahan et al. |
| 2012/0215303 A1 | 8/2012 | Quadri et al. |
| 2012/0239142 A1 | 9/2012 | Liu et al. |
| 2012/0245604 A1 | 9/2012 | Tegzes |
| 2012/0265296 A1 | 10/2012 | McNamara et al. |
| 2012/0271198 A1 | 10/2012 | Whittaker et al. |
| 2012/0277845 A1 | 11/2012 | Bowe |
| 2012/0283757 A1 | 11/2012 | Miller et al. |
| 2012/0283824 A1 | 11/2012 | Lutter et al. |
| 2012/0290062 A1 | 11/2012 | McNamara et al. |
| 2012/0296349 A1 | 11/2012 | Smith et al. |
| 2012/0296360 A1 | 11/2012 | Norris et al. |
| 2012/0296417 A1 | 11/2012 | Hill et al. |
| 2012/0296418 A1 | 11/2012 | Bonyuet et al. |
| 2012/0296419 A1 | 11/2012 | Richardson |
| 2012/0300063 A1 | 11/2012 | Majkrzak et al. |
| 2012/0303116 A1 | 11/2012 | Gorman, III et al. |
| 2012/0310328 A1 | 12/2012 | Olson et al. |
| 2012/0310330 A1 | 12/2012 | Buchbinder et al. |
| 2012/0323313 A1 | 12/2012 | Seguin |
| 2012/0323316 A1 | 12/2012 | Chau et al. |
| 2012/0323317 A1 | 12/2012 | Karapetian et al. |
| 2012/0330408 A1 | 12/2012 | Hillukka et al. |
| 2012/0330410 A1 | 12/2012 | Hammer et al. |
| 2012/0330411 A1 | 12/2012 | Gross et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0023758 A1 | 1/2013 | Fabro |
| 2013/0030519 A1 | 1/2013 | Tran et al. |
| 2013/0030522 A1 | 1/2013 | Rowe et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0066341 A1 | 3/2013 | Ketai et al. |
| 2013/0066342 A1 | 3/2013 | Dell et al. |
| 2013/0079872 A1 | 3/2013 | Gallagher |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0116779 A1 | 5/2013 | Weber |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0123910 A1 | 5/2013 | Cartledge et al. |
| 2013/0131791 A1 | 5/2013 | Hlavka et al. |
| 2013/0131792 A1 | 5/2013 | Miller et al. |
| 2013/0138068 A1 | 5/2013 | Hu et al. |
| 2013/0144381 A1 | 6/2013 | Quadri et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0178930 A1 | 7/2013 | Straubinger et al. |
| 2013/0190857 A1 | 7/2013 | Mitra et al. |
| 2013/0190861 A1 | 7/2013 | Chau et al. |
| 2013/0190863 A1 | 7/2013 | Call et al. |
| 2013/0190866 A1 | 7/2013 | Zipory et al. |
| 2013/0197622 A1 | 8/2013 | Mitra et al. |
| 2013/0197632 A1 | 8/2013 | Kovach et al. |
| 2013/0204361 A1 | 8/2013 | Adams et al. |
| 2013/0211501 A1 | 8/2013 | Buckley et al. |
| 2013/0211508 A1 | 8/2013 | Lane et al. |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0245742 A1 | 9/2013 | Norris |
| 2013/0253634 A1 | 9/2013 | Wilson et al. |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0274870 A1 | 10/2013 | Lombardi et al. |
| 2013/0274873 A1 | 10/2013 | Delaloye et al. |
| 2013/0281988 A1 | 10/2013 | Magnin et al. |
| 2013/0282059 A1 | 10/2013 | Ketai et al. |
| 2013/0289711 A1 | 10/2013 | Liddy et al. |
| 2013/0289718 A1 | 10/2013 | Tsukashima et al. |
| 2013/0289740 A1 | 10/2013 | Liddy et al. |
| 2013/0297013 A1 | 11/2013 | Klima et al. |
| 2013/0304093 A1 | 11/2013 | Serina et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0325118 A1 | 12/2013 | Cartledge |

(56)  References Cited

U.S. PATENT DOCUMENTS

| | | |
|---|---|---|
| 2013/0331929 A1 | 12/2013 | Mitra et al. |
| 2014/0000112 A1 | 1/2014 | Braido et al. |
| 2014/0005767 A1 | 1/2014 | Glazier et al. |
| 2014/0005778 A1 | 1/2014 | Buchbinder et al. |
| 2014/0018911 A1 | 1/2014 | Zhou et al. |
| 2014/0018914 A1 | 1/2014 | Zipory et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0099726 A1 | 4/2014 | Heller |
| 2014/0100653 A1 | 4/2014 | Savage et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135799 A1 | 5/2014 | Henderson |
| 2014/0135894 A1 | 5/2014 | Norris et al. |
| 2014/0135895 A1 | 5/2014 | Andress et al. |
| 2014/0142619 A1 | 5/2014 | Serina et al. |
| 2014/0142681 A1 | 5/2014 | Norris |
| 2014/0142688 A1 | 5/2014 | Duffy et al. |
| 2014/0142695 A1 | 5/2014 | Gross et al. |
| 2014/0148849 A1 | 5/2014 | Serina et al. |
| 2014/0148891 A1 | 5/2014 | Johnson |
| 2014/0148898 A1 | 5/2014 | Gross et al. |
| 2014/0155783 A1 | 6/2014 | Starksen et al. |
| 2014/0163668 A1 | 6/2014 | Rafiee |
| 2014/0163670 A1 | 6/2014 | Alon et al. |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188108 A1 | 7/2014 | Goodine et al. |
| 2014/0188140 A1 | 7/2014 | Meier et al. |
| 2014/0188210 A1 | 7/2014 | Beard et al. |
| 2014/0188215 A1 | 7/2014 | Hlavka et al. |
| 2014/0188221 A1 | 7/2014 | Chung et al. |
| 2014/0194970 A1 | 7/2014 | Chobotov |
| 2014/0194971 A1 | 7/2014 | McNamara |
| 2014/0194976 A1 | 7/2014 | Starksen et al. |
| 2014/0194981 A1 | 7/2014 | Menk et al. |
| 2014/0194983 A1 | 7/2014 | Kovalsky et al. |
| 2014/0200649 A1 | 7/2014 | Essinger et al. |
| 2014/0207175 A1 | 7/2014 | Aggerholm |
| 2014/0207231 A1 | 7/2014 | Hacohen et al. |
| 2014/0214157 A1 | 7/2014 | Börtlein et al. |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0275757 A1 | 9/2014 | Goodwin et al. |
| 2014/0276648 A1 | 9/2014 | Hammer et al. |
| 2014/0277045 A1 | 9/2014 | Fazio et al. |
| 2014/0277054 A1 | 9/2014 | McNamara et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277412 A1 | 9/2014 | Börtlein et al. |
| 2014/0277413 A1 | 9/2014 | Richter et al. |
| 2014/0277417 A1 | 9/2014 | Schraut et al. |
| 2014/0277418 A1 | 9/2014 | Miller |
| 2014/0277419 A1 | 9/2014 | Garde et al. |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0324164 A1 | 10/2014 | Gross et al. |
| 2014/0329225 A1 | 11/2014 | Morin |
| 2014/0330371 A1 | 11/2014 | Gloss et al. |
| 2014/0331475 A1 | 11/2014 | Duffy et al. |
| 2014/0336744 A1 | 11/2014 | Tani et al. |
| 2014/0343668 A1 | 11/2014 | Zipory et al. |
| 2014/0343670 A1 | 11/2014 | Bakis et al. |
| 2014/0350565 A1 | 11/2014 | Yacoby et al. |
| 2014/0350662 A1 | 11/2014 | Vaturi |
| 2014/0350670 A1 | 11/2014 | Keränen |
| 2014/0358222 A1 | 12/2014 | Gorman, III et al. |
| 2014/0358224 A1 | 12/2014 | Tegels et al. |
| 2014/0378331 A1 | 12/2014 | Morin |
| 2014/0379006 A1 | 12/2014 | Sutherland et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0012087 A1 | 1/2015 | Miller et al. |
| 2015/0018940 A1 | 1/2015 | Quill et al. |
| 2015/0018944 A1 | 1/2015 | O'Connor et al. |
| 2015/0032205 A1 | 1/2015 | Matheny |
| 2015/0045880 A1 | 2/2015 | Hacohen |
| 2015/0045881 A1 | 2/2015 | Lim |
| 2015/0051697 A1 | 2/2015 | Spence et al. |
| 2015/0073544 A1 | 3/2015 | Gorman, III et al. |
| 2015/0081011 A1 | 3/2015 | Young et al. |
| 2015/0081014 A1 | 3/2015 | Gross et al. |
| 2015/0094802 A1 | 4/2015 | Buchbinder et al. |
| 2015/0105855 A1 | 4/2015 | Cabiri et al. |
| 2015/0119796 A1 | 4/2015 | Finch |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0148731 A1 | 5/2015 | McNamara et al. |
| 2015/0148894 A1 | 5/2015 | Damm et al. |
| 2015/0148896 A1 | 5/2015 | Karapetian et al. |
| 2015/0157457 A1 | 6/2015 | Hacohen |
| 2015/0157458 A1 | 6/2015 | Thambar et al. |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0182336 A1 | 7/2015 | Zipory et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0230923 A1 | 8/2015 | Levi |
| 2015/0230924 A1 | 8/2015 | Miller et al. |
| 2015/0238313 A1 | 8/2015 | Spence et al. |
| 2015/0238315 A1 | 8/2015 | Rabito et al. |
| 2015/0245908 A1 | 9/2015 | Nitzan et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272731 A1 | 10/2015 | Racchini et al. |
| 2015/0272734 A1 | 10/2015 | Sheps et al. |
| 2015/0282964 A1 | 10/2015 | Beard et al. |
| 2015/0305903 A1 | 10/2015 | Kitaoka |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |

(56) References Cited

U.S. PATENT DOCUMENTS

| | | |
|---|---|---|
| 2015/0359629 A1 | 12/2015 | Ganesan et al. |
| 2015/0359631 A1 | 12/2015 | Sheahan et al. |
| 2016/0008129 A1 | 1/2016 | Siegel |
| 2016/0022423 A1 | 1/2016 | McNamara et al. |
| 2016/0022970 A1 | 1/2016 | Forcucci et al. |
| 2016/0030165 A1 | 2/2016 | Mitra et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0089482 A1 | 3/2016 | Siegenthaler |
| 2016/0095700 A1 | 4/2016 | Righini |
| 2016/0100939 A1 | 4/2016 | Armstrong et al. |
| 2016/0106537 A1 | 4/2016 | Christianson et al. |
| 2016/0106539 A1 | 4/2016 | Buchbinder et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120550 A1 | 5/2016 | McNamara et al. |
| 2016/0125160 A1 | 5/2016 | Heneghan et al. |
| 2016/0157862 A1 | 6/2016 | Hernandez et al. |
| 2016/0166381 A1 | 6/2016 | Sugimoto et al. |
| 2016/0175095 A1 | 6/2016 | Dienno et al. |
| 2016/0184098 A1 | 6/2016 | Vaturi |
| 2016/0200773 A1 | 7/2016 | Morin |
| 2016/0213473 A1 | 7/2016 | Hacohen et al. |
| 2016/0220367 A1 | 8/2016 | Barrett |
| 2016/0228244 A1 | 8/2016 | Cerf et al. |
| 2016/0228247 A1 | 8/2016 | Maimon et al. |
| 2016/0228249 A1 | 8/2016 | Mantanus et al. |
| 2016/0242902 A1 | 8/2016 | Morriss et al. |
| 2016/0245802 A1 | 8/2016 | Morin et al. |
| 2016/0258939 A1 | 9/2016 | Morin et al. |
| 2016/0262885 A1 | 9/2016 | Sandstrom et al. |
| 2016/0266089 A1 | 9/2016 | Morin et al. |
| 2016/0270911 A1 | 9/2016 | Ganesan et al. |
| 2016/0296328 A1 | 10/2016 | Tabor et al. |
| 2016/0296330 A1 | 10/2016 | Hacohen |
| 2016/0296332 A1 | 10/2016 | Zhou et al. |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056169 A1 | 3/2017 | Johnson et al. |
| 2017/0056171 A1 | 3/2017 | Cooper et al. |
| 2017/0065407 A1 | 3/2017 | Hacohen et al. |
| 2017/0065411 A1 | 3/2017 | Grundeman et al. |
| 2017/0074855 A1 | 3/2017 | Morin et al. |
| 2017/0100236 A1 | 4/2017 | Robertson et al. |
| 2017/0113026 A1 | 4/2017 | Finch et al. |
| 2017/0128205 A1 | 5/2017 | Tamir et al. |
| 2017/0128705 A1 | 5/2017 | Forcucci et al. |
| 2017/0135816 A1 | 5/2017 | Lashinski et al. |
| 2017/0143938 A1 | 5/2017 | Ogle et al. |
| 2017/0165054 A1 | 6/2017 | Benson et al. |
| 2017/0165063 A1 | 6/2017 | Anderson et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0234850 A1 | 8/2017 | Morin |
| 2017/0239048 A1 | 8/2017 | Goldfarb et al. |
| 2017/0252159 A1 | 9/2017 | Hacohen et al. |
| 2017/0266003 A1 | 9/2017 | Hammer et al. |
| 2017/0281337 A1 | 10/2017 | Campbell |
| 2017/0325948 A1 | 11/2017 | Wallace et al. |
| 2017/0333183 A1 | 11/2017 | Backus |
| 2017/0333187 A1 | 11/2017 | Hariton et al. |
| 2017/0349940 A1 | 12/2017 | Morin et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0023114 A1 | 1/2018 | Morin et al. |
| 2018/0023115 A1 | 1/2018 | Morin et al. |
| 2018/0028215 A1 | 2/2018 | Cohen |
| 2018/0028311 A1 | 2/2018 | Hacohen |
| 2018/0049873 A1 | 2/2018 | Manash et al. |
| 2018/0055628 A1 | 3/2018 | Patel et al. |
| 2018/0055629 A1 | 3/2018 | Oba et al. |
| 2018/0055630 A1 | 3/2018 | Patel et al. |
| 2018/0098850 A1 | 4/2018 | Rafiee et al. |
| 2018/0116790 A1 | 5/2018 | Ratz et al. |
| 2018/0116843 A1 | 5/2018 | Schreck et al. |
| 2018/0125644 A1 | 5/2018 | Conklin |
| 2018/0132999 A1 | 5/2018 | Perouse |
| 2018/0133003 A1 | 5/2018 | Levi |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0153695 A1 | 6/2018 | Cunningham et al. |
| 2018/0153696 A1 | 6/2018 | Albitov et al. |
| 2018/0161159 A1 | 6/2018 | Lee et al. |
| 2018/0177593 A1 | 6/2018 | Hariton et al. |
| 2018/0177594 A1 | 6/2018 | Patel et al. |
| 2018/0185148 A1 | 7/2018 | Hariton et al. |
| 2018/0206982 A1 | 7/2018 | Haivatov et al. |
| 2018/0206983 A1 | 7/2018 | Noe et al. |
| 2018/0214263 A1 | 8/2018 | Rolando et al. |
| 2018/0243086 A1 | 8/2018 | Barbarino et al. |
| 2018/0250126 A1 | 9/2018 | O'connor et al. |
| 2018/0250130 A1 | 9/2018 | Hariton et al. |
| 2018/0250147 A1 | 9/2018 | Syed |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0280136 A1 | 10/2018 | Hariton et al. |
| 2018/0289479 A1 | 10/2018 | Hariton et al. |
| 2018/0296333 A1 | 10/2018 | Dixon et al. |
| 2018/0296336 A1 | 10/2018 | Cooper et al. |
| 2018/0296341 A1 | 10/2018 | Noe et al. |
| 2018/0325671 A1 | 11/2018 | Abunassar et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0344490 A1 | 12/2018 | Fox et al. |
| 2018/0353294 A1 | 12/2018 | Calomeni et al. |
| 2018/0360457 A1 | 12/2018 | Ellis et al. |
| 2019/0000613 A1 | 1/2019 | Delgado et al. |
| 2019/0008640 A1 | 1/2019 | Cooper et al. |
| 2019/0015093 A1 | 1/2019 | Hacohen et al. |
| 2019/0015200 A1 | 1/2019 | Delgado et al. |
| 2019/0021852 A1 | 1/2019 | Delgado et al. |
| 2019/0021857 A1 | 1/2019 | Hacohen et al. |
| 2019/0038404 A1 | 2/2019 | Iamberger et al. |
| 2019/0038405 A1 | 2/2019 | Iamberger et al. |
| 2019/0046314 A1 | 2/2019 | Levi et al. |
| 2019/0053895 A1 | 2/2019 | Levi |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |

(56) References Cited

U.S. PATENT DOCUMENTS

| | | |
|---|---|---|
| 2019/0060070 A1 | 2/2019 | Groothuis et al. |
| 2019/0069997 A1 | 3/2019 | Ratz et al. |
| 2019/0069998 A1 | 3/2019 | Hacohen |
| 2019/0076244 A1 | 3/2019 | Yohanan et al. |
| 2019/0076245 A1 | 3/2019 | Arcaro et al. |
| 2019/0083242 A1 | 3/2019 | Hariton et al. |
| 2019/0083243 A1 | 3/2019 | Hariton et al. |
| 2019/0083244 A1 | 3/2019 | Hariton et al. |
| 2019/0083245 A1 | 3/2019 | Hariton et al. |
| 2019/0083246 A1 | 3/2019 | Hariton et al. |
| 2019/0083247 A1 | 3/2019 | Hariton et al. |
| 2019/0083248 A1 | 3/2019 | Hariton et al. |
| 2019/0083249 A1 | 3/2019 | Hariton et al. |
| 2019/0083250 A1 | 3/2019 | Hariton et al. |
| 2019/0083251 A1 | 3/2019 | Hariton et al. |
| 2019/0083252 A1 | 3/2019 | Hariton et al. |
| 2019/0083253 A1 | 3/2019 | Hariton et al. |
| 2019/0083254 A1 | 3/2019 | Hariton et al. |
| 2019/0083261 A1 | 3/2019 | Perszyk et al. |
| 2019/0083262 A1 | 3/2019 | Hariton et al. |
| 2019/0083263 A1 | 3/2019 | Hariton et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0175342 A1 | 6/2019 | Hariton et al. |
| 2019/0183639 A1 | 6/2019 | Moore |
| 2019/0183644 A1 | 6/2019 | Hacohen |
| 2019/0192295 A1 | 6/2019 | Spence et al. |
| 2019/0216602 A1 | 7/2019 | Lozonschi |
| 2019/0224008 A1 | 7/2019 | Bressloff et al. |
| 2019/0231525 A1 | 8/2019 | Hariton et al. |
| 2019/0240010 A1 | 8/2019 | Hacohen |
| 2019/0254818 A1 | 8/2019 | Quill et al. |
| 2019/0262507 A1 | 8/2019 | Adamek-bowers et al. |
| 2019/0321172 A1 | 10/2019 | Gross et al. |
| 2019/0328519 A1 | 10/2019 | Hariton et al. |
| 2019/0336280 A1 | 11/2019 | Naor |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000449 A1 | 1/2020 | Goldfarb et al. |
| 2020/0000579 A1 | 1/2020 | Manash et al. |
| 2020/0000580 A1 | 1/2020 | Hacohen |
| 2020/0015964 A1 | 1/2020 | Noe et al. |
| 2020/0030098 A1 | 1/2020 | Delgado et al. |
| 2020/0038181 A1 | 2/2020 | Hariton et al. |
| 2020/0046496 A1 | 2/2020 | Hammer et al. |
| 2020/0046497 A1 | 2/2020 | Hariton et al. |
| 2020/0054335 A1 | 2/2020 | Hernandez et al. |
| 2020/0054451 A1 | 2/2020 | Hariton et al. |
| 2020/0060818 A1 | 2/2020 | Geist et al. |
| 2020/0069417 A1 | 3/2020 | Morin et al. |
| 2020/0069424 A1 | 3/2020 | Hariton et al. |
| 2020/0078002 A1 | 3/2020 | Hacohen et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0129294 A1 | 4/2020 | Hariton et al. |
| 2020/0138567 A1 | 5/2020 | Marr et al. |
| 2020/0146671 A1 | 5/2020 | Hacohen et al. |
| 2020/0146824 A1 | 5/2020 | Hammer et al. |
| 2020/0163760 A1 | 5/2020 | Hariton et al. |
| 2020/0163761 A1 | 5/2020 | Hariton et al. |
| 2020/0205969 A1 | 7/2020 | Hacohen |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0281721 A1 | 9/2020 | Hariton et al. |
| 2020/0297486 A1 | 9/2020 | Hariton et al. |
| 2020/0306037 A1 | 10/2020 | Siegel et al. |
| 2020/0315786 A1 | 10/2020 | Metchik et al. |
| 2020/0315789 A1 | 10/2020 | Hariton et al. |
| 2020/0315797 A1 | 10/2020 | Hariton et al. |
| 2020/0330221 A1 | 10/2020 | Hacohen |
| 2020/0330227 A1 | 10/2020 | Hacohen |
| 2020/0337842 A1 | 10/2020 | Metchik et al. |
| 2020/0360139 A1 | 11/2020 | Hammer et al. |
| 2020/0390546 A1 | 12/2020 | Hariton et al. |
| 2020/0390548 A1 | 12/2020 | Hariton et al. |
| 2020/0397573 A1 | 12/2020 | Hariton et al. |
| 2021/0085455 A1 | 3/2021 | Bateman et al. |
| 2021/0085457 A1 | 3/2021 | Hariton et al. |
| 2021/0093449 A1 | 4/2021 | Hariton et al. |
| 2021/0106419 A1 | 4/2021 | Abunassar |
| 2021/0113331 A1 | 4/2021 | Quadri et al. |
| 2021/0137680 A1 | 5/2021 | Kizuka et al. |
| 2021/0145578 A1 | 5/2021 | Hariton et al. |
| 2021/0169467 A1 | 6/2021 | Hacohen et al. |
| 2021/0196461 A1 | 7/2021 | Hariton et al. |
| 2021/0259835 A1 | 8/2021 | Tyler, II et al. |
| 2021/0322167 A1 | 10/2021 | Hariton et al. |
| 2021/0330456 A1 | 10/2021 | Hacohen et al. |
| 2021/0361422 A1 | 11/2021 | Gross et al. |
| 2021/0361426 A1 | 11/2021 | Hacohen |
| 2021/0393402 A1 | 12/2021 | Hammer et al. |
| 2021/0401573 A1 | 12/2021 | Gross et al. |
| 2022/0000612 A1 | 1/2022 | Hacohen |
| 2022/0023036 A1 | 1/2022 | Levi et al. |
| 2022/0061984 A1 | 3/2022 | Humair et al. |
| 2022/0105238 A1 | 4/2022 | Reimer et al. |
| 2022/0151779 A1 | 5/2022 | Pintor |
| 2022/0175526 A1 | 6/2022 | Albitov et al. |
| 2022/0338985 A1 | 10/2022 | Hariton et al. |
| 2023/0049163 A1 | 2/2023 | Hariton et al. |
| 2023/0137909 A1 | 5/2023 | Hariton et al. |
| 2023/0201015 A1 | 6/2023 | Gurovich et al. |
| 2023/0255764 A9 | 8/2023 | Hariton et al. |
| 2023/0346549 A1 | 11/2023 | Hariton et al. |
| 2023/0346550 A1 | 11/2023 | Gross et al. |
| 2024/0050227 A1 | 2/2024 | Hacohen |
| 2024/0081983 A1 | 3/2024 | Hariton et al. |

FOREIGN PATENT DOCUMENTS

| | | |
|---|---|---|
| CN | 101653365 | 2/2010 |
| CN | 202313807 | 7/2012 |
| CN | 103974674 | 8/2014 |
| CN | 103997990 | 8/2014 |
| CN | 105324091 | 2/2016 |
| CN | 112603598 | 4/2021 |
| EP | 0170262 | 2/1986 |
| EP | 06/14342 | 9/1994 |
| EP | 10/06905 | 6/2000 |
| EP | 0954257 | 8/2000 |
| EP | 1258437 | 11/2002 |
| EP | 1264582 | 12/2002 |
| EP | 0871417 | 10/2003 |
| EP | 1266641 | 10/2004 |
| EP | 1034753 | 2/2005 |
| EP | 1258232 | 1/2006 |
| EP | 1637092 | 3/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 2446915 | 5/2012 |
| EP | 2088965 | 11/2012 |
| EP | 2641569 | 9/2013 |
| EP | 1768630 | 1/2015 |
| EP | 1861045 | 3/2015 |
| EP | 1465555 | 5/2015 |
| EP | 2219558 | 8/2015 |
| EP | 2349124 | 10/2018 |

(56)  References Cited

FOREIGN PATENT DOCUMENTS

| | | |
|---|---|---|
| EP | 2739214 | 10/2018 |
| EP | 3417813 | 12/2018 |
| EP | 3583922 | 12/2019 |
| EP | 3270825 | 4/2020 |
| EP | 2485795 | 9/2020 |
| IL | 223448 | 12/2012 |
| JP | S53152790 | 12/1978 |
| KR | 20010046894 | 6/2001 |
| WO | 92/05093 | 4/1992 |
| WO | 93/10714 | 6/1993 |
| WO | 96/39963 | 12/1996 |
| WO | 96/40344 | 12/1996 |
| WO | 97/01369 | 1/1997 |
| WO | 98/46149 | 10/1998 |
| WO | 1998/043557 | 10/1998 |
| WO | 1999/030647 | 6/1999 |
| WO | 00/22981 | 4/2000 |
| WO | 2000-047139 | 8/2000 |
| WO | 01/26586 | 4/2001 |
| WO | 01/56457 | 8/2001 |
| WO | 2001-062189 | 8/2001 |
| WO | 01/82832 | 11/2001 |
| WO | 02/085250 | 10/2002 |
| WO | 02/085251 | 10/2002 |
| WO | 02/085252 | 10/2002 |
| WO | 2003/020179 | 3/2003 |
| WO | 2003/028558 | 4/2003 |
| WO | 03/047467 | 6/2003 |
| WO | 2003/049647 | 6/2003 |
| WO | 2003/105667 | 12/2003 |
| WO | 2004/028399 | 4/2004 |
| WO | 04/103434 | 12/2004 |
| WO | 2004/108191 | 12/2004 |
| WO | 05/021063 | 3/2005 |
| WO | 05/046488 | 5/2005 |
| WO | 2005/062931 | 7/2005 |
| WO | 2005/107650 | 11/2005 |
| WO | 2006/007389 | 1/2006 |
| WO | 2006/007401 | 1/2006 |
| WO | 06/012013 | 2/2006 |
| WO | 06/012038 | 2/2006 |
| WO | 06/054930 | 5/2006 |
| WO | 2006/065212 | 6/2006 |
| WO | 2006/070372 | 7/2006 |
| WO | 06/086434 | 8/2006 |
| WO | 2006/089236 | 8/2006 |
| WO | 2006/091163 | 8/2006 |
| WO | 06/097931 | 9/2006 |
| WO | 06/105084 | 10/2006 |
| WO | 2006/113906 | 10/2006 |
| WO | 06/116558 | 11/2006 |
| WO | 2006/128193 | 11/2006 |
| WO | 07/011799 | 1/2007 |
| WO | 2007/030063 | 3/2007 |
| WO | 2007/047488 | 4/2007 |
| WO | 2007/059252 | 5/2007 |
| WO | 07/121314 | 10/2007 |
| WO | 07/136783 | 11/2007 |
| WO | 07/136981 | 11/2007 |
| WO | 08/013915 | 1/2008 |
| WO | 2008/014144 | 1/2008 |
| WO | 2008/029296 | 3/2008 |
| WO | 2008/031103 | 3/2008 |
| WO | 2008/058940 | 5/2008 |
| WO | 08/068756 | 6/2008 |
| WO | 2008/070797 | 6/2008 |
| WO | 2008/103722 | 8/2008 |
| WO | 2009/026563 | 2/2009 |
| WO | 09/033469 | 3/2009 |
| WO | 09/053497 | 4/2009 |
| WO | 2009/080801 | 7/2009 |
| WO | 2009/091509 | 7/2009 |
| WO | 2009/108942 | 9/2009 |
| WO | 2009/160631 | 10/2009 |
| WO | 10/004546 | 1/2010 |
| WO | 2010/000454 | 1/2010 |
| WO | 2010/005827 | 1/2010 |
| WO | 2010/006627 | 1/2010 |
| WO | 2010/006905 | 1/2010 |
| WO | 2010/027485 | 3/2010 |
| WO | 2010/037141 | 4/2010 |
| WO | 2010/044851 | 4/2010 |
| WO | 2010/045297 | 4/2010 |
| WO | 2010/057262 | 5/2010 |
| WO | 2010/073246 | 7/2010 |
| WO | 2010/081033 | 7/2010 |
| WO | 2010/085649 | 7/2010 |
| WO | 2010/121076 | 10/2010 |
| WO | 2010/128502 | 11/2010 |
| WO | 2010/128503 | 11/2010 |
| WO | 2010/150178 | 12/2010 |
| WO | 2011/025972 | 3/2011 |
| WO | 2011/051942 | 5/2011 |
| WO | 2011/057087 | 5/2011 |
| WO | 2011/067770 | 6/2011 |
| WO | 2011/069048 | 6/2011 |
| WO | 2011/072084 | 6/2011 |
| WO | 2011/089401 | 7/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011/144351 | 11/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 2012/024428 | 2/2012 |
| WO | 2012/036740 | 3/2012 |
| WO | 2012/048035 | 4/2012 |
| WO | 2012/068541 | 5/2012 |
| WO | 2012/127309 | 9/2012 |
| WO | 2012/176195 | 12/2012 |
| WO | 2012/177942 | 12/2012 |
| WO | 2012/178115 | 12/2012 |
| WO | 2013/021374 | 2/2013 |
| WO | 2013/021375 | 2/2013 |
| WO | 2013/021384 | 2/2013 |
| WO | 2013/028387 | 2/2013 |
| WO | 2013/059743 | 4/2013 |
| WO | 2013/059747 | 4/2013 |
| WO | 2013/069019 | 5/2013 |
| WO | 2013/072496 | 5/2013 |
| WO | 2013/078497 | 6/2013 |
| WO | 2013/088327 | 6/2013 |
| WO | 2013/114214 | 8/2013 |
| WO | 2013/128436 | 9/2013 |
| WO | 2013/175468 | 11/2013 |
| WO | 2014/022124 | 2/2014 |
| WO | 2014/064694 | 5/2014 |
| WO | 2014/064695 | 5/2014 |
| WO | 2014/076696 | 5/2014 |
| WO | 2014/087402 | 6/2014 |
| WO | 2014/099655 | 6/2014 |
| WO | 2014/115149 | 7/2014 |
| WO | 2014/121275 | 8/2014 |
| WO | 2014/121280 | 8/2014 |
| WO | 2014/144937 | 9/2014 |
| WO | 2014/145338 | 9/2014 |
| WO | 2014/164151 | 10/2014 |
| WO | 2014/164364 | 10/2014 |
| WO | 2014/194178 | 12/2014 |
| WO | 2014/195786 | 12/2014 |
| WO | 2014/210124 | 12/2014 |
| WO | 2015/059699 | 4/2015 |
| WO | 2015/173794 | 11/2015 |
| WO | 2015/191923 | 12/2015 |
| WO | 2016/016899 | 2/2016 |
| WO | 2016/093877 | 6/2016 |
| WO | 2016/098104 | 6/2016 |
| WO | 2016/113743 | 7/2016 |
| WO | 2016/125160 | 8/2016 |

(56)                    References Cited

FOREIGN PATENT DOCUMENTS

| WO | 2016/150806 | 9/2016 |
| WO | 2016/183526 | 11/2016 |
| WO | 2017/223486 | 12/2017 |
| WO | 2018/025260 | 2/2018 |
| WO | 2018/025263 | 2/2018 |
| WO | 2018/029680 | 2/2018 |
| WO | 2018/039631 | 3/2018 |
| WO | 2018/106837 | 6/2018 |
| WO | 2018/108837 | 6/2018 |
| WO | 2018/112429 | 6/2018 |
| WO | 2018/118717 | 6/2018 |
| WO | 2018/131042 | 7/2018 |
| WO | 2018/131043 | 7/2018 |
| WO | 2019/026059 | 2/2019 |
| WO | 2019/027507 | 2/2019 |
| WO | 2019/030753 | 2/2019 |
| WO | 2019/077595 | 4/2019 |
| WO | 2019/086958 | 5/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/167677 | 8/2020 |
| WO | 2021/156866 | 8/2021 |
| WO | 2021/178400 | 9/2021 |
| WO | 2021/186424 | 9/2021 |
| WO | 2022/015910 | 1/2022 |
| WO | 2022/046568 | 3/2022 |
| WO | 2022/061017 | 3/2022 |
| WO | 2022/118316 | 6/2022 |
| WO | 2023/009379 | 2/2023 |

OTHER PUBLICATIONS

An Office Action dated Dec. 31, 2012, which issued during the prosecution of U.S. Appl. No. 13/044,694.
An Office Action dated Feb. 6, 2013, which issued during the prosecution of U.S. Appl. No. 13/412,814.
Langer F et al., "Ring plus String: Papillary muscle repositioning as an adjunctive repair technique for ischemic mitral regurgitation," J Thorac Cardiovasc Surg 133:247-9, Jan. 2007.
Langer F et al., "Ring+String: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
Jansen, J., Willeke, S., Reul, H. and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated Dec. 5, 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.
U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.

An International Search Report and a Written Opinion both dated Feb. 6, 2013, which issued during the prosecution of Applicant's PCT/IL12/00292.
An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.
An Office Action dated Feb. 15, 2013, which issued during the prosecution of U.S. Appl. No. 12/840,463.
An Office Action dated Feb. 10, 2014, which issued during the prosecution of U.S. Appl. No. 13/033,852.
An Office Action dated Sep. 19, 2014, which issued during the prosecution of U.S. Appl. No. 13/044,694.
An International Search Report and a Written Opinion both dated Sep. 4, 2014 which issued during the prosecution of Applicant's PCT/IL2014/050087.
Invitation to Pay Additional Fees dated Jun. 12, 2014 PCT/IL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/412,814.
Dominique Himbert; Mitral Regurgitation and Stenosis from Bioprosthesis and Annuloplasty Failure: Transcatheter approaches and outcomes, 24 pages Oct. 28, 2013.
An International Search Report and a Written Opinion both dated Mar. 17, 2014 which issued during the prosecution of Applicant's PCT/IL2013/050937.
An International Preliminary Report on patentabilty dated Dec. 2, 2013, which issued during the prosecution of Applicant's PCT/IL11/00582.
An Office Action dated Sep. 12, 2013, which issued during the prosecution of U.S. Appl. No. 13/412,814.
An Office Action dated Aug. 2, 2013, which issued during the prosecution of U.S. Appl. No. 13/033,852.
An International Preliminary Report on patentabilty dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution U.S. Appl. No. 13/033,852.
An Office Action dated Feb. 3, 2014, which issued during the prosecution of U.S. Appl. No. 13/811,308.
An International Preliminary Report on patentabilty dated Feb. 11, 2014, which issued during the prosecution of Applicant's PCT/IL12/00292.
An International Preliminary Report on patentabilty dated Feb. 11, 2014, which issued during the prosecution of Applicant's PCT/IL12/00293.
A Notice of Allowance dated Aug. 15, 2014, which issued during the prosecution of U.S. Appl. No. 13/412,814.
An Office Action dated Aug. 14, 2012, which issued during the prosecution of U.S. Appl. No. 12/961,721.
U.S. Appl. No. 61/283,819, filed Dec. 8, 2009.
Notice of Allowance dated Apr. 8, 2016, which issued during the prosecution of U.S. Appl. No. 14/237,258.
U.S. Appl. No. 61/756,034, filed Jan. 24, 2013.

(56) References Cited

OTHER PUBLICATIONS

U.S. Appl. No. 61/756,049, filed Jan. 24, 2013.
An International Preliminary Report on Patentability dated Jan. 31, 2017, which issued during the prosecution of Applicant's PCT/IL2015/050792.
U.S. Appl. No. 62/372,861, filed Aug. 10, 2016.
Notice of Allowance dated Aug. 13, 2018, which issued during the prosecution of U.S. Appl. No. 15/995,597.
Notice of Allowance dated Apr. 20, 2018, which issued during the prosecution of U.S. Appl. No. 15/878,206.
An Office Action dated Dec. 10, 2015, which issued during the prosecution of U.S. Appl. No. 14/237,258.
An International Preliminary Report on Patentability dated Jul. 28, 2015, which issued during the prosecution of Applicant's PCT/IL2014/050087.
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/763,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18, 2015, which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of Design U.S. Appl. No. 29/635,658.
An Office Action dated Jun. 28, 2018, which issued during the prosecution of Design U.S. Appl. No. 29/635,661.
Georg Lutter, MD, et al; "Percutaneous Valve Replacement: Current State and Future Prospects", The Annals of Thoracic Surgery ; vol. 78, pp. 2199-2206, Dec. 2004.
An Office Action dated Jun. 6, 2018, which issued during the prosecution of UK Patent Application No. 1720803.4.
An International Search Report and a Written Opinion both dated Jun. 20, 2018, which issued during the prosecution of Applicant's PCT/IL2018/050024.

An Office Action dated Jun. 18, 2018, which issued during the prosecution of UK Patent Application No. 1800399.6.
An Office Action dated Oct. 23, 2017, which issued during the prosecution of U.S. Appl. No. 14/763,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/213,791.
An Office Action dated Feb. 7, 2018, which issued during the prosecution of U.S. Appl. No. 15/197,069.
An International Search Report and a Written Opinion both dated Nov. 24, 2017, which issued during the prosecution of Applicant's PCT/IL2017/050873.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT/IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
Notice of Allowance dated Dec. 13, 2013, which issued during the prosecution of U.S. Appl. No. 13/675,119.
An International Preliminary Report on Patentability dated Aug. 8, 2017, which issued during the prosecution of Applicant's PCT/IL2016/050125.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An International Preliminary Report on Patentability dated May 19, 2015, which issued during the prosecution of Applicant's PCT/IL2013/050937.
Dusan Pavcnik, MD, PhD2, et al; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11, 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.

(56)                    References Cited

OTHER PUBLICATIONS

Notice of Allowance dated Jul. 1, 2016, which issued during the prosecution of U.S. Appl. No. 14/442,541.
An Office Action dated Mar. 25, 2019, which issued during the prosecution of European Patent Application No. 14710060.6.
An International Search Report and a Written Opinion both dated Nov. 9, 2018, which issued during the prosecution of Applicant's PCT/IL2018/050869.
An International Search Report and a Written Opinion both dated Dec. 5, 2018, which issued during the prosecution of Applicant's PCT/IL2018/050725.
An International Search Report and a Written Opinion both dated Apr. 25, 2019, which issued during the prosecution of Applicant's PCT/IL2019/050142.
An International Preliminary Report on Patentability dated Feb. 12, 2019, which issued during the prosecution of Applicant's PCT/IL2017/050873.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An International Preliminary Report on Patentability dated Feb. 4, 2020, which issued during the prosecution of Applicant's PCT/IL2018/050725.
An International Search Report and a Written Opinion both dated Jan. 25, 2019, which issued during the prosecution of Applicant's PCT/IL2018/051122.
An International Search Report and a Written Opinion both dated May 13, 2019, which issued during the prosecution of Applicant's PCT/IL2018/051350.
An International Preliminary Report on Patentability dated Feb. 5, 2019, which issued during the prosecution of Applicant's PCT/IL2017/050849.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Aug. 1, 2019, which issued during the prosecution of U.S. Appl. No. 15/668,559.
An Office Action dated Jun. 19, 2019, which issued during the prosecution of U.S. Appl. No. 15/682,789.
Notice of Allowance dated Jan. 13, 2020, which issued during the prosecution of U.S. Appl. No. 15/956,956.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
U.S. Appl. No. 62/560,384, filed Sep. 19, 2017.
U.S. Appl. No. 62/112,343, filed Feb. 5, 2015.

An International Preliminary Report on Patentability dated Feb. 11, 2020, which issued during the prosecution of Applicant's PCT/IL2018/050869.
An International Preliminary Report on Patentability dated Oct. 20, 2020, which issued during the prosecution of Applicant's PCT/IL2019/050142.
An Office Action dated Jan. 6, 2020, which issued during the prosecution of U.S. Appl. No. 16/660,231.
An Office Action dated Dec. 31, 2019, which issued during the prosecution of U.S. Appl. No. 16/183,140.
Notice of Allowance dated Apr. 24, 2019, which issued during the prosecution of U.S. Appl. No. 16/045,059.
An Office Action dated Jan. 14, 2020, which issued during the prosecution of U.S. Appl. No. 16/284,331.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
Notice of Allowance dated Jan. 16, 2020, which issued during the prosecution of U.S. Appl. No. 16/532,945.
Notice of Allowance dated Aug. 19, 2020, which issued during the prosecution of U.S. Appl. No. 16/637,166.
Notice of Allowance dated Jul. 27, 2020, which issued during the prosecution of U.S. Appl. No. 16/637,166.
Notice of Allowance dated Jun. 23, 2020, which issued during the prosecution of U.S. Appl. No. 16/637,166.
Notice of Allowance dated May 7, 2020, which issued during the prosecution of U.S. Appl. No. 16/637,166.
Sündermann, Simon H., et al. "Feasibility of the Engager™ aortic transcatheter valve system using a flexible over-the-wire design." European Journal of Cardio-Thoracic Surgery 42.4 (2012): e48-e52.
An Office Action summarized English translation and Search Report dated Jul. 3, 2020, which issued during the prosecution of Chinese Patent Application No. 201780061210.3.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https /books.google.co.il/books?/id=FL/LBQAAQBAJ&1pg=PA198&ots=soqWrDH-v_&dq=%20%22Edwards%20SAPIEN%22&lr&pg=PA20#v=onepage&q=%22Edwards%20SAPIEN%22&f=false ; Downloaded on Jun. 18, 2020.
An International Search Report and a Written Opinion both dated Jun. 24, 2020, which issued during the prosecution of Applicant's PCT/IL2019/051398.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
Notice of Allowance dated Jul. 29, 2020, which issued during the prosecution of U.S. Appl. No. 16/132,937.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Aug. 7, 2020, which issued during the prosecution of U.S. Appl. No. 15/668,659.
Tchetche, D. and Nicolas M. Van Mieghem: "New-generation TAVI devices: description and specifications" EuroIntervention, 2014, No. 10:U90-U100.
An Office Action dated Aug. 23, 2019, which issued during the prosecution of U.S. Appl. No. 15/600,190.
Symetis S.A.: "Acurate neo™ Aortic Bioprosthesis for Implantation using the Acurate neo™ TA Transapical Delivery System in Patients

(56) References Cited

OTHER PUBLICATIONS with Severe Aortic Stenosis," Clinical Investigation Plan, Protocol No. 2015-01, Vs. No. 2, 2015:1-76.
Notice of Allowance dated Sep. 10, 2020, which issued during the prosecution of U.S. Appl. No. 15/600,190.
Notice of Allowance dated Sep. 10, 2020, which issued during the prosecution of U.S. Appl. No. 16/324,339.
Notice of Allowance dated Oct. 19, 2020, which issued during the prosecution of U.S. Appl. No. 16/324,339.
Notice of Allowance dated Sep. 21, 2020, which issued during the prosecution of U.S. Appl. No. 16/269,328.
Notice of Allowance dated Oct. 28, 2020, which issued during the prosecution of U.S. Appl. No. 16/269,328.
Notice of Allowance dated Jan. 16, 2020, which issued during the prosecution of U.S. Appl. No. 15/872,501.
An Office Action dated May 11, 2020, which issued during the prosecution of U.S. Appl. No. 16/811,732.
An Office Action dated Sep. 24, 2020, which issued during the prosecution of U.S. Appl. No. 16/811,732.
Notice of Allowance dated Mar. 29, 2017, which issued during the prosecution of U.S. Appl. No. 14/161,921.
Agarwal et al. International Cardiology Perspective Functional Tricuspid Regurgitation, Circ Cardiovasc Interv 2009;2;2;565-573 (2009).
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Alfieri et al."Novel Suture Device for Beating-Heart Mitral Leaflet Approximation", Ann Thorac Surg. 2002, 74:1488-1493.
Alfieri et al., "The edge to edge technique," The European Association for Cardio-Thoracic Surgery 14th Annual Meeting Oct. 7-11, Book of Procees. (2000).
Amplatzer Cardiac Plug brochure (English pages), AGA Medical Corporation (Plymouth, MN) (copyright 2008-2010, downloaded Jan. 11, 2011).
Amplatzer® Cribriform Occluder. A patient guide to Percutaneous, Transcatheter, Atrial Septal Defect Closuer, AGA Medical Corporation, Apr. 2008.
Amplatzer® Septal Occluder. A patient guide to the Non-Surgical Closuer of the Atrial Septal Defect Using the Amplatzer Septal Occluder System, AGA Medical Corporation, Apr. 2008.
Brennan, Jennifer, 510(k) Summary of safety and effectiveness, Jan. 2008.
Dictionary.com definition of "lock", Jul. 29, 2013.
Dang NC et al. "Simplified Placement of Multiple Artificial Mitral Valve Chords," The Heart Surgery Forum #2005-1005, 8 (3) (2005).
Maisano, The double-orifice technique as a standardized approach to treat mitral . . . , European Journal of Cardio-thoracic Surgery 17 (2000) 201-205.
"Two dimensional real-time ultrasonic imaging of the heart and great vessels", Mayo Clin Proc. vol. 53:271-303, 1978.
Odell JA et al., "Early Results 04yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Swain CP et al., "An endoscopically deliverable tissue-transfixing device for securing biosensors in the gastrointestinal tract," Gastrointestinal Endoscopy 40(6): 730-734 (1994).
An Invitation to pay additional fees dated Jan. 31, 2014, which issued during the prosecution of Applicant's PCT/IL2013/050860.
U.S. Appl. No. 62/030,715, filed Jul. 30, 2014.
U.S. Appl. No. 62/139,854, filed Mar. 30, 2015.
U.S. Appl. No. 61/312,412, filed Mar. 10, 2010.
An Invitation to pay additional fees dated Jan. 31, 2014, which issued during the prosecution of Applicant's PCT/IL2013/050861.

An International Preliminary Report on Patentability dated Dec. 23, 2013, which issued during the prosecution of Applicant's PCT/IL2012/000250.
An International Preliminary Report on Patentability dated Sep. 18, 2007, which issued during the prosecution of Applicant's PCT/IL2006/000342.
An International Preliminary Report on Patentability dated Jun. 5, 2012, which issued during the prosecution of Applicant's PCT/IL2010/001024.
An International Preliminary Report on Patentability dated Apr. 28, 2015, which issued during the prosecution of Applicant's PCT/IL2013/050861.
An International Preliminary Report on Patentability dated Apr. 26, 2016, which issued during the prosecution of Applicant's PCT/IL2014/050914.
An International Preliminary Report on Patentability dated Jun. 10, 2009, which issued during the prosecution of Applicant's PCT/IL07/01503.
An International Preliminary Report on Patentability dated Dec. 18, 2010, which issued during the prosecution of Applicant's PCT/IL09/00593.
An International Preliminary Report on Patentability dated Jun. 29, 2011, which issued during the prosecution of Applicant's PCT/IL2009/001209.
Notice of Allowance dated Aug. 18, 2017, which issued during the prosecution of U.S. Appl. No. 14/689,608.
Notice of Allowance dated Jul. 6, 2017, which issued during the prosecution of U.S. Appl. No. 14/689,608.
Notice of Allowance dated May 22, 2017, which issued during the prosecution of U.S. Appl. No. 14/689,608.
An Office Action dated Apr. 21, 2017, which issued during the prosecution of U.S. Appl. No. 15/213,791.
An Office Action dated Sep. 29, 2017, which issued during the prosecution of U.S. Appl. No. 15/197,069.
An International Preliminary Report on Patentability dated Nov. 9, 2011, which issued during the prosecution of Applicant's PCT/IL2010/000357.
An International Preliminary Report on Patentability dated Nov. 9, 2011 which issued during the prosecution of Applicant's PCT/IL2010/000358.
An International Preliminary Report on Patentability dated Nov. 27, 2012, which issued during the prosecution of Applicant's PCT/IL2011/000404.
An International Preliminary Report on Patentability dated Feb. 4, 2014, which issued during the prosecution of Applicant's PCT/IL2011/000446.
An International Preliminary Report on Patentability dated Jan. 29, 2013, which issued during the prosecution of Applicant's PCT/IL2011/000600.
An International Preliminary Report on Patentability dated Dec. 23, 2014, which issued during the prosecution of Applicant's PCT/IL2012/050451.
A Notice of Allowance dated Jul. 30, 2015, which issued during the prosecution of U.S. Appl. No. 13/319,007.
An Office Action dated Sep. 29, 2014, which issued during the prosecution of U.S. Appl. No. 13/504,870.
An Office Action dated Jan. 13, 2015, which issued during the prosecution of U.S. Appl. No. 13/707,013.
An Office Action dated Mar. 23, 2015, which issued during the prosecution of U.S. Appl. No. 13/707,013.
Notice of Allowance dated Mar. 25, 2015, which issued during the prosecution of U.S. Appl. No. 13/749,153.
An Office Action dated Oct. 3, 2014, which issued during the prosecution of U.S. Appl. No. 13/749,153.
Notice of Allowance dated May 22, 2015, which issued during the prosecution of U.S. Appl. No. 13/749,153.
Notice of Allowance dated Aug. 3, 2015, which issued during the prosecution of U.S. Appl. No. 13/749,153.
An Office Action dated Dec. 19, 2013, which issued during the prosecution of U.S. Appl. No. 14/027,934.
An Office Action dated Feb. 26, 2024, which issued during the prosecution of Canadian Patent Application No. 3,085,266.

(56)                    References Cited

OTHER PUBLICATIONS

Notice of Allowance dated Aug. 24, 2022, which issued during the prosecution of U.S. Appl. No. 16/879,952.
Notice of Allowance dated May 12, 2023, which issued during the prosecution of U.S. Appl. No. 16/896,858.
Notice of Allowance dated Nov. 2, 2023, which issued during the prosecution of U.S. Appl. No. 17/466,785.
Notice of Allowance dated Oct. 17, 2023, which issued during the prosecution of U.S. Appl. No. 17/466,785.
An Office Action dated Jun. 10, 2022, which issued during the prosecution of U.S. Appl. No. 16/768,909.
An Office Action dated Jun. 11, 2014, which issued during the prosecution of U.S. Appl. No. 14/027,934.
An Office Action dated Aug. 22, 2014, which issued during the prosecution of U.S. Appl. No. 14/027,934.
An Office Action dated Apr. 2, 2015, which issued during the prosecution of U.S. Appl. No. 14/027,934.
An Office Action dated Jan. 5, 2016, which issued during the prosecution of U.S. Appl. No. 14/027,934.
An Office Action dated Jan. 5, 2016, which issued during the prosecution of U.S. Appl. No. 14/084,426.
An Office Action dated Mar. 16, 2015, which issued during the prosecution of U.S. Appl. No. 14/084,426.
An Office Action dated Jan. 6, 2016, which issued during the prosecution of U.S. Appl. No. 14/128,756.
An Office Action dated May 11, 2016, which issued during the prosecution of U.S. Appl. No. 14/128,756.
Notice of Allowance dated Oct. 20, 2015, which issued during the prosecution of U.S. Appl. No. 12/996,954.
Notice of Allowance dated Feb. 19, 2014, which issued during the prosecution of U.S. Appl. No. 12/795,192.
An Office Action dated Jul. 20, 2012, which issued during the prosecution of U.S. Appl. No. 12/843,412.
An Office Action dated Mar. 27, 2013, which issued during the prosecution of U.S. Appl. No. 12/843,412.
A Restriction Requirement dated May 1, 2012, which issued during the prosecution of U.S. Appl. No. 12/843,412.
A Notice of Allowance dated May 2, 2013, which issued during the prosecution of U.S. Appl. No. 12/843,412.
A Restriction Requirement dated Nov. 19, 2012, which issued during the prosecution of U.S. Appl. No. 12/926,673.
An Office Action dated Feb. 12, 2013, which issued during the prosecution of U.S. Appl. No. 12/926,673.
An Office Action dated Oct. 22, 2013, which issued during the prosecution of U.S. Appl. No. 12/926,673.
A Notice of Allowance dated Jan. 7, 2014, which issued during the prosecution of U.S. Appl. No. 12/926,673.
An Office Action dated Jul. 6, 2022, which issued during the prosecution of U.S. Appl. No. 16/656,790.
An International Preliminary Report on Patentabilty dated Jul. 28, 2022, which issued during the prosecution of Applicant's PCT/IL2021/050132.
An Office Action dated Oct. 9, 2013, which issued during the prosecution of U.S. Appl. No. 12/996,954.
An Office Action dated Mar. 24, 2015, which issued during the prosecution of U.S. Appl. No. 12/996,954.
An Office Action dated Oct. 5, 2012, which issued during the prosecution of U.S. Appl. No. 12/996,954.
Notice of Allowance dated Jul. 7, 2015, which issued during the prosecution of U.S. Appl. No. 12/996,954.
An Office Action dated Nov. 16, 2018, which issued during the prosecution of U.S. Appl. No. 16/042,028.
An International Search Report with Written Opinion both dated Feb. 2, 2012, which issued during the prosecution of Applicant's PCT/IL2011/000600.
An International Search Report together with Written Opinion both dated Mar. 30, 2011, which issued during the prosecution of Applicant's PCT/IL2010/001024.

An International Search Report and A Written Opinion both dated Feb. 10, 2011, which issued during the prosecution of Applicant's PCT/IL10/00890.
An Office Action dated May 28, 2015, which issued during the prosecution of U.S. Appl. No. 14/128,756.
An Office Action dated Sep. 6, 2018, which issued during the prosecution of U.S. Appl. No. 15/994,022.
An Office Action dated Sep. 7, 2018, which issued during the prosecution of U.S. Appl. No. 15/995,725.
An Office Action dated Nov. 26, 2018, which issued during the prosecution of U.S. Appl. No. 16/040,831.
An Office Action dated Jul. 11, 2018, which issued during the prosecution of U.S. Appl. No. 15/978,494.
An Office Action dated Nov. 23, 2018, which issued during the prosecution of U.S. Appl. No. 16/041,208.
An Office Action dated Jun. 15, 2018, which issued during the prosecution of U.S. Appl. No. 15/970,314.
An Office Action dated Oct. 12, 2018, which issued during the prosecution of U.S. Appl. No. 15/970,314.
An Office Action dated Jul. 26, 2018, which issued during the prosecution of U.S. Appl. No. 15/979,686.
An Office Action dated Sep. 10, 2018, which issued during the prosecution of U.S. Appl. No. 16/008,618.
An International Preliminary Report on Patentability dated Apr. 28, 2015, which issued during the prosecution of Applicant's PCT/IL2013/050860.
Notice of Allowance dated Jun. 22, 2023, which issued during the prosecution of U.S. Appl. No. 17/141,853.
An Office Action dated Apr. 22, 2019, which issued during the prosecution of U.S. Appl. No. 15/668,559.
Notice of Allowance dated Aug. 30, 2019, which issued during the prosecution of U.S. Appl. No. 15/682,789.
Notice of Allowance dated Mar. 29, 2019, which issued during the prosecution of U.S. Appl. No. 15/541,783.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
An Advisory Action dated Dec. 13, 2013, which issued during the prosecution of U.S. Appl. No. 12/961,721.
An Office Action dated Aug. 7, 2015, which issued during the prosecution of U.S. Appl. No. 14/128,756.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated May 30, 2012, which issued during the prosecution of U.S. Appl. No. 12/706,868.
A Notice of Allowance dated Sep. 18, 2012, which issued during the prosecution of U.S. Appl. No. 12/706,868.
Restriction Requirement dated May 5, 2011, which issued during the prosecution of U.S. Appl. No. 12/706,868.
A Restriction Requirement dated Mar. 30, 2012, which issued during the prosecution of U.S. Appl. No. 12/785,717.
An Office Action dated Oct. 5, 2020, which issued during the prosecution of Canadian Patent Application No. 2,973,940.
An Office Action dated Nov. 30, 2020, which issued during the prosecution of U.S. Appl. No. 16/138,129.
An Office Action summarized English translation and Search Report dated Nov. 25, 2020, which issued during the prosecution of Chinese Patent Application No. 201910449820.1.
Notice of Allowance dated Nov. 19, 2020, which issued during the prosecution of U.S. Appl. No. 16/318,025.
An Office Action dated Aug. 2, 2011, which issued during the prosecution of U.S. Appl. No. 12/435,291.
Notice of Allowance dated Dec. 7, 2011, which issued during the prosecution of U.S. Appl. No. 12/435,291.
An Office Action dated Apr. 6, 2010, which issued during the prosecution of Applicant's U.S. Appl. No. 12/484,512.
An Office Action dated Oct. 6, 2010, which issued during the prosecution of Applicant's U.S. Appl. No. 12/484,512.
Notice of Allowance dated Apr. 20, 2011, which issued during the prosecution of U.S. Appl. No. 12/484,512.

(56) References Cited

OTHER PUBLICATIONS

Notice of Allowance dated Mar. 23, 2011, which issued during the prosecution of U.S. Appl. No. 12/484,512.

An Office Action dated Jan. 27, 2012, which issued during the prosecution of U.S. Appl. No. 12/548,991.

An Office Action dated Aug. 6, 2012, which issued during the prosecution of U.S. Appl. No. 12/548,991.

An Advisory Action dated Sep. 6, 2012 which issued during the prosecution of U.S. Appl. No. 12/548,991.

Notice of Allowance dated Jun. 23, 2014, which issued during the prosecution of U.S. Appl. No. 12/548,991.

A Restriction Requirement dated Nov. 14, 2011 which issued during the prosecution of U.S. Appl. No. 12/548,991.

Amendment, Terminal Disclaimer and Extension dated Jun. 27, 2012, which issued during the prosecution of U.S. Appl. No. 12/548,991.

A Restriction Requirement dated Jul. 5, 2012, which issued during the prosecution of U.S. Appl. No. 12/563,930.

An Office Action dated Apr. 2, 2013, which issued during the prosecution of U.S. Appl. No. 12/785,717.

An Office Action dated Dec. 27, 2013, which issued during the prosecution of U.S. Appl. No. 12/785,717.

An Office Action dated Nov. 5, 2012, which issued during the prosecution of U.S. Appl. No. 12/795,026.

An Office Action dated May 10, 2012, which issued during the prosecution of U.S. Appl. No. 12/795,026.

Notice of Allowance dated Nov. 13, 2014, which issued during the prosecution of U.S. Appl. No. 12/795,026.

Notice of Allowance dated Dec. 24, 2014, which issued during the prosecution of U.S. Appl. No. 12/795,026.

A Restriction Requirement dated Jan. 6, 2012, which issued during the prosecution of U.S. Appl. No. 12/795,026.

A Restriction Requirement dated Sep. 14, 2012, which issued during the prosecution of U.S. Appl. No. 12/795,192.

An Office Action dated Aug. 15, 2013, which issued during the prosecution of U.S. Appl. No. 12/795,192.

An Office Action dated Jan. 17, 2013, which issued during the prosecution of U.S. Appl. No. 12/795,192.

Notice of Allowance dated Nov. 19, 2013, which issued during the prosecution of U.S. Appl. No. 12/795,192.

A Notice of Allowance dated Jun. 26, 2012, which issued during the prosecution of U.S. Appl. No. 12/608,316.

An Office Action dated Nov. 14, 2011, which issued during the prosecution of U.S. Appl. No. 12/608,316.

A Restriction Requirement dated Apr. 1, 2011, which issued during the prosecution of U.S. Appl. No. 12/608,316.

An Office Action dated Jul. 6, 2012, which issued during the prosecution of U.S. Appl. No. 12/692,061.

An Office Action dated Jan. 23, 2012, which issued during the prosecution of U.S. Appl. No. 12/692,061.

An Office Action dated Mar. 9, 2012, which issued during the prosecution of U.S. Appl. No. 12/689,635.

An Office Action dated Nov. 30, 2012, which issued during the prosecution of U.S. Appl. No. 12/689,635.

A Notice of Allowance dated May 22, 2013, which issued during the prosecution of U.S. Appl. No. 12/689,635.

Restriction Requirement dated Nov. 14, 2011, which issued during the prosecution of U.S. Appl. No. 12/689,635.

An Office Action dated May 6, 2013, which issued during the prosecution of U.S. Appl. No. 12/689,693.

An Office Action dated Feb. 3, 2014, which issued during the prosecution of U.S. Appl. No. 12/689,693.

Notice of Allowance dated Jun. 11, 2014, which issued during the prosecution of U.S. Appl. No. 12/689,693.

A Restriction Requirement dated Sep. 17, 2012, which issued during the prosecution of U.S. Appl. No. 12/689,693.

A Notice of Allowance dated Sep. 3, 2014, which issued during the prosecution of U.S. Appl. No. 12/689,693.

European Search Report dated Jul. 8, 2016, which issued during the prosecution of Applicant's European App No. 13849843.1.

A Supplementary European Search Report dated Dec. 4, 2012, which issued during the prosecution of European Patent Application No. EP 09834225.6.

A Supplementary European Search Report dated Mar. 28, 2013, which issued during the prosecution of European Patent Application No. EP 1077 2091.4.

Search Report in European Patent Application 10772090.6 dated Jan. 17, 2014.

Supplementary European Search Report dated Oct. 23, 2014 which issued during the prosecution of Applicant's European App No. 10826224.7.

Notice of Allowance dated May 6, 2016, which issued during the prosecution of U.S. Appl. No. 14/667,090.

Notice of Allowance dated Apr. 12, 2016, which issued during the prosecution of U.S. Appl. 14/667,090.

An Office Action dated Jun. 7, 2013 which issued during the prosecution of U.S. Appl. No. 13/141,606.

An Office Action dated Jun. 13, 2014, which issued during the prosecution of U.S. Appl. No. 13/141,606.

Notice of Allowance dated Sep. 29, 2014, which issued during the prosecution of U.S. Appl. No. 13/141,606.

An Office Action dated Feb. 4, 2013 which issued during the prosecution of U.S. Appl. No. 13/141,606.

An English translation of an Office Action dated Apr. 23, 2014 which issued during the prosecution of Chinese Patent Application No. 201080059948.4.

Communication dated Jul. 25, 2014, issued by the State Intellectual Property Office of the P.R. of China in counterpart Application No. 200980157331.3.

An International Search Report and a Written Opinion both dated Jan. 25, 2016, which issued during the prosecution of Applicant's PCT/IL2015/051027.

An International Search Report dated May 19, 2011, which issued during the prosecution of Applicant's PCT/IL2011/00064.

An International Search Report and a Written Opinion both dated Feb. 22, 2013, which issued during the prosecution of Applicant's PCT/IL201/050451.

An International Search Report & Written Opinion both dated Mar. 21, 2014, which issued during the prosecution of Applicant's PCT/IL13/50992.

An International Search Report and Written Opinion both dated Apr. 9, 2014, which issued during the prosecution of Applicant's PCT/IL13/50860.

An International Search Report and a Written Opinion both dated Apr. 15. 2014, which issued during the prosecution of Applicant's PCT/IL2013/050861.

An International Search Report & Written Opinion both dated May 12, 2015, which issued during the prosecution of Applicant's PCT/IL2014/050914.

An International Search Report and a Written Opinion both dated May 30, 2007, which issued during the prosecution of Applicant's PCT/IL2006/000342.

An International Search Report and a Written Opinion both dated Jun. 10, 2010, which issued during the prosecution of Applicant's PCT/IL09/01209.

An International Search Report and a Written Opinion both dated Aug. 17, 2010, which issued during the prosecution of Applicant's PCT/IL10/00357.

An International Search Report & Written Opinion both dated Sep. 8, 2009, which issued during the prosecution of Applicant's PCT/IL09/00593.

An International Search Report and a Written Opinion both dated Sep. 12, 2008, which issued during the prosecution of Applicant's PCT/IL07/01503.

An International Search Report and Written Opinion dated Nov. 8, 2010, which issued during the prosecution of Applicant's PCT/IL2010/000358.

An International Search Report and a Written Opinion both dated Nov. 23, 2011, which issued during the prosecution of Applicant's PCT/IL2011/000446.

Supplementary European Search Report dated Sep. 25, 2015, which issued during the prosecution of Applicant's European App No. 09794095.1.

(56)             References Cited

OTHER PUBLICATIONS

A Supplementary European Search Report dated Feb. 1, 2011, which issued during the prosecution of European Patent Application No. EP 07849540.

An English translation of an Office Action dated Dec. 12, 2013 which issued during the prosecution of Chinese Patent Application No. 200980157331.3.

Communication regarding amended claims filed dated Dec. 27. 2012, regarding European App No. 11792047.0.

An Office Action dated Mar. 23, 2015, which issued during the prosecution of European Patent Application No. EP 09834225.6.

An English translation of an Office Action dated Jul. 17, 2015 which issued during the prosecution of Chinese Patent Application No. 201080059948.4.

An English translation of an Office Action dated Dec. 16, 2015 which issued during the prosecution of Chinese Patent Application No. 201080059948.4.

Communication from the European Patent Office dated Jun. 11, 2015, which issued during the prosecution of European Patent Application No. 11811934.

A communication from the European Patent Office dated Sep. 28, 2011 which issued during the prosecution of European Application No. 09834225.6.

A communication from the European Patent Office dated Oct. 19, 2012 which issued during the prosecution of European Application No. 11792047.0.

An Office Action dated Oct. 23, 2012, which issued during the prosecution of Japanese Patent Application No. 2009-539871.

An English Translation of an Office Action dated Nov. 24, 2015, which issued during the prosecution of Israel Patent Application No. 223448. (the relevant part only).

Notice of Allowance dated Nov. 17, 2015, which issued during the prosecution of U.S. Appl. No. 14/486,226.

Notice of Allowance dated Jan. 29, 2016, which issued during the prosecution of U.S. Appl. No. 14/551,951.

An Office Action dated Jun. 18, 2015, which issued during the prosecution of U.S. Appl. No. 14/551,951.

An Office Action dated Jan. 4, 2016, which issued during the prosecution of U.S. Appl. No. 14/589,100.

An Office Action dated May 4, 2016, which issued during the prosecution of U.S. Appl. No. 14/589,100.

An International Search Report and a Written Opinion both dated Nov. 14, 2011, which issued during the prosecution of Applicant's PCT/IL2011/000404.

An International Search Report and a Written Opinion both dated Dec. 6, 2012 which issued during the prosecution of Applicant's PCT/IL2012/000250.

A Notice of Allowance dated Apr. 3, 2013, which issued during the prosecution of U.S. Appl. No. 12/563,930.

An Office Action dated Aug. 24, 2012, which issued during the prosecution of U.S. Appl. No. 12/563,930.

An Office Action dated Dec. 29, 2011, which issued during the prosecution of U.S. Appl. No. 12/563,952.

A Restriction Requirement dated Oct. 27, 2011, which issued during the prosecution of U.S. Appl. No. 12/563,952.

A Notice of Allowance dated May 24, 2012, which issued during the prosecution of U.S. Appl. No. 12/563,952.

An Office Action dated Apr. 1, 2013 which issued during the prosecution of U.S. Appl. No. 13/167,476.

An Office Action dated Nov. 21, 2013, which issued during the prosecution of U.S. Appl. No. 13/167,476.

An Advisory Action dated Feb. 4, 2014, which issued during the prosecution of U.S. Appl. No. 13/167,476.

A Restriction Requirement dated Oct. 25, 2012 which issued during the prosecution of U.S. Appl. No. 13/167,444.

An Office Action dated Jan. 17, 2013, which issued during the prosecution of U.S. Appl. No. 13/167,444.

An Office Action dated Aug. 26, 2014 which issued during the prosecution of U.S. Appl. No. 13/167,444.

An Office Action dated Aug. 23, 2013 which issued during the prosecution of U.S. Appl. No. 13/167,444.

Notice of Allowance dated Nov. 12, 2015, which issued during the prosecution of U.S. Appl. No. 13/319,007.

Notice of Allowance dated Jan. 7, 2016, which issued during the prosecution of U.S. Appl. No. 13/319,007.

An Office Action dated Oct. 2, 2013, which issued during the prosecution of U.S. Appl. No. 13/167,492.

A Restriction Requirement dated Nov. 2, 2012, which issued during the prosecution of U.S. Appl. No. 13/167,492.

An Office Action dated Feb. 14, 2013 which issued during the prosecution of U.S. Appl. No. 13/167,492.

Notice of Allowance dated Nov. 7, 2014, which issued during the prosecution of U.S. Appl. No. 13/167,492.

An Office Action dated Jun. 10, 2014, which issued during the prosecution of U.S. Appl. No. 13/167,492.

Notice of Allowance dated Dec. 9, 2014, which issued during the prosecution of U.S. Appl. No. 13/167,476.

Notice of Allowance dated Jan. 22, 2015, which issued during the prosecution of U.S. Appl. No. 13/167,444.

An International Preliminary Report on Patentability dated May 1, 2012, which issued during the prosecution of Applicant's PCT/IL2010/000890.

An International Preliminary Report on Patentability dated Jun. 9, 2015, which issued during the prosecution of Applicant's PCT/IL2013/050992.

U.S. Appl. No. 60/873,075, filed Dec. 5, 2006.

U.S. Appl. No. 60/902,146, filed Feb. 16, 2007.

An Office Action dated Mar. 29, 2018, which issued during the prosecution of U.S. Appl. No. 15/188,507.

Notice of Allowance dated Sep. 17, 2014, which issued during the prosecution of U.S. Appl. No. 12/961,721.

An Office Action dated Oct. 1, 2015, which issued during the prosecution of U.S. Appl. No. 14/141,228.

A Restriction Requirement dated Jun. 2, 2014, which issued during the prosecution of U.S. Appl. No. 13/319,030.

An Office Action dated Oct. 14, 2014, which issued during the prosecution of U.S. Appl. No. 13/319,030.

An Office Action dated Jun. 18, 2015, which issued during the prosecution of U.S. Appl. No. 13/319,030.

An Office Action dated May 3, 2016, which issued during the prosecution of U.S. Appl. No. 13/319,030.

Notice of Allowance dated Dec. 30, 2016, which issued during the prosecution of U.S. Appl. No. 13/319,030.

An Office Action dated Apr. 7, 2015, which issued during the prosecution of U.S. Appl. No. 13/319,007.

An Office Action dated Apr. 8, 2016, which issued during the prosecution of U.S. Appl. No. 14/141,228.

An Office Action dated Oct. 5, 2015, which issued during the prosecution of U.S. Appl. No. 14/246,417.

An Office Action dated Apr. 7, 2016, which issued during the prosecution of U.S. Appl. No. 14/242,151.

An Office Action dated May 23, 2016, which issued during the prosecution of U.S. Appl. No. 14/209,171.

An Office Action dated Jul. 20, 2016, which issued during the prosecution of U.S. Appl. No. 14/246,417.

An Office Action dated Jun. 14, 2016, which issued during the prosecution of U.S. Appl. No. 14/273,155.

An Office Action dated Jun. 17, 2016, which issued during the prosecution of U.S. Appl. No. 14/357,040.

An Office Action dated Mar. 24, 2015, which issued during the prosecution of U.S. Appl. No. 14/486,226.

U.S. Appl. No. 61/001,013, filed Oct. 29, 2007.

U.S. Appl. No. 61/132,295, filed Jun. 16, 2008.

U.S. Appl. No. 61/265,936, filed Dec. 2, 2009.

U.S. Appl. No. 61/283,445, filed Dec. 2, 2009.

U.S. Appl. No. 61/207,908, filed Feb. 17, 2009.

U.S. Appl. No. 61/733,979, filed Dec. 6, 2012.

U.S. Appl. No. 61/717,303, filed Oct. 23, 2012.

U.S. Appl. No. 61/820,979, filed May 8, 2013.

U.S. Appl. No. 61/745,848, filed Dec. 6, 2012.

U.S. Appl. No. 61/555,570, filed Nov. 4, 2011.

U.S. Appl. No. 61/557,082, filed Nov. 8, 2011.

(56)　　　　References Cited

OTHER PUBLICATIONS

U.S. Appl. No. 60/662,616, filed Mar. 17, 2005.
U.S. Appl. No. 60/700,542, filed Jul. 18, 2005.
U.S. Appl. No. 61/782,121, filed Mar. 14, 2013.
European Search Report dated Jul. 15, 2016, which issued during the prosecution of Applicant's European App No. 13849947.0.
European Search Report dated Nov. 4, 2015, which issued during the prosecution of European Patent Application No. EP 1077 2091.4.
Search Report in European Patent Application 10826224.7 dated Nov. 16, 2015.
Supplementary European Search Report dated Dec. 23, 2014 which issued during the prosecution of Applicant's European App No. 10834311.
Supplementary European Search Report dated Jan. 21, 2014 which issued during the prosecution of Applicant's European App No. 11 78 6226.
A Supplementary European Search Report dated Jan. 20, 2015, which issued during the prosecution of European Patent Application No. 12803037.6.
Supplementary European Search Report dated Aug. 4, 2014 which issued during the prosecution of Applicant's European App No. 11 81 1934.6.
European Search Report dated Jun. 24, 2016, which issued during the prosecution of European Patent Application No. EP 12847363.
Supplementary European Search Report dated Apr. 29, 2015, which issued during the prosecution of Applicant's European App No. 14200202.
An Office Action dated Dec. 16, 2013, which issued during the prosecution of U.S. Appl. No. 13/666,262.
An Office Action dated Dec. 18, 2013, which issued during the prosecution of U.S. Appl. No. 13/666,141.
Notice of Allowance dated Jun. 25, 2014, which issued during the prosecution of U.S. Appl. No. 13/666,262.
A Notice of Allowance dated Feb. 2, 2015, which issued during the prosecution of U.S. Appl. No. 13/504,870.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.
An Office Action dated Dec. 21, 2013, which issued during the prosecution of U.S. Appl. No. 11/908,906.
A Restriction Requirement dated Aug. 5, 2011, which issued during the prosecution of U.S. Appl. No. 11/908,906.
An Office Action dated Sep. 16, 2009 which issued during the prosecution of U.S. Appl. No. 11/950,930.
Notice of Allowance dated Sep. 12, 2014, which issued during the prosecution of U.S. Appl. No. 11/950,930.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
A Restriction Requirement dated Apr. 19, 2010 which issued during the prosecution of U.S. Appl. No. 12/341,960.
An Office Action dated Sep. 28, 2011, which issued during the prosecution of U.S. Appl. No. 12/437,103.
An Office Action dated Jun. 13, 2012, which issued during the prosecution of U.S. Appl. No. 12/437,103.
A Restriction Requirement dated Jul. 12, 2011, which issued during the prosecution of U.S. Appl. No. 12/437,103.
Notice of Allowance dated Mar. 6, 2014, which issued during the prosecution of U.S. Appl. No. 12/437,103.
Notice of Allowance dated Dec. 20, 2013, which issued during the prosecution of U.S. Appl. No. 12/437,103.
Notice of Allowance dated Apr. 27, 2012, which issued during the prosecution of U.S. Appl. No. 12/341,960.
An Office Action dated Mar. 29, 2011, which issued during the prosecution of U.S. Appl. No. 12/341,960
An Office Action dated Aug. 4, 2010, which issued during the prosecution of U.S. Appl. No. 12/341,960.

An Interview Summary dated Jul. 27, 2011, which issued during the prosecution of U.S. Appl. No. No. 12/341,960.
Notice of Allowance dated Aug. 21, 2019, which issued during the prosecution of U.S. Appl. No. 15/703,385.
Notice of Allowance dated Oct. 16, 2019, which issued during the prosecution of U.S. Appl. No. 15/703,385.
Notice of Allowance dated Dec. 24, 2020, which issued during the prosecution of U.S. Appl. No. 15/668,659.
Notice of Allowance dated Oct. 21, 2020, which issued during the prosecution of U.S. Appl. No. 15/668,659.
Declaration of Ivan Vesely, Ph.D., in Support of Petition for Inter Partesreview of U.S. Pat. No. 7,563,267—dated May 29, 2019.
U.S. Appl. No. 60/128,690, filed Apr. 9, 1999.
U.S. Appl. No. 60/613,867, filed Sep. 27, 2004.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action dated Jan. 13, 2021, which issued during the prosecution of European Patent Application No. 15751089.2.
An Office Action together with an English summary dated Mar. 3, 2021, which issued during the prosecution of Chinese Patent Application No. 201780047391.4.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. No. 10,226,341 and Exhibits 1001-1013—dated Dec. 29, 2020.
Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.
Kalbacher, D., et al. "1000 MitraClip™ procedures: Lessons learnt from the largest single-centre experience worldwide." (2019): 3137-3139.
Maisano, F., et al. "The edge-to-edge technique: a simplified method to correct mitral insufficiency." European journal of cardio-thoracic surgery 13.3 (1998): 240-246.
Fucci, C., et al. "Improved results with mitral valve repair using new surgical techniques." European journal of cardio-thoracic surgery 9.11 (1995): 621-627.
Notice of Allowance dated Nov. 19, 2019, which issued during the prosecution of U.S. Appl. No. 15/668,559.
Mitral Valve Academic Research Consortium. "Clinical Trial Design Principles and Endpoint Definitions for Transcatheter Mitral Valve Repair and Replacement: Part 1: Clinical Trial Design Principles A Consensus Document from the Mitral Valve Academic Research Consortium." Journal of the American College of Cardiology 66.3 (2015): 278-307.
An Office Action dated Aug. 29, 2018, which issued during the prosecution of U.S. Appl. No. 15/329,920.
An Office Action dated May 8, 2018, which issued during the prosecution of U.S. Appl. No. 15/902,403.
An Office Action dated May 11, 2018, which issued during the prosecution of U.S. Appl. No. 15/899,858.
Notice of Allowance dated Oct. 5, 2018, which issued during the prosecution of U.S. Appl. No. 15/886,517.
Notice of Allowance dated Jul. 19, 2019, which issued during the prosecution of U.S. Appl. No. 15/899,858.
Notice of Allowance dated Nov. 16, 2020, which issued during the prosecution of U.S. Appl. No. 16/324,339.
Notice of Allowance dated Apr. 27, 2020, which issued during the prosecution of U.S. Appl. No. 16/591,330.
An Advisory Action dated Jan. 2, 2020, which issued during the prosecution of U.S. Appl. No. 15/668,659.
Notice of Allowance dated Oct. 17, 2019, which issued during the prosecution of U.S. Appl. No. 15/329,920.
An Office Action dated Dec. 31, 2019, which issued during the prosecution of U.S. Appl. No. 16/591,330.
Notice of Allowance dated Feb. 9, 2021, which issued during the prosecution of U.S. Appl. No. 16/937,216.

(56) References Cited

OTHER PUBLICATIONS

An Advisory Action dated Nov. 18, 2020, which issued during the prosecution of U.S. Appl. No. 16/811,732.
An International Search Report and a Written Opinion both dated Mar. 27, 2018, which issued during the prosecution of Applicant's PCT/IL2017/050849.
Notice of Allowance dated Jun. 11, 2021, which issued during the prosecution of U.S. Appl. No. 16/811,732.
Notice of Allowance dated Jul. 16, 2021, which issued during the prosecution of U.S. Appl. No. 16/811,732.
Patent Trial and Appeal Board Decision Granting Institution in U.S. Pat. No. 10,226,341—Dated Jul. 20, 2021.
European Search Report dated Jun. 10, 2021 which issued during the prosecution of Applicant's European App No. 21157988.3.
Notice of Allowance dated Nov. 19, 2018, which issued during the prosecution of U.S. Appl. No. 15/197,069.
Poirier, Nancy C., et al. "A novel repair for patients with atrioventricular septal defect requiring reoperation for left atrioventricular valve regurgitation." European journal of cardio-thoracic surgery 18.1 (2000): 54-61.
An Office Action dated Mar. 29, 2021, which issued during the prosecution of U.S. Appl. No. 16/738,516.
Ando, Tomo, et al. "Iatrogenic ventricular septal defect following transcatheter aortic valve replacement: a systematic review." Heart, Lung and Circulation 25.10 (2016): 968-974.
Urena, Marina, et al. "Transseptal transcatheter mitral valve replacement using balloon-expandable transcatheter heart valves: a step-by-step approach." JACC: Cardiovascular Interventions 10.19 (2017): 1905-1919.
An English summary of an Official Action dated Mar. 29, 2021, which issued during the prosecution of Chinese Patent Application No. 201780061210.3.
An International Search Report and a Written Opinion both dated Jan. 28, 2020, which issued during the prosecution of Applicant's PCT/IL2019/051031.
An International Preliminary Report on Patentability dated Mar. 9, 2021, which issued during the prosecution of Applicant's PCT/IL2019/051031.
An Office Action dated May 4, 2021, which issued during the prosecution of U.S. Appl. No. 16/636,204.
Notice of Allowance dated May 17, 2021, which issued during the prosecution of U.S. Appl. No. 16/138,129.
Notice of Allowance dated Jun. 4, 2021, which issued during the prosecution of U.S. Appl. No. 16/802,353.
An Office Action dated May 12, 2021, which issued during the prosecution of Canadian Patent Application No. 2,973,940.
Petition for Inter Partes Review of U.S. Pat. No. 10,702,385—dated Jun. 4, 2021.
Declaration of Ivan Vesely, Ph.D. in Support of Petition for Inter Partes Review of U.S. Pat. No. 10,702,385—dated Jun. 4, 2021.
Notice of Allowance dated Oct. 30, 2018, which issued during the prosecution of U.S. Appl. No. 15/197,069.
An International Search Report and a Written Opinion both dated Jul. 12, 2021, which issued during the prosecution of Applicant's PCT/IL2021/050132.
Notice of Allowance dated Oct. 3, 2019, which issued during the prosecution of U.S. Appl. No. 15/691,032.
An Office Action dated Sep. 6, 2018, which issued during the prosecution of U.S. Appl. No. 15/213,791.
Condado, José Antonio, et al. "Percutaneous edge-to-edge mitral valve repair: 2-year follow-up in the first human case." Catheterization and cardiovascular interventions 67.2 (2006): 323-325.
Notice of Allowance dated Mar. 18, 2020, which issued during the prosecution of U.S. Appl. No. 16/284,331.
Feldman, Ted, et al. "Percutaneous mitral repair with the MitraClip system: safety and midterm durability in the initial EVEREST (Endovascular Valve Edge-to-Edge REpair Study) cohort." Journal of the American College of Cardiology 54.8 (2009): 686-694.
Notice of Allowance dated Nov. 21, 2018, which issued during the prosecution of U.S. Appl. No. 15/213,791.

Notice of Allowance dated Jul. 3, 2019, which issued during the prosecution of U.S. Appl. No. 15/691,032.
IPR2021-00383 Petitioners' Authorized Reply to Patent Owner's Preliminary Response dated May 27, 2021.
Exhibit 1014—Transcript of proceedings held May 20, 2021 (*Edwards Lifesciences* vs. *Cardiovalve*).
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021(*Edwards Lifesciences* vs. *Cardiovalve*).
An Invitation to pay additional fees dated May 19, 2021, which issued during the prosecution of Applicant's PCT/IL2021/050132.
An Office Action dated Aug. 18, 2021, which issued during the prosecution of U.S. Appl. No. 17/210,183.
An Office Action dated Sep. 9, 2021, which issued during the prosecution of U.S. Appl. No. 16/768,909.
An Office Action dated Sep. 15, 2021, which issued during the prosecution of U.S. Appl. No. 16/135,599.
Notice of Allowance dated Oct. 14, 2021, which issued during the prosecution of U.S. Appl. No. 16/680,739.
An Office Action dated Oct. 21, 2021, which issued during the prosecution of U.S. Appl. No. 17/335,845.
European Search Report dated Oct. 11, 2021 which issued during the prosecution of Applicant's European App No. 21176010.3.
Fann, James I., et al. "Beating heart catheter-based edge-to-edge mitral valve procedure in a porcine model: efficacy and healing response." Circulation 110.8 (2004): 988-993.
IPR2021-00383 Patent Owner's Contingent Motion to Amend Under 37 C.F.R. §42.121 dated Oct. 13, 2021.
IPR2021-00383 Patent Owner's Response Pursuant to 37 C.F.R. § 42.120 dated Oct. 13, 2021.
IPR2021-00383 Second Declaration of Dr. Michael Sacks dated Oct. 13, 2021.
An Office Action dated Oct. 21, 2021, which issued during the prosecution of U.S. Appl. No. 17/306,231.
Maisano, Francesco, et al. "The evolution from surgery to percutaneous mitral valve interventions: the role of the edge-to-edge technique." Journal of the American College of Cardiology 58.21 (2011): 2174-2182.
An Office Action dated Nov. 6, 2015, which issued during the prosecution of U.S. Appl. No. 14/626,267.
An Office Action dated Jan. 26, 2022, which issued during the prosecution of U.S. Appl. No. 16/888,210.
IPR2021-00383 Deposition of Dr. Ivan Vesely, dated Sep. 22, 2021.
Cardiovalve Exhibit 2009—Percutaneous Mitral Leaflet Repair: MitraClip® Therapy for Mitral Regurgitation (2012).
Feldman, Ted, et al. "Percutaneous mitral valve repair using the edge-to-edge technique: six-month results of the EVEREST Phase I Clinical Trial." Journal of the American College of Cardiology 46.11 (2005): 2134-2140.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
An Office Action summarized English translation and Search Report dated Aug. 12, 2021, which issued during the prosecution of Chinese Patent Application No. 201880058940.2.
U.S. Appl. No. 63/120,808, filed Dec. 3, 2020.
An Office Action dated Nov. 25, 2021, which issued during the prosecution of European Patent Application No. 18826823.9.
An Office Action dated Oct. 4, 2023, which issued during the prosecution of Canadian Patent Application No. 3,031,187.
IPR2021-01051 Institution decision dated Dec. 10, 2021.
Notice of Allowance dated Dec. 7, 2021, which issued during the prosecution of U.S. Appl. No. 17/394,807.
Notice of Allowance dated Dec. 6, 2021, which issued during the prosecution of U.S. Appl. No. 16/738,516.
Notice of Allowance dated Dec. 29, 2021, which issued during the prosecution of U.S. Appl. No. 17/210,183.
IPR2021-00383 Petitioners' Reply to Patent Owner's Response dated Jan. 5, 2022.

(56) References Cited

OTHER PUBLICATIONS

IPR2021-00383 Petitioners' Opposition to Patent Owner's Contingent Motion to Amend dated Jan. 5, 2022.
An Office Action dated Sep. 22, 2021, which issued during the prosecution of European Patent Application No. 20714289.4.
Summary of Examination Notice dated Jan. 6, 2022, which issued during the prosecution of Chinese Patent Application No. 201880064313. X.
An Office Action dated Jan. 12, 2022, which issued during the prosecution of U.S. Appl. No. 17/101,787.
Notice of Allowance dated Jun. 20, 2017, which issued during the prosecution of U.S. Appl. No. 14/626,267.
Notice of Allowance dated Oct. 20, 2021, which issued during the prosecution of U.S. Appl. No. 16/636,204.
Notice of Allowance dated Jan. 31, 2022, which issued during the prosecution of U.S. Appl. No. 17/479,418.
An Office Action dated Jan. 13, 2022, which issued during the prosecution of U.S. Appl. No. 17/473,472.
An Office Action dated Apr. 11, 2022, which issued during the prosecution of U.S. Appl. No. 17/473,472.
IPR2021-00383 Preliminary Guidance dated Jan. 31, 2022.
An Office Action dated Mar. 18, 2022, which issued during the prosecution of U.S. Appl. No. 16/746,489.
Notice of Allowance dated Mar. 22, 2022, which issued during the prosecution of U.S. Appl. No. 17/366,711.
Notice of Allowance dated Mar. 4, 2022, which issued during the prosecution of U.S. Appl. No. 16/768,909.
An Office Action dated Dec. 9, 2021, which issued during the prosecution of U.S. Appl. No. 16/135,969.
An Office Action dated Jan. 24, 2022, which issued during the prosecution of U.S. Appl. No. 16/135,466.
An Office Action dated Nov. 3, 2023, which issued during the prosecution of Canadian Patent Application No. 3,162,308.
Notice of Allowance dated Jul. 6, 2023, which issued during the prosecution of U.S. Appl. No. 17/004,693.
Notice of Allowance dated Jul. 13, 2023, which issued during the prosecution of U.S. Appl. No. 17/004,693.
Notice of Allowance dated Jul. 10, 2023, which issued during the prosecution of U.S. Appl. No. 17/007,975.
Notice of Allowance dated Mar. 13, 2024, which issued during the prosecution of U.S. Appl. No. 18/216,391.
IPR2021-01051 Preliminary Guidance Patent Owner's Motion to Amend dated Jun. 24, 2022.
Ex Parte Quayle dated May 2, 2022, which issued during the prosecution of U.S. Appl. No. 16/879,952.
An International Search Report and a Written Opinion both dated May 3, 2022, which issued during the prosecution of Applicant's PCT/IL2021/051433.
An Office Action together with an English Summary dated May 7, 2022 which issued during the prosecution of Chinese Patent Application No. 201880058940.2.
Notice of Allowance dated May 4, 2022, which issued during the prosecution of U.S. Appl. No. 16/680,739.
An Office Action dated Jun. 28, 2022, which issued during the prosecution of U.S. Appl. No. 16/135,969.
An Office Action dated Jul. 8, 2022, which issued during the prosecution of U.S. Appl. No. 16/144,054.
Notice of Allowance dated May 1, 2023, which issued during the prosecution of U.S. Appl. No. 17/007,975.
An Office Action dated Jul. 27, 2022, which issued during the prosecution of U.S. Appl. No. 16/881,350.
An Office Action dated Sep. 21, 2022, which issued during the prosecution of U.S. Appl. No. 16/776,581.
An Office Action dated Jul. 20, 2022, which issued during the prosecution of U.S. Appl. No. 17/101,787.
An Office Action dated Sep. 16, 2022, which issued during the prosecution of U.S. Appl. No. 16/135,466.
An Office Action dated Aug. 1, 2022, which issued during the prosecution of European Patent Application No. 18826823.9.

European Search Report dated Sep. 6, 2022 which issued during the prosecution of Applicant's European App No. 22161862.2.
IPR2021-01051 Petitioners' Reply to Preliminary Guidance dated Aug. 2, 2022.
IPR2021-01051 Patent Owner's Sur-Reply to Petitioners' Reply to Preliminary Guidance dated Aug. 23, 2022.
An Office Action dated Aug. 5, 2022, which issued during the prosecution of U.S. Appl. No. 16/760,147.
An Office Action dated Sep. 8, 2022, which issued during the prosecution of U.S. Appl. No. 16/896,858.
An Office Action dated Nov. 10, 2022, which issued during the prosecution of U.S. Appl. No. 17/007,975.
An Office Action dated Sep. 29, 2022, which issued during the prosecution of U.S. Appl. No. 17/010,886.
An Office Action dated Sep. 29, 2022, which issued during the prosecution of U.S. Appl. No. 16/656,790.
An Office Action dated Nov. 2, 2022, which issued during the prosecution of U.S. Appl. No. 17/004,693.
An Office Action dated Nov. 28, 2022, which issued during the prosecution of U.S. Appl. No. 17/141,853.
An Office Action dated Oct. 19, 2022, which issued during the prosecution of U.S. Appl. No. 17/875,589.
An Office Action dated Oct. 26, 2022, which issued during the prosecution of U.S. Appl. No. 16/746,489.
An International Preliminary Report on Patentability dated May 30, 2023, which issued during the prosecution of Applicant's PCT/IL2021/051433.
Notice of Allowance dated Dec. 21, 2022, which issued during the prosecution of U.S. Appl. No. 17/101,787.
Notice of Allowance dated Oct. 5, 2022, which issued during the prosecution of U.S. Appl. No. 17/101,787.
An Office Action dated Mar. 3, 2023, which issued during the prosecution of European Patent Application No. 17751143.3.
An Office Action dated Mar. 20, 2023, which issued during the prosecution of U.S. Appl. No. 17/181,722.
Notice of Allowance dated Dec. 4, 2023, which issued during the prosecution of U.S. Appl. No. 17/683,875.
European Search Report dated Mar. 20, 2023 which issued during the prosecution of Applicant's European App No. 22204764.9.
Notice of Allowance dated Apr. 6, 2023, which issued during the prosecution of U.S. Appl. No. 16/746,489.
An Office Action dated Apr. 14, 2023, which issued during the prosecution of U.S. Appl. No. 16/144,054.
An Office Action dated May 15, 2023, which issued during the prosecution of U.S. Appl. No. 16/656,790.
An Office Action dated May 16, 2023, which issued during the prosecution of U.S. Appl. No. 17/114,771.
An Office Action dated May 17, 2023, which issued during the prosecution of U.S. Appl. No. 17/466,785.
An Office Action dated May 25, 2023, which issued during the prosecution of U.S. Appl. No. 17/397,235.
Notice of Allowance dated Sep. 20, 2023, which issued during the prosecution of U.S. Appl. No. 17/839,538.
An Office Action dated Oct. 13, 2023, which issued during the prosecution of U.S. Appl. No. 17/181,722.
Grounds of Opposition to European Patent No. EP 2 948 103, filed Sep. 6, 2023.
An Office Action dated Aug. 31, 2023, which issued during the prosecution of U.S. Appl. No. 17/397,235.
An Office Action dated Sep. 8, 2023, which issued during the prosecution of U.S. Appl. No. 18/216,391.
An Office Action dated Sep. 8, 2023, which issued during the prosecution of U.S. Appl. No. 18/218,419.
An Office Action summarized English translation and Search Report dated Sep. 22, 2022, which issued during the prosecution of Chinese Patent Application No. 201880058940.2.
An Office Action dated Jul. 24, 2024, which issued during the prosecution of U.S. Appl. No. 18/234,745.
Opposition to European Patent No. EP 2 948 103, filed Sep. 6, 2023.
An International Search Report and a Written Opinion both dated Aug. 23, 2023, 2023, which issued during the prosecution of Applicant's PCT/IL2023/050586.

(56) References Cited

OTHER PUBLICATIONS

An Office Action dated Aug. 3, 2023, which issued during the prosecution of U.S. Appl. No. 17/683,875.
An International Search Report and a Written Opinion both dated Sep. 13, 2023, which issued during the prosecution of Applicant's PCT/IL2023/050587.
An Invitation to pay additional fees dated Mar. 14, 2019, which issued during the prosecution of Applicant's PCT/IL2018/0051350.
An International Preliminary Report on Patentability dated Jun. 16, 2020, which issued during the prosecution of Applicant's PCT/IL2018/0051350.
Notice of Allowance dated Nov. 12, 2020, which issued during the prosecution of U.S. Appl. No. 16/269,328.
An Advisory Action dated Apr. 9, 2019, which issued during the prosecution of U.S. Appl. No. 15/970,314.
An Advisory Action dated Mar. 13, 2019, which issued during the prosecution of U.S. Appl. No. 15/979,686.
An Advisory Action dated Jul. 8, 2019, which issued during the prosecution of U.S. Appl. No. 15/995,725.
An Office Action dated Nov. 16, 2018, which issued during the prosecution of U.S. Appl. No. 16/042,129.
An Office Action dated Jul. 22, 2020, which issued during the prosecution of U.S. Appl. No. 16/135,447.
An Advisory Action dated Jan. 2, 2020, which issued during the prosecution of U.S. Appl. No. 16/041,208.
IPR2021-00383 Final Written Decision Determining All Challenged Claims Unpatentable Denying Patent Owner's Contingent Motion to Amend Granting-in-Part and Denying-in-Part Petitioner's Motion to Strike Denying Patent Owner's Motion to Exclude dated Jul. 18, 2022.
Notice of Allowance dated May 6, 2020, which issued during the prosecution of U.S. Appl. No. 16/730,090.
Notice of Allowance dated Feb. 2, 2022, which issued during the prosecution of U.S. Appl. No. 16/135,663.
Notice of Allowance dated Feb. 16, 2022, which issued during the prosecution of U.S. Appl. No. 16/135,663.
Notice of Allowance dated Sep. 16, 2020, which issued during the prosecution of U.S. Appl. No. 16/135,770.
Notice of Allowance dated Oct. 22, 2019, which issued during the prosecution of U.S. Appl. No. 15/433,547.
Notice of Allowance dated May 19, 2021, which issued during the prosecution of U.S. Appl. No. 16/135,619.
U.S. Appl. No. 62/295,701, filed Feb. 16, 2016.
An Office Action dated May 15, 2013, which issued during the prosecution of U.S. Appl. No. 12/583,979.
Notice of Allowance dated Oct. 15, 2020, which issued during the prosecution of U.S. Appl. No. 16/740,659.
Notice of Allowance dated Apr. 30, 2020, which issued during the prosecution of U.S. Appl. No. 15/970,314.
Notice of Allowance dated Feb. 28, 2022, which issued during the prosecution of U.S. Appl. No. 16/135,599.
Notice of Allowance dated Jan. 10, 2022, which issued during the prosecution of U.S. Appl. No. 16/135,599.
Notice of Allowance dated May 26, 2021, which issued during the prosecution of U.S. Appl. No. 16/135,599.
Notice of Allowance dated Feb. 2, 2022, which issued during the prosecution of U.S. Appl. No. 16/135,619.
Notice of Allowance dated Feb. 15, 2022, which issued during the prosecution of U.S. Appl. No. 16/135,619.
Notice of Allowance dated May 12, 2021, which issued during the prosecution of U.S. Appl. No. 16/135,619.
Advisory Action dated Feb. 3, 2021, which issued during the prosecution of U.S. Appl. No. 16/135,505.
An Office Action dated Sep. 8, 2020, which issued during the prosecution of U.S. Appl. No. 16/136,074.
An Office Action dated Jan. 25, 2021, which issued during the prosecution of U.S. Appl. No. 16/136,082.
An Office Action dated Jun. 1, 2020, which issued during the prosecution of U.S. Appl. No. 16/136,082.
An Office Action dated Mar. 16, 2020, which issued during the prosecution of U.S. Appl. No. 16/136,110.
An Office Action dated Mar. 12, 2020, which issued during the prosecution of U.S. Appl. No. 16/136,123.
An Office Action dated Mar. 10, 2020, which issued during the prosecution of U.S. Appl. No. 16/136,150.
An Office Action dated Apr. 7, 2020, which issued during the prosecution of U.S. Appl. No. 16/520,289.
An Office Action dated Jan. 14, 2021, which issued during the prosecution of U.S. Appl. No. 16/135,969.
An Office Action dated May 28, 2021, which issued during the prosecution of U.S. Appl. No. 16/135,969.
An Office Action dated Sep. 9, 2020, which issued during the prosecution of U.S. Appl. No. 16/135,969.
An Office Action dated Mar. 20, 2020, which issued during the prosecution of U.S. Appl. No. 16/135,979.
An Office Action dated Oct. 20, 2020, which issued during the prosecution of U.S. Appl. No. 16/135,979.
An Office Action dated Mar. 6, 2020, which issued during the prosecution of U.S. Appl. No. 16/136,074.
An Office Action dated Mar. 19, 2021, which issued during the prosecution of U.S. Appl. No. 16/136,074.
An Office Action dated Aug. 11, 2020, which issued during the prosecution of U.S. Appl. No. 16/135,619.
An Office Action dated Dec. 21, 2020, which issued during the prosecution of U.S. Appl. No. 16/135,619.
An Office Action dated Apr. 10, 2020, which issued during the prosecution of U.S. Appl. No. 16/135,663.
An Office Action dated Jun. 28, 2021, which issued during the prosecution of U.S. Appl. No. 16/135,663.
An Office Action dated Mar. 8, 2021, which issued during the prosecution of U.S. Appl. No. 16/135,663.
An Office Action dated Sep. 23, 2020, which issued during the prosecution of U.S. Appl. No. 16/135,663.
An Office Action dated Mar. 16, 2020, which issued during the prosecution of U.S. Appl. No. 16/135,770.
An Office Action dated Dec. 10, 2020, which issued during the prosecution of U.S. Appl. No. 16/135,599.
An Office Action dated Jun. 1, 2020, which issued during the prosecution of U.S. Appl. No. 16/135,599.
An Office Action dated Mar. 5, 2020, which issued during the prosecution of U.S. Appl. No. 16/135,843.
An Office Action dated Apr. 9, 2020, which issued during the prosecution of U.S. Appl. No. 16/135,969.
Notice of Allowance dated Feb. 4, 2022, which issued during the prosecution of U.S. Appl. No. 16/135,447.
Notice of Allowance dated Mar. 24, 2022, which issued during the prosecution of U.S. Appl. No. 16/135,447.
Notice of Allowance dated Mar. 14, 2022, which issued during the prosecution of U.S. Appl. No. 16/135,505.
Notice of Allowance dated Mar. 16, 2021, which issued during the prosecution of U.S. Appl. No. 16/135,505.
Notice of Allowance dated Jun. 15, 2020, which issued during the prosecution of U.S. Appl. No. 16/135,843.
Notice of Allowance dated Jun. 23, 2020, which issued during the prosecution of U.S. Appl. No. 16/135,843.
Notice of Allowance dated Aug. 24, 2021, which issued during the prosecution of U.S. Appl. No. 16/135,979.
Notice of Allowance dated Dec. 24, 2021, which issued during the prosecution of U.S. Appl. No. 16/135,979.
Notice of Allowance dated Feb. 22, 2022, which issued during the prosecution of U.S. Appl. No. 16/135,979.
Notice of Allowance dated Mar. 17, 2021, which issued during the prosecution of U.S. Appl. No. 16/135,979.
Notice of Allowance dated Feb. 8, 2022, which issued during the prosecution of U.S. Appl. No. 16/136,074.
An Office Action dated Oct. 25, 2023, which issued during the prosecution of U.S. Appl. No. 16/144,054.
An Office Action dated Sep. 29, 2023, which issued during the prosecution of Chinese Patent Application No. 201880076340.9.
Notice of Allowance dated Jun. 27, 2019, which issued during the prosecution of U.S. Appl. No. 16/042,028.

(56)          References Cited

OTHER PUBLICATIONS

Notice of Allowance dated Jul. 3, 2019, which issued during the prosecution of U.S. Appl. No. 16/042,129.
Notice of Allowance dated Feb. 16, 2022, which issued during the prosecution of U.S. Appl. No. 16/136,074.
Notice of Allowance dated Jul. 30, 2021, which issued during the prosecution of U.S. Appl. No. 16/136,074.
Notice of Allowance dated Jul. Sep. 24, 2021, which issued during the prosecution of U.S. Appl. No. 16/136,074.
Notice of Allowance dated Dec. 23, 2021, which issued during the prosecution of U.S. Appl. No. 16/136,082.
Notice of Allowance dated Feb. 28, 2022, which issued during the prosecution of U.S. Appl. No. 16/136,082.
Advisory Action dated Jan. 14, 2021, which issued during the prosecution of U.S. Appl. No. 16/135,663.
Advisory Action dated Dec. 15, 2020, which issued during the prosecution of U.S. Appl. No. 16/135,969.
Advisory Action dated Jul. 14, 2020, which issued during the prosecution of U.S. Appl. No. 16/520,289.
Notice of Allowance dated Mar. 8, 2019, which issued during the prosecution of U.S. Appl. No. 15/978,494.
Notice of Allowance dated May 22, 2019, which issued during the prosecution of U.S. Appl. No. 15/979,686.
Notice of Allowance dated Apr. 11, 2019, which issued during the prosecution of U.S. Appl. No. 15/994,022.
Notice of Allowance dated Feb. 12, 2020, which issued during the prosecution of U.S. Appl. No. 15/995,725.
Notice of Allowance dated Aug. 26, 2020, which issued during the prosecution of U.S. Appl. No. 16/136,150.
Notice of Allowance dated Dec. 10, 2020, which issued during the prosecution of U.S. Appl. No. 16/136,150.
Notice of Allowance dated Aug. 22, 2019, which issued during the prosecution of U.S. Appl. No. 16/507,357.
Notice of Allowance dated Dec. 11, 2019, which issued during the prosecution of U.S. Appl. No. 16/507,357.
Notice of Allowance dated Dec. 16, 2020, which issued during the prosecution of U.S. Appl. No. 16/520,289.
Notice of Allowance dated Sep. 17, 2020, which issued during the prosecution of U.S. Appl. No. 16/520,289.
Notice of Allowance dated Mar. 25, 2020, which issued during the prosecution of U.S. Appl. No. 16/559,365.
An Office Action dated Oct. 7, 2019, which issued during the prosecution of U.S. Appl. No. 16/520,289.
An Office Action dated Oct. 23, 2019, which issued during the prosecution of U.S. Appl. No. 16/559,365.
An Office Action dated Dec. 12, 2019, which issued during the prosecution of U.S. Appl. No. 16/585,349.
An Office Action dated Jul. 16, 2020, which issued during the prosecution of U.S. Appl. No. 16/678,355.
An Office Action dated Mar. 18, 2020, which issued during the prosecution of U.S. Appl. No. 16/740,659.
Notice of Allowance dated Aug. 11, 2020, which issued during the prosecution of U.S. Appl. No. 16/136,110.
Notice of Allowance dated Sep. 30, 2020, which issued during the prosecution of U.S. Appl. No. 16/136,123.
Notice of Allowance dated May 1, 2020, which issued during the prosecution of U.S. Appl. No. 15/995,725.
Notice of Allowance dated Aug. 1, 2019, which issued during the prosecution of U.S. Appl. No. 16/008,618.
Notice of Allowance dated Nov. 13, 2019, which issued during the prosecution of U.S. Appl. No. 16/008,618.
Notice of Allowance dated Aug. 28, 2019, which issued during the prosecution of U.S. Appl. No. 16/040,831.
Notice of Allowance dated Dec. 10, 2019, which issued during the prosecution of U.S. Appl. No. 16/040,831.
Notice of Allowance dated Jan. 23, 2020, which issued during the prosecution of U.S. Appl. No. 16/041,208.
Notice of Allowance dated Mar. 5, 2020, which issued during the prosecution of U.S. Appl. No. 16/041,208.

Notice of Allowance dated May 6, 2020, which issued during the prosecution of U.S. Appl. No. 16/041,208.
An Office Action dated Apr. 19, 2019, which issued during the prosecution of U.S. Appl. No. 15/008,618.
An Office Action dated Feb. 14, 2019, which issued during the prosecution of U.S. Appl. No. 15/008,618.
An Office Action dated Jun. 19, 2019, which issued during the prosecution of U.S. Appl. No. 15/040,831.
An Office Action dated Sep. 30, 2021, which issued during the prosecution of U.S. Appl. No. 16/135,447.
An Office Action dated Mar. 10, 2021, which issued during the prosecution of U.S. Appl. No. 16/135,447.
An Office Action dated Aug. 15, 2019, which issued during the prosecution of U.S. Appl. No. 16/041,208.
An Office Action dated Jun. 21, 2021, which issued during the prosecution of U.S. Appl. No. 16/135,447.
An Office Action dated Apr. 3, 2020, which issued during the prosecution of U.S. Appl. No. 16/135,466.
An Office Action dated Mar. 27, 2020, which issued during the prosecution of U.S. Appl. No. 16/135,505.
An Office Action dated Sep. 8, 2021, which issued during the prosecution of U.S. Appl. No. 16/135,505.
An Office Action dated Sep. 29, 2020, which issued during the prosecution of U.S. Appl. No. 16/135,505.
An Office Action dated Dec. 21, 2018, which issued during the prosecution of U.S. Appl. No. 15/978,494.
An Office Action dated Dec. 28, 2018, which issued during the prosecution of U.S. Appl. No. 15/979,686.
An Office Action dated Feb. 12, 2019, which issued during the prosecution of U.S. Appl. No. 15/994,022.
An Office Action dated Feb. 13, 2019, which issued during the prosecution of U.S. Appl. No. 15/995,725.
An Office Action dated Oct. 22, 2019, which issued during the prosecution of U.S. Appl. No. 15/995,725.
An Office Action dated Jun. 20, 2019, which issued during the prosecution of U.S. Appl. No. 15/970,314.
An Office Action dated Nov. 21, 2019, which issued during the prosecution of U.S. Appl. No. 15/970,314.
An Office Action dated Feb. 22, 2024, which issued during the prosecution of Canadian Patent Application No. 3,096,002.
An Office Action dated Jan. 26, 2024, which issued during the prosecution of Chinese Patent Application No. 201980023291.7.
Notice of Allowance dated Sep. 27, 2023, which issued during the prosecution of U.S. Appl. No. 17/010,886.
Notice of Allowance dated Apr. 10, 2024, which issued during the prosecution of U.S. Appl. No. 17/010,886.
An Office Action dated Apr. 25, 2024, which issued during the prosecution of U.S. Appl. No. 17/397,235.
An Office Action dated Mar. 25, 2024, which issued during the prosecution of U.S. Appl. No. 17/841,912.
An International Search Report and a Written Opinion both dated Oct. 18, 2022, which issued during the prosecution of PCT/US2022/037864.
European Search Report dated Nov. 14, 2023 which issued during the prosecution of Applicant's European App No. 23191562.0.
An Office Action dated Jan. 25, 2024, which issued during the prosecution of U.S. Appl. No. 18/090,058.
Notice of Allowance dated Nov. 8, 2023, which issued during the prosecution of U.S. Appl. No. 16/656,790.
An Office Action dated Oct. 20, 2023, which issued during the prosecution of Canadian Patent Application No. 3,170,042.
An Office Action dated Dec. 19, 2023, which issued during the prosecution of U.S. Appl. No. 17/010,886.
An Office Action dated Dec. 22, 2023, which issued during the prosecution of U.S. Appl. No. 18/216,391.
An International Search Report and a Written Opinion both dated Jan. 18, 2024, which issued during the prosecution of Applicant's PCT/IL2023/050958.
Notice of Allowance dated May 6, 2020, which issued during the prosecution of U.S. Appl. No. 16/559,365.
Notice of Allowance dated Jul. 23, 2020, which issued during the prosecution of U.S. Appl. No. 16/585,349.

(56)                 References Cited

OTHER PUBLICATIONS

Notice of Allowance dated Nov. 2, 2020, which issued during the prosecution of U.S. Appl. No. 16/585,349.

Notice of Allowance dated Aug. 5, 2020, which issued during the prosecution of U.S. Appl. No. 16/660,231.

Notice of Allowance dated Nov. 18, 2020, which issued during the prosecution of U.S. Appl. No. 16/660,231.

Notice of Allowance dated Dec. 7, 2020, which issued during the prosecution of U.S. Appl. No. 16/678,355.

Notice of Allowance dated Feb. 24, 2020, which issued during the prosecution of U.S. Appl. No. 16/730,090.

Notice of Allowance dated Apr. 10, 2024, which issued during the prosecution of U.S. Appl. No. 17/181,722.

Summons to Attend Oral Proceedings regarding European Patent Application No. 22161862.2, dated Feb. 26, 2024.

A Letter from the opponent regarding European Patent Application No. 14710060.6, dated Apr. 5, 2024.

Summons to Attend Oral Proceedings regarding European Patent Application No. 14710060.6, dated May 10, 2024.

A Brief Communication together with a Letter from the opponent regarding European Patent Application No. 14710060.6, dated Apr. 12, 2024.

An Office Action dated Jun. 18, 2024, which issued during the prosecution of U.S. Appl. No. 17/399,594.

An Office Action dated Aug. 9, 2024, which issued during the prosecution of Chinese Patent Application No. 202210336863.0.

An Office Action dated Aug. 1, 2024, which issued during the prosecution of U.S. Appl. No. 18/368,250.

An Office Action dated Jul. 3, 2024, which issued during the prosecution of U.S. Appl. No. 18/109,937.

226,226p

216

20,22

20,22

230

232

220

210,214

226,226d

200

244

MINIMALLY-INVASIVE DELIVERY SYSTEMS

CROSS-REFERENCES TO RELATED APPLICATIONS

The present application is a Continuation application of U.S. patent application Ser. No. 17/181,722 to Hariton et al., filed Feb. 22, 2021, and entitled, "Minimally-invasive delivery systems." which published as US 2021/0196461 and which is a Continuation application of U.S. patent application Ser. No. 16/318,025 to Hariton et al., filed Jan. 15, 2019, and entitled, "Minimally-invasive delivery systems" (now U.S. Pat. No. 10,952,850), which is the US National Phase of PCT application PCT/IL2017/050849 to Hariton et al., filed Aug. 1, 2017, and entitled, "Minimally-invasive delivery systems," which published as WO 2018/025263, and which claims priority from UK patent application GB1613219.3, filed Aug. 1, 2016, and entitled "Minimally-invasive delivery systems."

All of the above applications are incorporated herein by reference.

FIELD OF THE INVENTION

Some applications of the present invention relate in general to valve replacement. More specifically, some applications of the present invention relate to prosthetic cardiac valves and techniques for implantation thereof.

BACKGROUND

Dilation of the annulus of a heart valve, such as that caused by ischemic heart disease, prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

Systems are described, each of which comprises a delivery tool for an implant, the delivery tool comprising a balloon at a distal portion of the tool. The balloon facilitates movement of the distal portion of the tool past potential anatomical and/or implanted obstacles, e.g., by providing a tapered surface. One described balloon serves as a nosecone of the delivery tool, facilitating distal movement of the distal portion of the tool through the vasculature. Another described balloon serves as a reverse nosecone that facilitates proximal movement of the distal portion of the tool through the implanted implant.

Also described is a sheath for retaining the implant on the distal portion of a delivery tool, and a system for unsheathing the implant.

Also described is a delivery tool that comprises a housing that defines a generally-helical track, and a controller that comprises an actuator. At least part of an implant is housed by the housing. Rotation of the actuator draws the housing proximally with respect to the implant by sliding an engaging element of the actuator along the track. This proximal movement of the housing deploys the implant from within the housing.

The technologies described may be used separately on different delivery tools, or in various combinations on a single delivery tool.

There is therefore provided, in accordance with an application of the present invention, apparatus, for use with an implant, the apparatus including a tool, the tool including:

a housing, at a distal part of the tool, the housing:

including a tubular wall that circumscribes a longitudinal axis of the distal part of the tool, dimensioned to house at least part of the implant, and defining a track that follows a generally-helical path around the longitudinal axis; and a controller, including:

a rod that extends from a proximal part of the tool to the housing; and an actuator, fixedly coupled to the rod, including an engaging element that engages the track, and rotatable with respect to the housing, the controller and the housing mechanically cooperating such that rotation of the actuator with respect to the housing slides the housing longitudinally with respect to the actuator.

In an Application:

the housing is a proximal housing, and the part of the implant is a first part of the implant;

the proximal housing is configured to house the first part of the implant, and has a distal opening for deployment of the first part of the implant therethrough; and the tool further includes a distal housing that is configured to house a second part of the implant, and has a proximal opening for deployment of the second part of the implant therethrough, the proximal opening of the distal housing facing the distal opening of the proximal housing.

In an application, the housing is dimensioned to house at least the part of the implant such that at least the part of the implant is coincident along the longitudinal axis with at least part of the track.

In an application, the housing is dimensioned to house at least the part of the implant such that the generally-helical path around the longitudinal axis is also around at least the part of the implant, and at least part of the track follows the generally-helical path around the longitudinal axis and at least the part of the implant.

In an Application:

the tool further includes a catheter, the rod extends through the catheter, the controller and the housing mechanically cooperate such that rotation of the actuator with respect to the housing slides the housing proximally along and over part of the catheter.

In an application, the controller and the housing mechanically cooperate such that rotation of the actuator in a first direction with respect to the housing slides the housing proximally with respect to the actuator, and rotation of the actuator in a second, opposite direction with respect to the housing slides the housing distally with respect to the actuator.

In an application, the track is a first track, and the housing further includes a second track that follows a generally-linear path parallel to the longitudinal axis.

In an application, the track is a channel, and the engaging element is a spur that engages the track by protruding into the channel.

In an application, the track is a rail, and the engaging element is a notch that engages the track by receiving the rail.

In an Application:

a first portion of the generally-helical path has a first pitch,

a second portion of the generally-helical path has a second pitch, the second portion being distal to the first portion, and the second pitch being greater than the first pitch, and the track follows the generally-helical path that has the first portion that has the first pitch and the second portion that has the second pitch.

In an Application:

the generally-helical path has a pitch that is progressively greater at progressively distal portions of the generally-helical path, and the track follows the generally-helical path that has the pitch that is progressively greater at progressively distal portions of the generally-helical path.

In an application, the apparatus further includes the implant.

In an application, the apparatus further includes a shaft to which the implant is fixable, the shaft being slidably coupled to the housing, and extending proximally from the housing.

In an Application:

the track is a first track, the engaging element is a first engaging element, the housing further includes a second track that follows a generally-linear path parallel to the longitudinal axis, the tool further includes a second engaging element, fixedly coupled to the shaft, the second engaging element engaging the second track such that the shaft is rotationally fixed with respect to the housing.

In an application, the controller and the housing mechanically cooperate such that rotation of the actuator with respect to the housing slides the second track longitudinally with respect to the second engaging element.

In an application, the apparatus further includes the implant, fixedly coupled to the shaft, at least the part of the implant housed by the housing.

In an application, the rod is coaxial with the shaft.

In an application, the shaft is disposed within the rod.

In an application, the actuator defines a hole through which the shaft extends.

In an application, the shaft is rotationally fixed with respect to the housing.

In an application, at least part of the shaft is disposed within the housing.

There is further provided, in accordance with an application of the present invention, a method, including:

transluminally advancing, into a heart of a subject, a distal part of a tool, the distal part of the tool including a housing, the housing:

including a tubular wall that circumscribes a longitudinal axis of the distal part of the tool, housing at least part of an implant, and defining a track that follows a generally-helical path around the longitudinal axis; and retracting the housing from at least the part of the implant by rotating a rod that is fixedly coupled to an actuator that includes an engaging element that is engaged with the track, such that the actuator rotates with respect to the housing and causes the housing to slide longitudinally with respect to the actuator.

There is further provided, in accordance with an application of the present invention, apparatus, including:

an implant; and a tool, configured for transluminal delivery of the implant, the tool having a proximal part and a distal part, and including:

a shaft that extends longitudinally from the proximal part of the tool to the distal part of the tool;

a nosepiece, fixed to the shaft, and arranged with respect to the implant such that the implant extends proximally away from the nosepiece and over the shaft;

a sheath, configured to house the implant during transluminal delivery, and having a diameter that is dimensioned for transluminal delivery; and a balloon, disposed at the distal part of the tool, and in fluid communication with the proximal part of the tool, And the Balloon has:

a maximally-inflated state in which the balloon (i) has a widest part that has an inflated diameter that is less than the diameter of the sheath or at most 10 percent greater than the diameter of the sheath, and (ii) has a tapered portion that tapers longitudinally away from the widest part and from the nosepiece, and a deflated state in which the widest part has a deflated diameter that is smaller than the inflated diameter.

In an application, the nosepiece is fixed to the distal end of the shaft.

In an application, the tapered portion tapers distally away from the widest part and from the nosepiece.

In an application, the tapered portion tapers proximally away from the widest part and from the nosepiece.

In an application, the apparatus has a delivery state in which the implant, the sheath, and the balloon are transluminally advanceable into a subject, and in which:

the implant is in a compressed state, and is housed by the sheath, and the balloon is in its maximally-inflated state.

In an application, the apparatus has a delivery state in which the implant, the sheath, and the balloon are transluminally advanceable into a subject, and in which:

the implant is in a compressed state, and is housed by the sheath, and the balloon is in its deflated state.

In an application, the balloon is slidably coupled to the shaft at least in the deflated state of the balloon.

In an Application:

the implant (i) is constrainable, by a constraining force, in a compressed state in which the implant has a compressed diameter, and (ii) has an expanded state into which the implant automatically transitions upon removal of the constraining force, and in which the implant has an expanded diameter, and the maximally-inflated diameter of the balloon is smaller than the expanded diameter of the implant.

In an Application:

the implant is shaped to define a lumen therethrough, the nosepiece is arranged with respect to the implant such that the implant extends proximally over the shaft with the shaft within the lumen of the implant, the implant has an expanded state, and assumes the expanded state upon implantation of the implant, and the nosepiece is dimensioned to be withdrawable proximally through the lumen while the implant is in its expanded state.

In an application, the implant is self-expanding to the expanded state.

In an application, the implant has a compressed state for transluminal delivery, and the nosepiece is not dimensioned to be withdrawable proximally through the lumen while the implant is in its compressed state.

There is further provided, in accordance with an application of the present invention, apparatus, including:

an implant:

constrainable, by a constraining force, in a compressed
state in which the implant has a compressed diam-
eter,
having an expanded state into which the implant auto-
matically transitions upon removal of the constrain-
ing force, and in which the implant has an expanded
diameter; and
a tool, configured for transluminal delivery of the implant,
the tool including:
a shaft that extends longitudinally from a proximal part
of the tool;
a nosepiece, fixed to the shaft, and arranged with
respect to the implant such that the implant extends
proximally away from the nosepiece and over the
shaft; and
a balloon, in fluid communication with the proximal
part of the tool, and the balloon has:
a maximally-inflated state in which the balloon (i) has a
widest part that has an inflated diameter that is smaller
than the expanded diameter, and (ii) has a tapered
portion that tapers longitudinally away from the widest
part and from the nosepiece, and
a deflated state in which the widest part has a deflated
diameter that is smaller than the inflated diameter.
In an application, the nosepiece is fixed to the distal end
of the shaft.
In an application, the tapered portion tapers distally away
from the widest part and from the nosepiece.
In an application, the tapered portion tapers proximally
away from the widest part and from the nosepiece.
In an application, the balloon is slidably coupled to the
shaft at least in the deflated state of the balloon.
In an Application:
the implant (i) is constrainable, by a constraining force, in
a compressed state in which the implant has a com-
pressed diameter, and (ii) has an expanded state into
which the implant automatically transitions upon
removal of the constraining force, and in which the
implant has an expanded diameter, and
the maximally-inflated diameter of the balloon is smaller
than the expanded diameter of the implant.
In an Application:
the implant is shaped to define a lumen therethrough,
the nosepiece is arranged with respect to the implant such
that the implant extends proximally over the shaft with
the shaft within the lumen of the implant,
the implant has an expanded state, and assumes the
expanded state upon implantation of the implant, and
the nosepiece is dimensioned to be withdrawable proxi-
mally through the lumen while the implant is in its
expanded state.
In an application, the implant is self-expanding to the
expanded state.
In an application, the implant has a compressed state for
transluminal delivery, and the nosepiece is not dimensioned
to be withdrawable proximally through the lumen while the
implant is in its compressed state.
In an application, the tool further includes a sheath that is
configured to house the implant during transluminal deliv-
ery, and has a diameter that is dimensioned for transluminal
delivery.
In an application, the apparatus has a delivery state in
which the implant, the sheath, and the balloon are translu-
minally advanceable into a subject, and in which:
the implant is in a compressed state, and is housed by the
sheath, and
the balloon is in its maximally-inflated state.

In an application, the apparatus has a delivery state in
which the implant, the sheath, and the balloon are translu-
minally advanceable into a subject, and in which:
the implant is in a compressed state, and is housed by the
sheath, and
the balloon is in its deflated state.
There is further provided, in accordance with an applica-
tion of the present invention, apparatus, including:
an implant; and
a tool, configured for transluminal delivery of the implant,
the tool including:
a shaft that extends longitudinally from a proximal part
of the;
a nosepiece, fixed to the shaft, and arranged with
respect to the implant such that the implant extends
proximally away from the nosepiece and over the
shaft; and
a balloon, inflatable from a proximal part of the tool,
and coupled to the shaft such that when inflated the
balloon has a tapered portion that tapers distally
away from the nosepiece.
In an application, the nosepiece is fixed to the distal end
of the shaft.
In an Application:
the implant:
is constrainable, by a constraining force, in a com-
pressed state in which the implant has a compressed
diameter, and
has an expanded state into which the implant automati-
cally transitions upon removal of the constraining
force, and in which the implant has an expanded
diameter; and
the balloon has:
a maximally-inflated state in which (i) the balloon has
a widest part that has an inflated diameter that is
smaller than the expanded diameter of the implant,
and (ii) the tapered portion tapers distally away from
the nosepiece and from the widest part, and
a deflated state in which the widest part has a deflated
diameter that is smaller than the inflated diameter.
In an application, the balloon is slidably coupled to the
shaft at least in the deflated state of the balloon.
In an Application:
the implant is shaped to define a lumen therethrough,
the nosepiece is arranged with respect to the implant such
that the implant extends proximally over the shaft with
the shaft within the lumen of the implant,
the implant has an expanded state, and assumes the
expanded state upon implantation of the implant, and
the nosepiece is dimensioned to be withdrawable proxi-
mally through the lumen while the implant is in its
expanded state.
In an application, the implant is self-expanding to the
expanded state.
In an application, the implant has a compressed state for
transluminal delivery, and the nosepiece is not dimensioned
to be withdrawable proximally through the lumen while the
implant is in its compressed state.
In an application, the tool further includes a sheath that is
configured to house the implant during transluminal deliv-
ery, and has a diameter that is dimensioned for transluminal
delivery.
In an application, the apparatus has a delivery state in
which the implant, the sheath, and the balloon are translu-
minally advanceable into a subject, and in which:
the implant is in a compressed state, and is housed by the
sheath, and the balloon is in its maximally-inflated state.

In an application, the apparatus has a delivery state in which the implant, the sheath, and the balloon are transluminally advanceable into a subject, and in which:

the implant is in a compressed state, and is housed by the sheath, and the balloon is in its deflated state.

There is further provided, in accordance with an application of the present invention, apparatus, including:

an implant; and a tool, configured for transluminal delivery of the implant, the tool including:

a shaft that extends longitudinally from a proximal part of the tool to a distal end of the shaft, and has an opening at the distal end, the opening having an opening diameter, and the implant being reversibly coupled to the tool and disposed around the shaft; and a nosecone:

coupled to the shaft such that the nosecone has (i) a widest part that is disposed outside the opening, and has a diameter that is greater than the opening diameter, and (ii) a tapered portion that tapers distally away from the opening and the implant, and withdrawable through the opening into the shaft.

In an application, the nosecone is inflatable.

In an application, the tool further includes a sheath that is configured to house the implant during transluminal delivery, and has a diameter that is dimensioned for transluminal delivery.

There is further provided, in accordance with an application of the present invention, apparatus for use with an implant, the apparatus including a delivery tool, the delivery tool including:

a sheath that defines a cavity dimensioned to house at least a portion of the implant, and has a lip that defines a proximal opening via which the portion of the implant is removable from the cavity;

a shaft that:

extends longitudinally from a proximal part of the tool to the sheath, and is coupled to the sheath such that shaft passes through the proximal opening, and the lip circumscribes a longitudinal site of the shaft; and a balloon disposed over the shaft at at least the longitudinal site, and inflation of the balloon obstructs the opening.

In an application, the balloon is positioned and dimensioned such that inflation of the balloon brings the balloon in contact with the lip.

In an application, the sheath has a diameter, and the balloon has a maximally-inflated state in which the balloon has a widest part that has an inflated diameter that is less than the diameter of the sheath or at most 10 percent greater than the diameter of the sheath.

In an application, the balloon has a maximally-inflated state in which the balloon has a tapered portion that tapers proximally away from the opening.

In an Application:

the implant (i) is constrainable, by a constraining force, in a compressed state in which the implant has a compressed diameter, and (ii) has an expanded state into which the implant automatically transitions upon removal of the constraining force, and in which the implant has an expanded diameter, and the balloon has a maximally-inflated state in which the balloon is smaller than the expanded diameter of the implant.

In an application, the balloon has a deflated state for delivery of the implant, and a maximally-inflated state, and inflation of the balloon to the maximally-inflated state obstructs at least 80 percent of the opening.

In an application, when the balloon is in the deflated state, the opening is at least 50 percent unobstructed by either the balloon or the shaft.

In an application, the apparatus has a delivery state in which the implant, the sheath, and the balloon are transluminally advanceable into a subject, and in which:

the implant is in a compressed state, and is housed by the sheath, and the balloon is in its deflated state.

In an application, in the delivery state the implant is compressed around the balloon.

There is further provided, in accordance with an application of the present invention, apparatus, including:

an implant; and a tool, configured for transluminal delivery of the implant, the tool including:

a shaft that extends longitudinally from a proximal part of the tool, and has an open distal end, the implant being reversibly coupled to the tool and disposed around a distal portion of the shaft;

a sheath that houses the implant, and has a diameter that is dimensioned for transluminal delivery; and a control element, disposed within the shaft, movement of the control element within the shaft being controllable by the proximal part of the tool, and the control element being coupled to the sheath such that movement of the control element proximally within the shaft draws the sheath (i) distally off of the implant, and (ii) into the open distal end of the shaft.

In an application, the sheath includes a flexible sheet.

In an application, the sheet is doubled-over itself to define an inner wall of the sheath, and an outer wall of the sheath.

In an application, the sheet defines a proximal opening of the sheath at a transition zone between the inner wall and the outer wall, and the movement of the control element proximally within the shaft peels the sheath distally off of the implant by drawing the outer wall progressively into the open distal end of the shaft such that progressively proximal regions of the inner wall transition through the transition zone to become part of the outer wall, and the proximal opening of the sheath moves distally along the implant.

In an Application:

the control element includes a shank that extends through the shaft, and a coupling rotatably coupled to a distal end of the shank;

the control element is coupled to the sheath by the coupling being coupled to the sheath; and the shank defines an outer screw thread;

the shaft defines an inner screw thread that is complementary to the outer screw thread; and the control element and the shaft are configured such that rotation of the shank with respect to the sheath provides the movement of the control element proximally within the shaft by (i) screwing the shank through the shaft, but (ii) slides the coupling linearly through the shaft.

In an application, the shaft defines an inner linear groove that extends longitudinally along the shaft, and the coupling defines a fin that extends outward and into the inner groove, disposition of the fin within the groove inhibiting rotation of the coupling with respect to the shaft but allowing longitudinal sliding of the coupling through the shaft.

In an application, the inner screw thread and the inner linear groove are defined by the same longitudinal region of the shaft.

In an application, the inner screw thread and the inner linear groove transect each other.

There is further provided, in accordance with an application of the present invention, a method, for use with a subject, the method including:

transluminally advancing, into a subject, an implant housed within a cavity defined by a sheath of a tool, the tool including a balloon;

subsequently, intracorporeally removing the implant from the cavity via a proximal opening of the cavity;

subsequently, obstructing the proximal opening by inflating the balloon; and subsequently, while the balloon is inflated, withdrawing the balloon and the sheath via a lumen of the implant.

The present invention will be more fully understood from the following detailed description of applications thereof, taken together with the drawings, in which:

DETAILED DESCRIPTION OF EMBODIMENTS

Figures 1A, 1B:
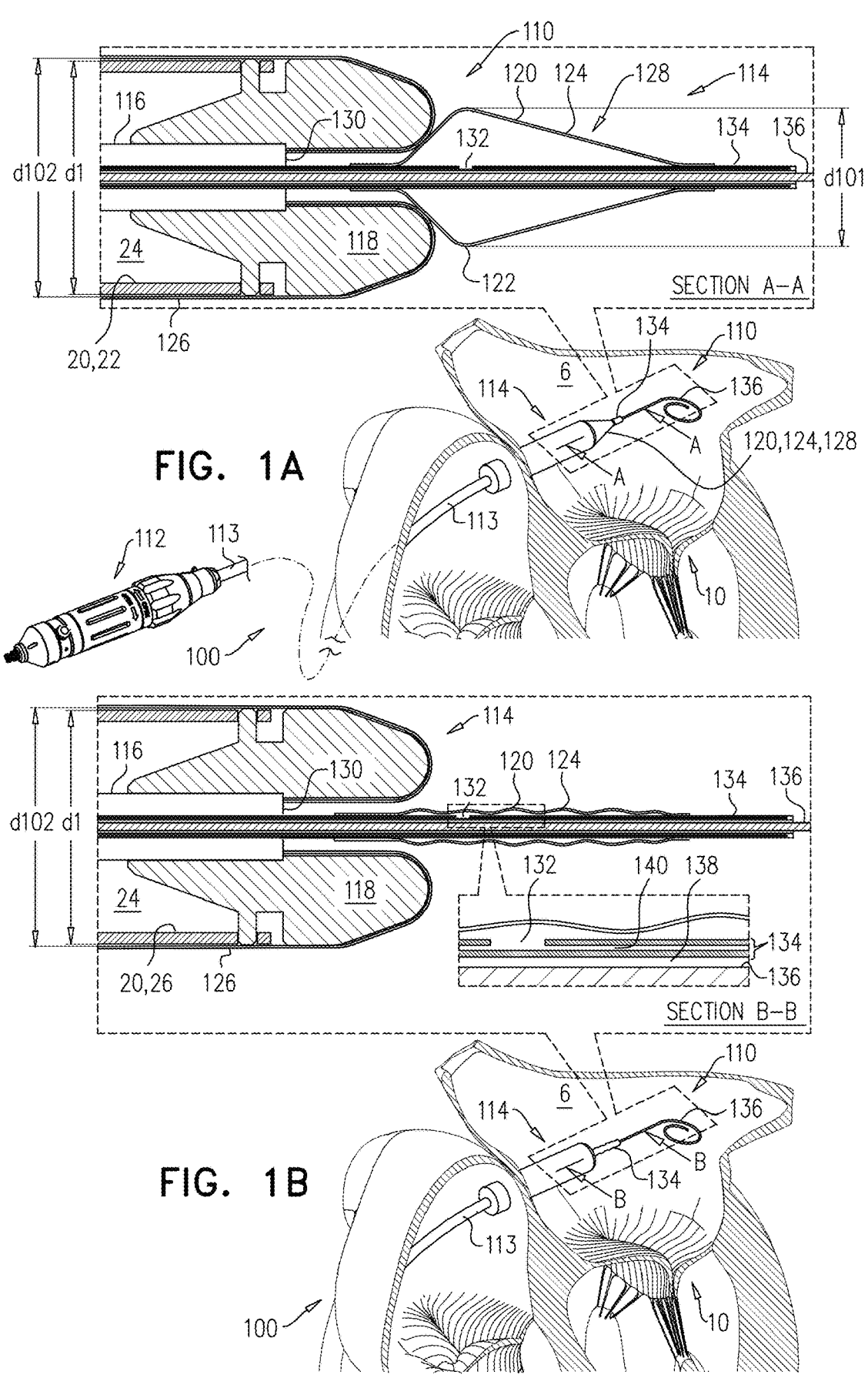
FIGS. 1A-F are schematic illustrations of a system comprising an implant and a tool configured for transluminal delivery of the implant, in accordance with some applications of the invention.

Reference is made to FIGS. 1A-F and to FIGS. 2A-F and 3, which are schematic illustrations of a system 100 and a system 200, respectively, in accordance with some applications of the invention. Each of systems 100 and 200 comprises an implant 20 and a tool 110 (system 100) or 210 (system 200), the tool configured for transluminal delivery of the implant. For some applications, and as shown, implant 20 is a prosthetic heart valve (e.g., a prosthetic mitral valve). However, implant 20 may alternatively be a different type of implant. Typically, implant 20 comprises a tubular portion 22 that defines a lumen 24 through the implant (at least in an implanted and/or expanded state of the implant). Implant 20 may further comprise additional features such as anchoring elements (not shown). For applications in which implant 20 is a prosthetic valve, the implant further comprises a valve member, such as one or more prosthetic leaflets, disposed within lumen 24.

Each of tools 110 and 210 is configured for transluminal delivery of implant 20, and has a proximal part (e.g., a proximal part 112 of tool 110; the proximal part of tool 210 may be similar, mutatis mutandis) and a distal part (tool 110) or 214 (tool 210). The proximal part is typically an extracorporeal part (e.g., comprising a handle, port(s) and/or controllers), and the distal part is transluminally advanceable into a subject (e.g., to the heart of the subject). Each of tools 110 and 210 further comprises:

(1) a shaft 116 (tool 110) or 216 (tool 210) that extends longitudinally from the proximal part of the tool to the distal part of the tool;

(2) a nosepiece 118 (tool 110) or 218 (tool 210), fixed to the shaft (e.g., to the distal end of the shaft), and arranged with respect to the implant such that the implant extends proximally away from the nosepiece and over the shaft (e.g., with the shaft disposed within a lumen defined by the implant); and (3) a balloon 120 (tool 110) or 220 (tool 210) disposed at the distal part of the tool, and in fluid communication with the proximal part of the tool (e.g., inflatable from the proximal part of the tool).

Each of balloons 120 and 220 has (i) a maximally-inflated state in which the balloon has a widest part (122 or 222, respectively) that has an inflated diameter (d101 or d201, respectively), and a tapered portion (124 or 224, respectively) that tapers longitudinally away from the widest part and from the nosepiece, and (ii) a deflated state in which the widest part has a deflated diameter that is smaller than the inflated diameter. The maximally-inflated state of balloon 120 is shown, for example, in FIG. 1A, and the maximally-inflated state of balloon 220 is shown, for example, in FIGS. 2E-F.

Balloons 120 and 220 are not configured (e.g., dimensioned or arranged with respect to implant 20) for expanding implant 20 at the implant site. Rather, the tapered portion facilities smooth intracorporeal movement of the tool. For example, and as described hereinbelow, balloon 120 facilitates movement of tool 110 distally through the vasculature of the subject, and balloon 220 facilitates withdrawal of tool 210 from implant 20.

Typically, each of tools 110 and 210 further comprises a sheath (126 or 226, respectively), configured to house the implant (e.g., at least part of the implant) during transluminal delivery, and having a diameter (d102 or d202, respectively) that is dimensioned for transluminal delivery.

Typically, implant 20 is an expandable implant, having a compressed diameter d1 (FIG. 1A) for transluminal delivery, and an expanded diameter d2 (FIG. 1E) for functioning at the implant site. Typically, the compressed and expanded diameters refer to those of tubular portion 22 (rather than those of any additional features such as an anchoring element). For example, implant 20 (e.g., tubular portion 22) may be self-expanding (e.g., comprising a shape-memory material such as Nitinol), such that it (i) is constrainable in a compressed state by a constraining force, and (ii) has an expanded state into which it automatically transitions upon removal of the constraining force. For such applications, the constraining force is typically provided by a sheath, such as sheath 126 of tool 110 or housing 426 of tool 410, and removal of the constraining force occurs when the implant becomes deployed from the sheath.

For some applications, the maximally-inflated diameter of the balloon is smaller than expanded diameter d2 of implant 20 (e.g., the expanded diameter of tubular portion 22). For example, the inflated diameter of the balloon may be less than 90 percent (e.g., less than 80 percent, e.g., less than 70 percent, e.g., less than 60 percent, e.g., less than 50 percent, e.g., less than 40 percent, e.g., less than 30 percent, e.g., less than 20 percent, e.g., less than 10 percent) of the expanded diameter of the implant It is to be noted that balloons 120 and 220 thus differ from balloons used for expanding plastically-expandable implants, inter alia, in this regard because such implant-expanding balloons necessarily expand to a diameter that is significantly greater than that of the compressed diameter of the implant, in order to expand the implant from its delivery state to its expanded state at the implantation site.

For some applications, the inflated diameter of the balloon is less than the diameter of the sheath or is at most 10 percent greater than the diameter of the sheath. For example, the inflated diameter of the balloon may be 20-110 percent, (such as 20-100 percent, or 30-110 percent) the diameter of the sheath, e.g., 30-110 percent (such as 30-100 percent or 40-110 percent), e.g., 40-110 percent (such as 40-100 percent or 50-110 percent), e.g., 50-110 percent (such as 50-100 percent or 60-110 percent), e.g., 60-110 percent (such as 60-100 percent or 70-110 percent), e.g., 70-110 percent (such as 70-100 percent or 80-110 percent), e.g., 80-110 percent (such as 80-100 percent or 90-110 percent), e.g., 90-110 percent (such as 90-100 percent or 100-110 percent). The inflated diameter of the balloon may be less than 90 percent (e.g., less than 80 percent, e.g., less than 70 percent, e.g., less than 60 percent, e.g., less than 50 percent) the diameter of the sheath. It is to be noted that balloons 120 and 220 thus differ from balloons used for expanding plastically-expandable implants, inter alia, in this regard because such implant-expanding balloons necessarily expand to a diameter that is significantly greater than that of the sheath, in order to expand the implant from its delivery state within the sheath, to its expanded state at the implantation site.

Reference is now made to FIGS. 1A-F. System 100 comprises implant 20, and tool 110. Tool 110 is configured for transluminal delivery of the implant, and comprises shaft 116, nosepiece 118, and balloon 120. In its maximally-inflated state (FIG. 1A), tapered portion 124 of balloon 120 tapers distally away from nosepiece 118 (and typically from implant 20). Balloon 120 (or tapered portion 124 thereof) therefore defines a nosecone 128 of tool 110, the nosecone facilitating transluminal advancement of the tool, such as transfemoral advancement into the aorta and/or transseptal advancement into the left atrium 6.

It is to be noted that the term "maximally-inflated state" (including in the specification and the claims) means the state in which the balloon has the inherent maximum volume provided by the dimensions into which the material from which it is made is formed (e.g., the maximum inflation before plastic deformation and/or rupture occurs).

FIG. 1A thus shows system 100 in a delivery state thereof, in which the implant, the sheath, and the balloon are transluminally advanceable into a subject. In the delivery state of system 100, (i) implant 20 is in a compressed state, and is housed by the sheath 126, and (ii) balloon 120 is in its maximally-inflated state. For some applications, diameter 101 of balloon 120 in its maximally-inflated state is 1-9 mm (e.g., 3-6 mm).

Nosecones are known in the art for advancement of devices (e.g., tools, catheters, etc.) through the vasculature. However, the presence of such nosecones adds to the length of the device. For some applications, it is important to reduce the length of the device, or particular parts thereof. For example, a delivery tool for transseptal (e.g., transfemoral) implantation of a prosthetic mitral valve (e.g., tool 110) turns sharply downward after passing through the interatrial septum 7 (e.g., at the fossa ovalis) in order (i) to pass between the leaflets of the native mitral valve 10, and (ii) to be angled (or to angle the implant therewithin) appropriately for implantation (e.g., perpendicular to the native mitral valve). The required sharpness of this turn is at least partly dictated by (i) the height d4 of atrium 6 from mitral valve 10 (e.g., the mitral annulus) to the ceiling of the atrium, (ii) the height d5 between the mitral valve and the entry point 5 of tool 110 through septum 7 (e.g., the fossa ovalis), and/or (iii) the distance across atrium 6, perpendicular to heights d4 and d5, between septum 7 and the target site-typically the center of mitral valve 10.

Because nosecone 128 is defined by balloon 120, the length of tool 110 (e.g., distal part 114 thereof) is reducible by at least deflating balloon 120. Deflation is typically performed after passage through septum 7 and before the turning of distal part 114 toward native mitral valve 10, thereby facilitating this turning.

Typically, when in its deflated state, balloon 120 is withdrawable into an opening 130 at the distal end of shaft 116, whereas inflated diameter d101 is greater than the diameter of opening 130. Therefore, nosecone 128 defined by balloon 120 is:

(1) coupled to shaft 116 such that the nosecone has (i) a widest part 122 that is disposed outside opening 130, and has a diameter d101 that is greater than the opening diameter, and (ii) a tapered portion 124 that tapers distally away from the opening and implant 20, and (2) withdrawable (e.g., slidable) through opening 130 into shaft 116.

Balloon 120 is typically fixed to a control rod 134 that is slidable within shaft 116. Control rod 134 is typically slidable over a guidewire 136 (e.g., the rod has a first lumen 138 within which the guidewire is disposed). Balloon 120 is typically also inflatable and deflatable via control rod 134, which may have a secondary lumen 140 (e.g., parallel with or coaxially surrounding the lumen 138) that has one or more openings 132 into balloon 120. Therefore, at least in its deflated state, balloon 120 is slidably coupled to shaft 116 (e.g., via rod 134).

Figure 1C:
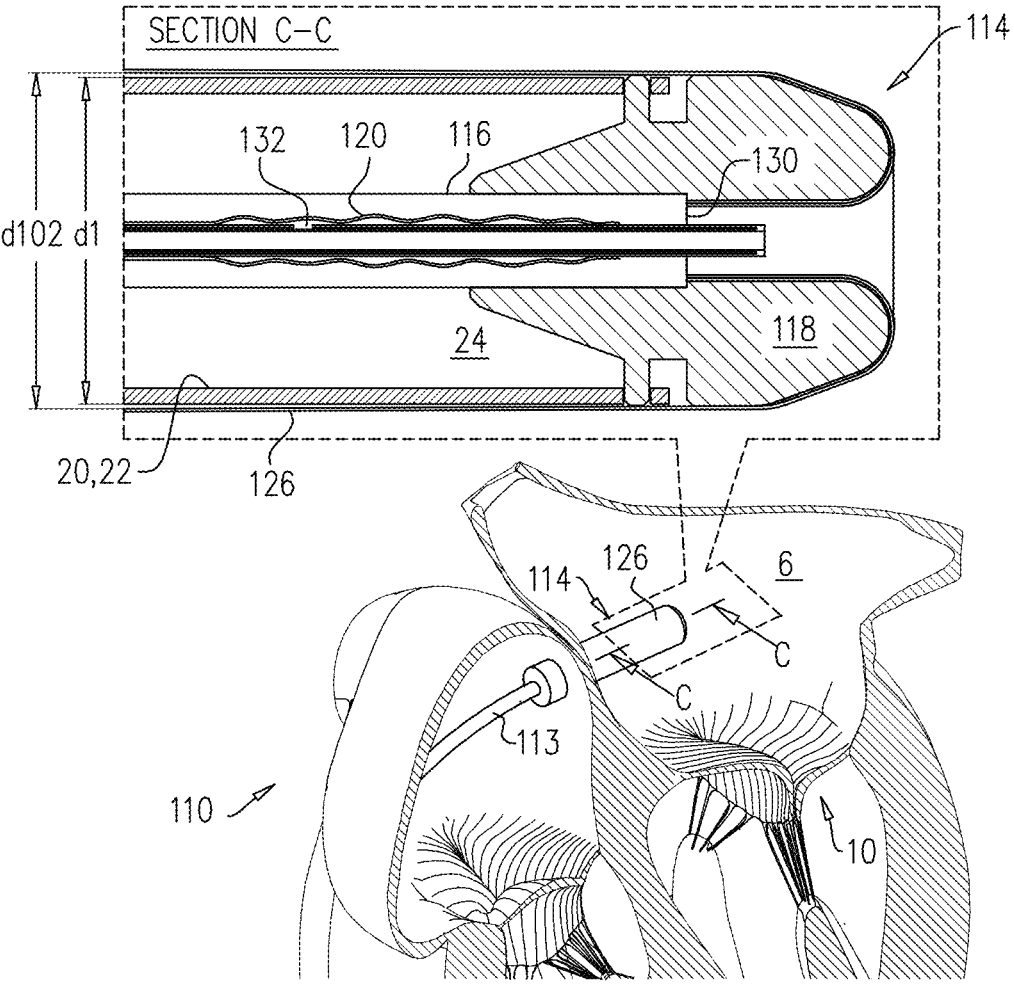
Figure 1D:
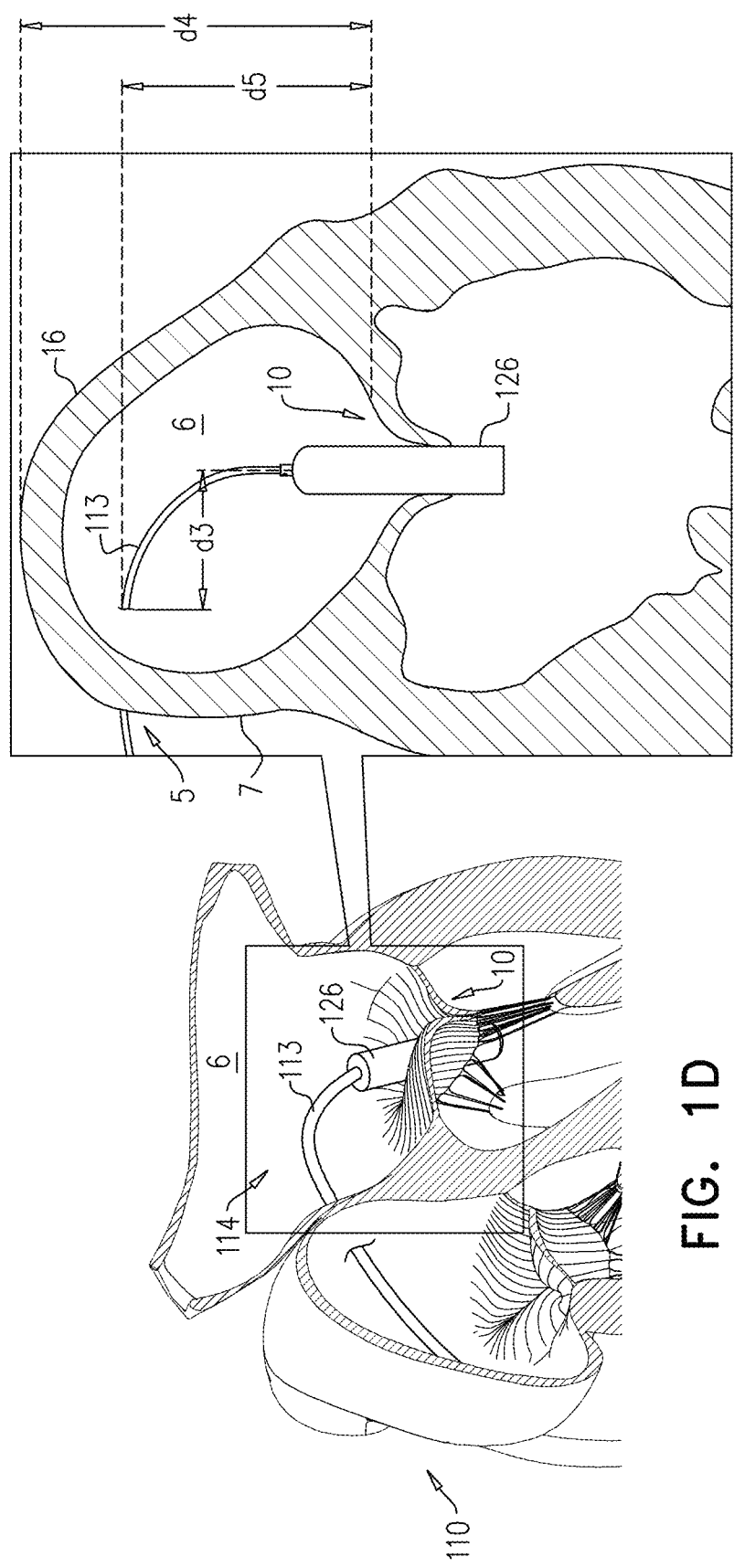

FIG. 1B shows balloon 120 in its deflated state, and FIG. 1C shows the balloon having been subsequently withdrawn into shaft 116, thereby reducing the overall length of tool 110. Subsequently, distal part 114 of tool 110 is steered toward native mitral valve 10, and between the leaflets thereof (FIG. 1D). As described hereinabove, the prior reduction in the length of tool 110 reduces a likelihood of tissue of the heart interfering with this steering. Typically, this steering is achieved using a steerable mid-portion 113 (e.g., a steerable catheter) that extends from proximal part 112 to distal part 114, and through which shaft 116 extends.

Figure 1E:
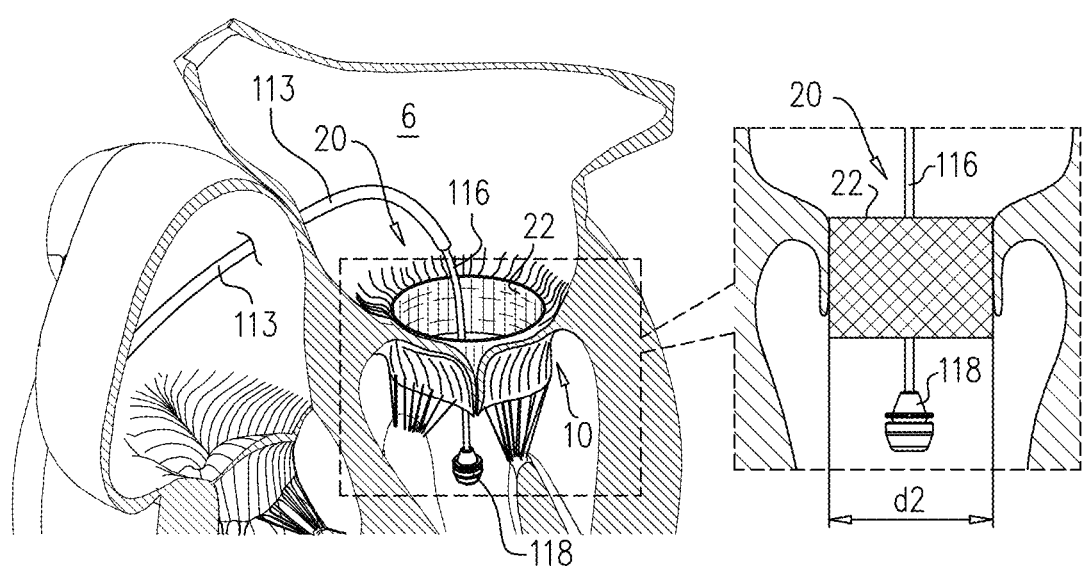
Figure 1F:
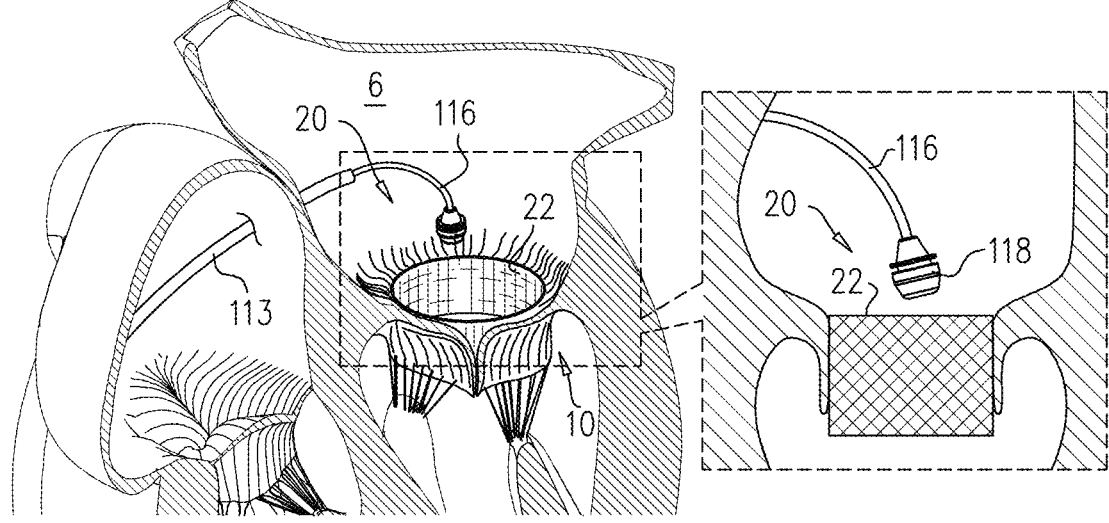

Once distal part 114 of the tool 110 is positioned at the implantation site (e.g., at native mitral valve 10), implant 20 is deployed from sheath 126. FIG. 1E shows implant 20 having expanded, upon deployment, into its expanded state. Typically, implant 20 is a self-expanding implant, e.g., comprising Nitinol or another elastic material. Typically, despite this expansion, shaft 116 remains disposed through a lumen defined by the implant until it, and nosepiece 118, are withdrawn proximally through the lumen (FIG. 1F). For some applications, nosepiece 118 is not dimensioned to be withdrawable proximally through the lumen of implant 20 while the implant is in its compressed state. For example, implant 20 may be fixed to nosepiece 118 while in its compressed state, such that the nosepiece serves as an implant controller. For example, while nosepiece 118 is in one position with respect to sheath 126 it may maintain implant 20 within the sheath, and deployment of the implant may be executed by relative movement between the nosepiece and the sheath (e.g., controlled from the proximal part of tool 110).

Sheath 126 is not shown in FIGS. 1E-F, reflecting that, for some embodiments, sheath 126 is a flexible sheath that is drawn into shaft 116 during deployment of implant 20 (e.g., as described for sheath 326 with reference to FIGS. 4A-D, mutatis mutandis). However, it is to be noted that for some applications, sheath 126 is rigid (e.g., is a capsule) and is withdrawn while remaining disposed over part of shaft 116. (For such applications, sheath 126 would be visible in FIGS. 1E-F.)

There is therefore provided, a method, comprising: (1) transluminally advancing, into a subject, an implant housed within a cavity defined by a sheath of a tool, the tool including a balloon; (2) subsequently, intracorporeally removing the implant from the cavity via a proximal opening of the cavity; (3) subsequently, obstructing the proximal opening by inflating the balloon; and (4) subsequently, while the balloon is inflated, withdrawing the balloon and the sheath via a lumen of the implant.

Reference is now made to FIGS. 2A-F, and 3. System 200 comprises implant 20, and tool 210. Tool 210 is configured for transluminal delivery of the implant, and comprises shaft 216, nosepiece 218, and balloon 220. As described in more detail hereinbelow, in its maximally-inflated state (FIGS. 2E-F), tapered portion 224 of balloon 220 tapers proximally away from nosepiece 218.

Figures 2A, 2B, 2C:
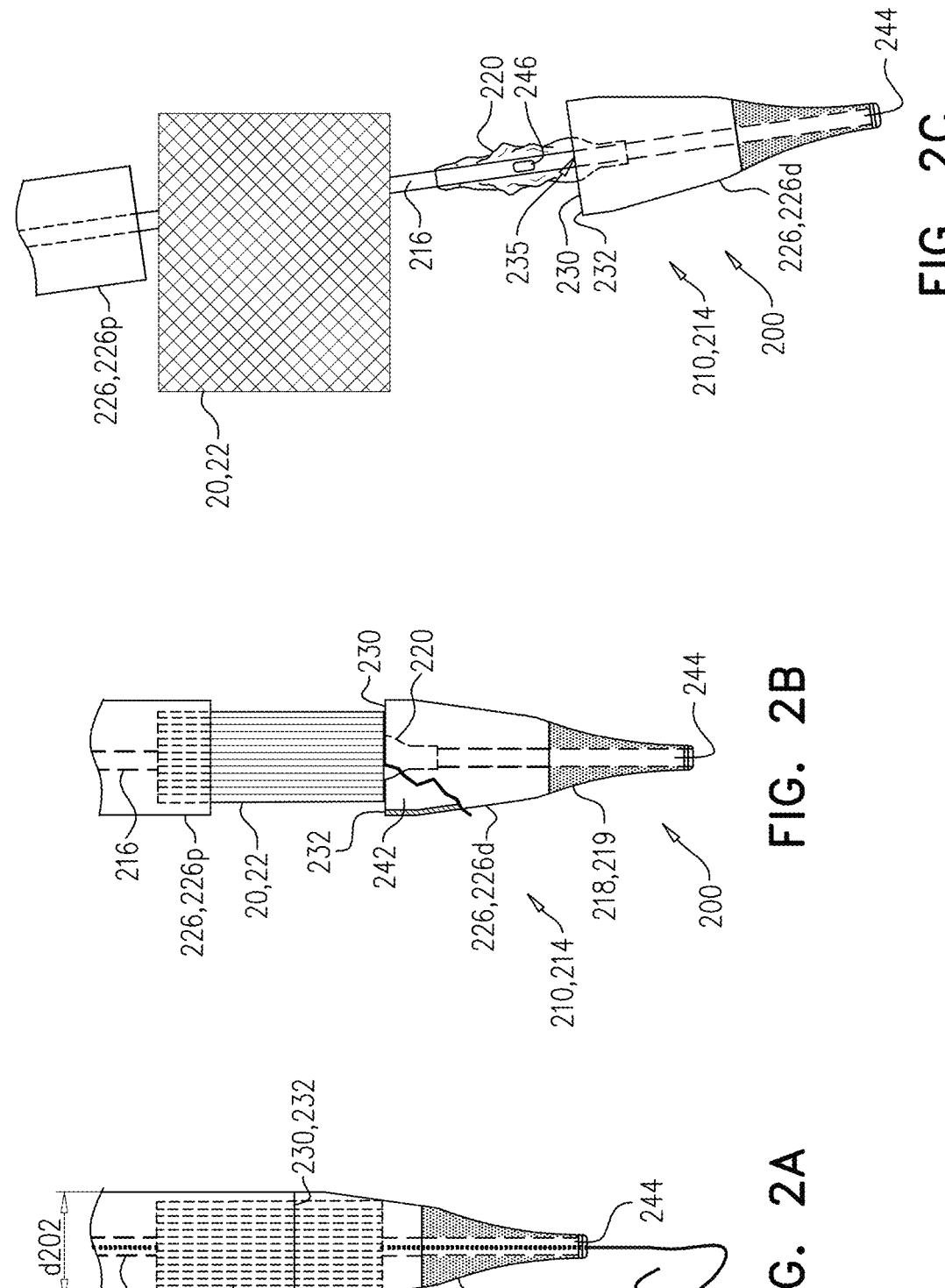
FIGS. 2A-F and 3 are schematic illustrations of another system comprising the implant and a tool configured for transluminal delivery of the implant, in accordance with some applications of the invention.

FIG. 2A shows system 200 in a delivery state thereof, in which implant 20, sheath 226, and balloon 220 are transluminally advanceable into a subject, toward a delivery site (e.g., mitral valve 10). In the delivery state of system 200, (i) implant 20 is in a compressed state, and is housed by the sheath 226 (which typically constrains the implant in the compressed state), and (ii) balloon 220 is in its deflated state.

Sheath 226 defines a cavity 242 that is dimensioned to house at least a portion of implant 20, and has a lip 232 that defines a proximal opening 230 via which the housed portion of the implant is removable from the cavity. For some applications, sheath 226 comprises a distal piece 226d and a proximal piece 226p that face each other and house respective portions of implant 20, and the distal piece defines cavity 242 and proximal opening 230. (Sheath 226 may alternatively comprise only one piece, shaped generally like distal piece 226d.)

Shaft 216 extends longitudinally from the proximal part of the tool to distal part 214, at which sheath 226 and nosepiece 218 are disposed. Shaft 216 is coupled to the sheath such that shaft passes through proximal opening 230, and lip 232 circumscribes a longitudinal site 235 of the shaft. Typically, balloon 220 is disposed over the shaft at at least longitudinal site 235.

Shaft 216 extends through the lumen defined by implant 20, and is fixed to nosepiece 218, which is disposed distally to the implant. Typically, nosepiece 218 is fixed to sheath 226 (e.g., distal piece 226d thereof). For some applications, and as shown, sheath 226 (e.g., distal piece 226d thereof) is fixed to shaft 216 via nosepiece 218 (i.e., by being connected to the nosepiece, which itself is connected to the sheath). Typically, nosepiece 218 is fixed to the distal end of shaft 216. Nosepiece 218 serves as a nosecone 219; the advantages of a nosecone are described hereinabove. Typically, nosepiece 218 is not dimensioned to be withdrawable proximally through the lumen of implant 20 while the implant is in its compressed state.

Tool 210 is typically advanced to the implantation site over a guidewire 236. For example, shaft 216, sheath 226, and/or nosepiece 218 are shaped to define a lumen 244 through which guidewire 236 is slidable.

Once at the implantation site, the housed portion of implant 20 is removed from cavity 242 by moving distal piece 226d distally with respect to the implant (FIG. 2B). In addition, proximal piece 226p may be moved proximally with respect to the implant. Implant 20 is deployed by sufficiently (e.g., fully) exposing it from sheath 226. For applications in which implant 20 is self-expanding, the implant expands automatically after the constraining force provided by sheath 226 has been removed by sufficiently exposing the implant from the sheath.

FIG. 2C shows system 200 after implant 20 has been deployed from sheath 226. Nosepiece 218, distal piece 226d of sheath 226, and at least most (e.g., all) of balloon 220 are disposed distally to implant 20. For delivery tools that house an implant in a sheath that has a proximal opening (e.g., a two-piece sheath such as sheath 226, or a sheath that has only one piece shaped generally like distal piece 226d), withdrawal of the sheath after implantation of the implant is typically performed by withdrawing the sheath through the lumen of the implant. For example, in the case of a prosthetic valve, the sheath is typically withdrawn through the prosthetic valve, passing between its prosthetic leaflets. A risk exists that, should the distal part of the implantation tool be imperfectly aligned with the implanted implant, the lip (that defines the proximal opening through which the implant was previously withdrawn) may engage (e.g., catch onto) the implant, making withdrawal difficult and/or dislodging the implant. Balloon 220 reduces this risk.

Either before (as shown) or after implantation of implant 20, guidewire 236 is removed from lumen 244. For some applications, lumen 244 is in fluid communication with balloon 220, and the balloon is inflated via this lumen. For some such applications, this fluid communication is provided by a port 246 defined by shaft 216, and balloon 220 is inflated by delivering a fluid 238 (e.g., saline) via shaft 216, e.g., via the lumen 244 in which guidewire 236 was previously disposed. Because lumen 244 is open at a distal end, in order to provide fluid pressure for inflating balloon 220, a control rod 248 that is slidable within shaft 216 is slid into lumen 244 prior to inflation. Control rod 248 comprises a distal plug 250 that fits snugly within at least a distal region 244d of lumen 244 (distal to port 246), such that when the plug is introduced, it seals against the walls of lumen 244 (or at least distal region 244d thereof). For example, plug 250 may have an outer diameter that is at least 50 (e.g., at least 70, e.g., at least 90, such as at least 95) percent of the inner diameter of lumen 244. For some applications, and as shown, distal region 248d is defined by nosepiece 218 (e.g., nosecone 219). For some applications, and as shown, plug 250 defines an external screw thread 254, and is screwed into distal region 248d. For example, nosepiece 218 may comprise a flexible material such as silicone into which screw thread 254 may cut. (Alternatively, distal region 248d may be lined with such a material.) The flexible material may advantageously increase atraumatic properties of nosecone 219.

Figures 2D, 2E, 2F:
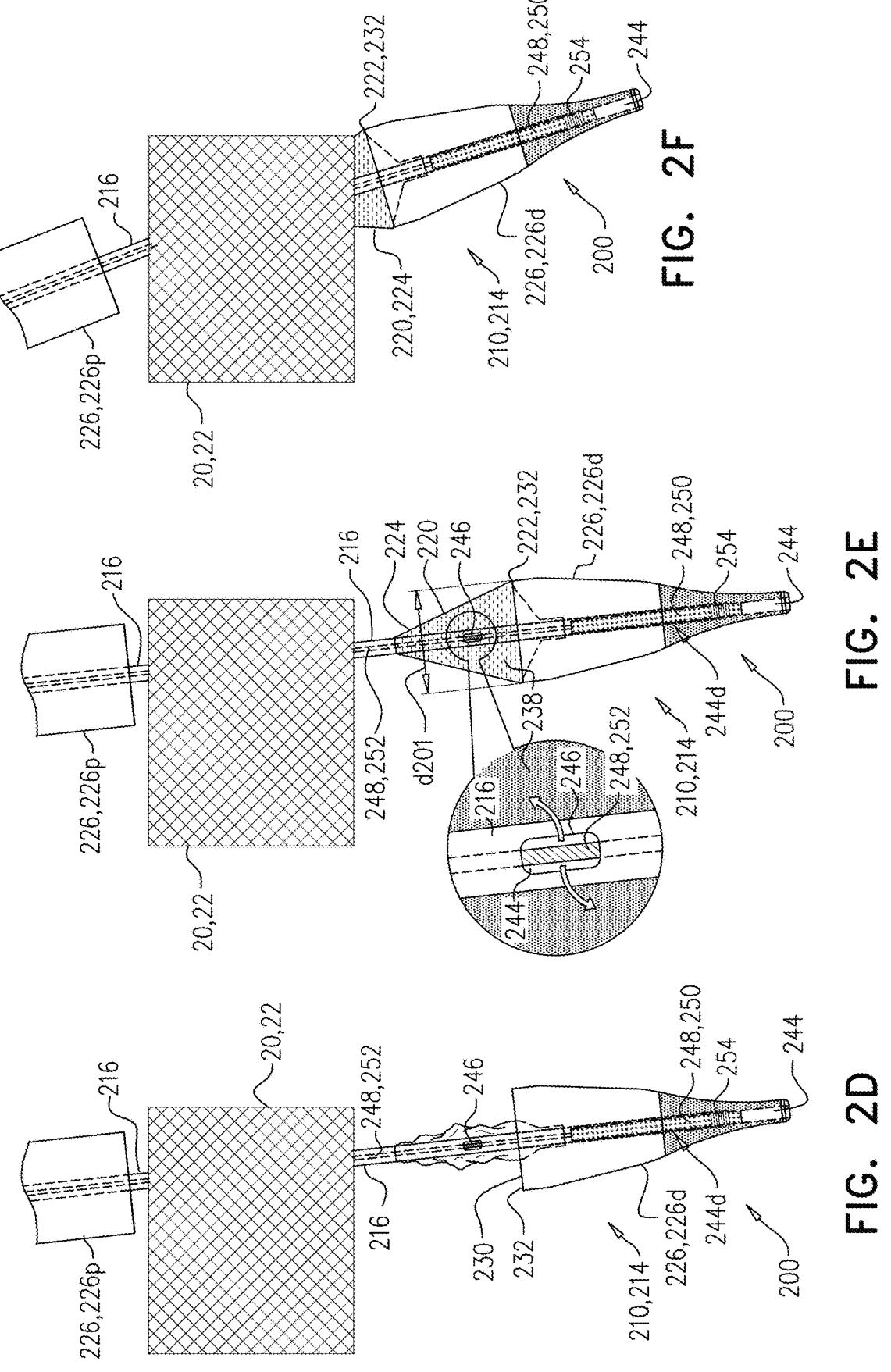

Control rod 248 further comprises a flexible proximal portion 252, which has a diameter that is less than 90 percent (e.g., 20-60 percent) of the inner diameter of lumen 244. Control rod 248 is dimensioned such that, while distal plug 250 is disposed at distal region 248d of lumen 244, proximal portion 252 extends distally through lumen 244 at least until port 246. Fluid introduced into lumen 244 at the proximal part of tool 210 flows along the lumen, alongside portion 252, and out of port 246, thereby inflating balloon 220 (FIG. 2E). Plug 250 inhibits the fluid from escaping at distal part 214 of tool 210.

It is to be noted that the scope of the invention includes other techniques for inflating balloon 220. For example, for some applications, shaft 216 may have a secondary lumen that opens into balloon 220, e.g., as described for lumen 140 of control rod 134 of system 100, mutatis mutandis.

FIG. 2E shows balloon 220 in its maximally-inflated state. Inflation of balloon 220 obstructs opening 230. For some applications, and as shown, inflation of balloon 220 obstructs at least 80 percent (e.g., at least 90 percent) of opening 230, e.g., obstructs opening 230 completely (e.g., scaling up the opening). For example, widest part 222 may have an inflated diameter that is equal to, or slightly (e.g., 1-10 percent) greater than the diameter of opening 230, and balloon 220 comes into contact with (e.g., seals against) lip 232 when inflated. For some applications, inflation of the balloon obstructs 80-90 percent or 90-99 percent of opening 230. In contrast, in the deflated state of balloon 220, opening 230 is typically at least 50 percent (e.g., 60-90 percent) unobstructed by the balloon and/or shaft 216. The obstruction of opening 230 caused by inflation of balloon 220 reduces the risk of lip 232 engaging implant 20 during withdrawal. Because this functionality is provided by a balloon, when the balloon is deflated, cavity 242 is available to house at least part of implant 20.

Figure 3:
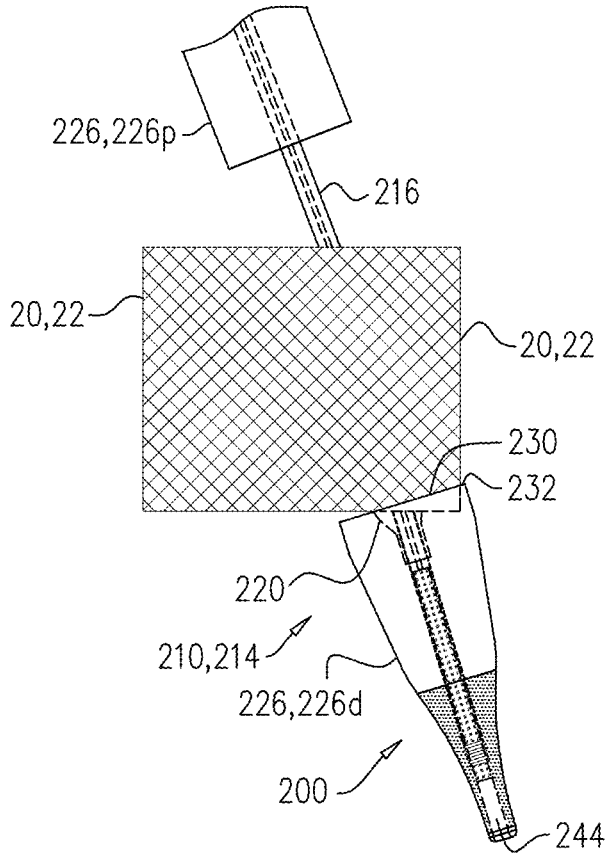

FIG. 2F shows distal part 214 of tool 210 being withdrawn via the lumen of implant 20, while balloon 220 (e.g., tapered portion 224 thereof) slides past parts of the implant that lip 232 may otherwise have engaged. FIG. 3 illustrates what may occur during withdrawal if balloon 220 is not inflated (or what may occur in a similar system that does not comprise balloon 220), and therefore demonstrates an advantage of system 200. In FIG. 3, lip 232 engages part of implant 20 (e.g., part of the implant enters cavity 242 via opening 230), impeding withdrawal of distal piece 226*d* and/or causing dislodgement of implant 20.

Reference is made to FIGS. 4A-D, which are schematic illustrations of a system 300, which comprises implant 20, and a tool 310 configured for transluminal delivery of the implant. Tool 310 comprises a shaft 316 that extends longitudinally from a proximal part 312 of the tool (which typically comprises a handle and/or controller), and has an open distal end 330. Implant 20 is reversibly coupled to the tool, and is disposed around a distal portion of shaft 316. Tool 310 comprises a sheath 326 that houses implant 20, and has a diameter that is dimensioned for transluminal delivery. Tool 310 further comprises a control element 334, disposed within shaft 316. Movement of control element 334 within shaft 316 is controllable by proximal part 312 of tool 310, and control element 334 is coupled to sheath 326 such that movement of the control element proximally within the shaft draws the sheath (i) distally off of implant 20, and (ii) into open distal end 330 of the shaft.

Typically, sheath 326 comprises a flexible sheet 328, such as a sheet or fabric of a polymer (e.g., nylon, polytetrafluoroethylene, polyester, or polyethylene terephthalate). For some applications, sheet 328 defines sheath 326 as a single-walled sheath, and as it is drawn distally off of implant 20, it slides directly over implant 20 (e.g., is in contact with the implant).

Figures 4A, 4B:
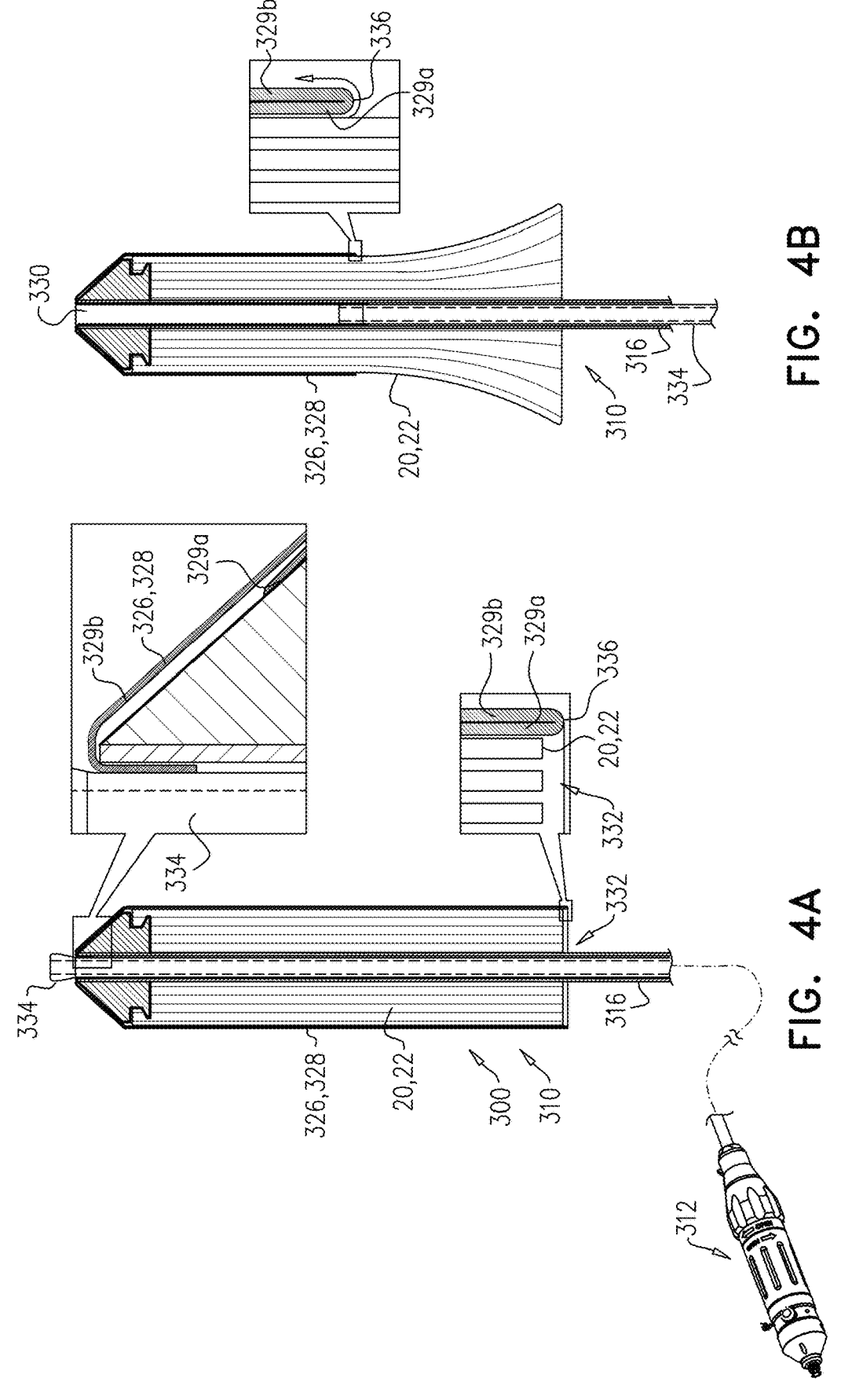
FIGS. 4A-D are schematic illustrations of another system comprising the implant and a tool configured for transluminal delivery of the implant, in accordance with some applications of the invention.

For some applications, and as shown, sheet 328 is doubled-over itself to define an inner wall 329*a* of sheath 326 (i.e., defines the sheath as a double-walled sheath), and an outer wall 329*b* of the sheath (FIG. 4A). For such applications, a proximal opening 332 of sheath 326 is defined at a transition zone 336 between inner wall 329*a* and outer wall 329*b* (i.e., the zone at which sheet 328 transitions between defining the inner wall and defining the outer wall). That is, the transition zone defines a lip of the sheath, the lip defining proximal opening 332. The above-described movement of control element 334 proximally within shaft 316 draws (e.g., peels) sheath 326 distally off of implant 20 by drawing outer wall 329*b* progressively into open distal end 330 of the shaft such that progressively proximal regions of inner wall 329*a* transition through transition zone 336 to become part of the outer wall, and the transition zone (and thereby proximal opening 332 of the sheath) moves distally along the implant, exposing progressively distal regions of the implant (FIGS. 4B-C).

Inner wall 329*a* is typically in contact with implant 20 (e.g., constraining the implant to its compressed diameter), but outer wall 329*b* is not in contact with the implant. During the unsheathing of implant 20, neither inner wall 329*a* nor outer wall 329*b* slides directly over the implant while in contact with the implant. Rather, outer wall 329*b* slides over inner wall 329*a* (e.g., while in contact with the inner wall), and the sheath effectively peels off of the implant, thereby advantageously reducing friction that might be caused by direct sliding of the sheath over the implant while in contact with the implant.

Figures 4C, 4D:
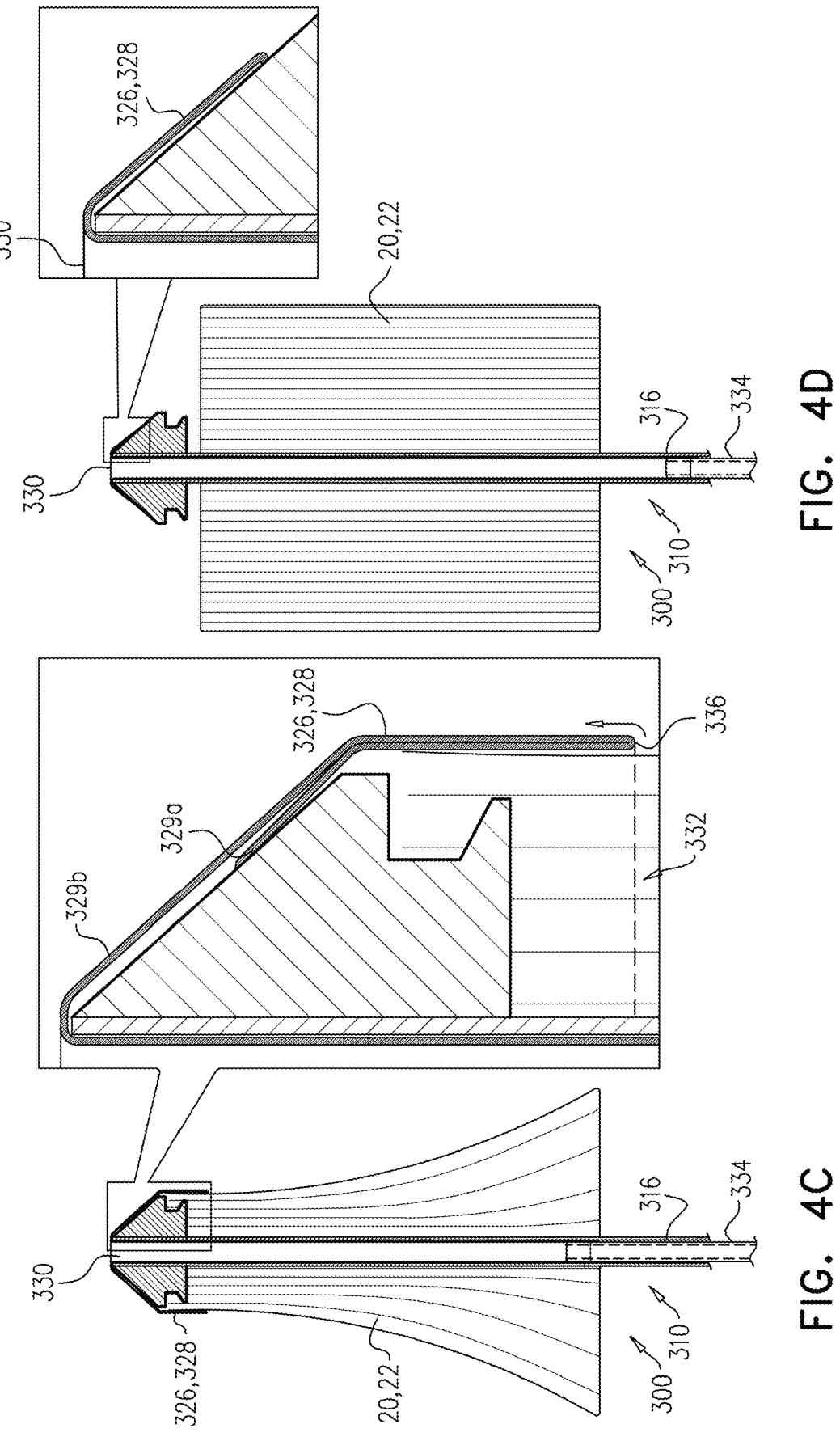

FIG. 4D shows sheath 326 having been completely drawn off of implant 20, and the implant having responsively expanded.

Figure 5:
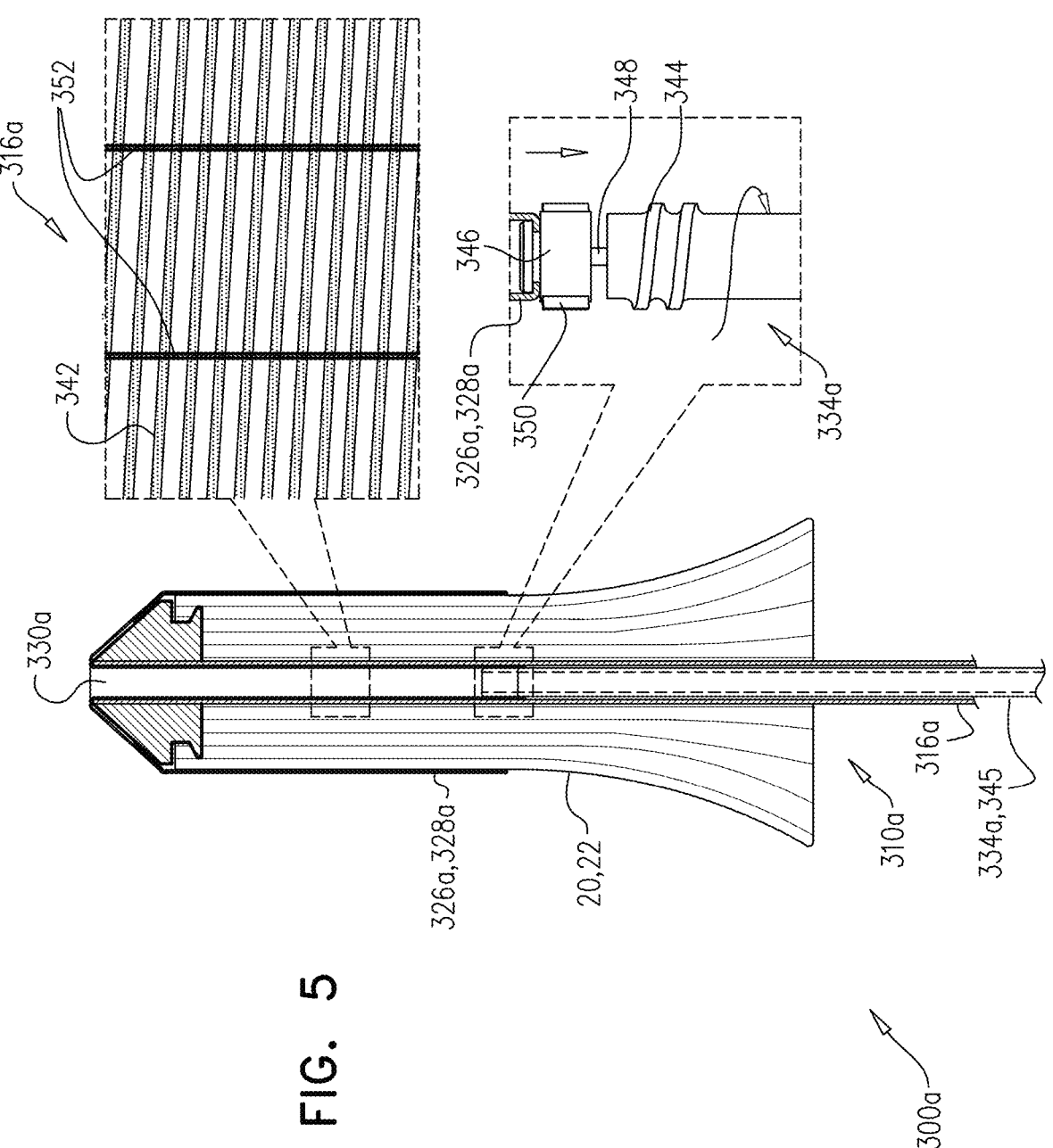
FIG. 5 is a schematic illustration of another system comprising the implant and a tool configured for transluminal delivery of the implant, in accordance with some applications of the invention.

Reference is now made to FIG. 5, which is a schematic illustration of a system 300*a*, which is an embodiment of system 300, in accordance with some applications of the invention. Elements in FIG. 5 that have a reference numeral suffixed "a" are equivalent, mutatis mutandis, to elements in FIGS. 4A-D that have the same reference numeral (without the suffix), except where noted. FIG. 5 shows the state of system 300*a* that is equivalent to the state of system 300 shown in FIG. 4B, mutatis mutandis.

As described for system 300, movement of control element 334*a* within shaft 316*a* is controllable by a proximal part of tool 310*a*, and control element 334*a* is coupled to sheath 326*a* such that movement of the control element proximally within the shaft draws the sheath (i) distally off of implant 20, and (ii) into open distal end 330*a* of the shaft. In system 300*a*, this movement of control element 334*a* is achieved by rotating the control element within shaft 316*a*. Shaft 316*a* and control element 334*a* define, respectively, complementary inner screw thread 342 and outer screw thread 344. FIG. 5 includes an enlarged inset view that shows shaft 316*a* as though it were opened up flat. Control element 334*a* comprises a shank 345, and a coupling 346, typically at a distal end of the control element, that is rotatably coupled to shank 345 (e.g., via a bearing 348). Coupling 346 is the portion of control element 334*a* that is coupled to sheath 326*a*. Due to mating of threads 342 and 344, rotation of shank 345 within shaft 316*a* causes control element 334*a* as a whole to move proximally within the shaft, while coupling 346 remains relatively rotationally stationary with respect to the shaft (e.g., coupling 346 slides longitudinally without rotating), thereby causing sheath 326*a* to be drawn (i) distally off of implant 20, and (ii) into open distal end 330*a* of the shaft, without the rotation of shank 345 twisting the sheath. That is, rotation of shank 345 within shaft 316*a* causes (i) screwing of the shank through the shaft, but (ii) sliding (e.g., linear sliding) of coupling 346 through the shaft.

For some applications, coupling 346 rotates slightly with respect to shaft 316*a*, but remains relatively rotationally stationary with respect to the shaft due to resistance provided by sheath 326*a*. For some applications, coupling 346 defines one or more fins 350 that each protrudes radially outward, and into a respective longitudinal groove 352 defined by shaft 316*a*. Fins 350 can slide only linearly along grooves 352, thereby inhibiting rotation of coupling 346 with respect to shaft 316*a*, but allowing the coupling to slide longitudinally along the shaft. For some applications, and as shown, grooves 352 and thread 342 may be defined on the same longitudinal region of shaft 316*a*, and may in fact transect each other.

Reference is made to FIGS. 6A-C and 7A-C, which are schematic illustrations of a tool 410, for use with an implant such as implant 20, in accordance with some applications of the invention. Typically, tool 410 is a delivery tool for transluminal delivery of implant 20. A system 400 may be provided, comprising implant 20 and tool 410.

Tool 410 comprises a housing (e.g., a sheath) 426 at a distal part 414 of the tool. Housing 426 comprises a tubular wall 428 that circumscribes a longitudinal axis ax1 of the distal part of tool 410. Housing 426 is dimensioned to house at least part of implant 20. Housing 426 (e.g., wall 428 thereof) defines a track 430 that follows a generally-helical path around longitudinal axis ax1. Tool 410 further comprises a controller 440 that comprises a rod 442 and an actuator 444. Rod 442 extends from a proximal part of the tool to housing 426. Actuator 444 is rotatable with respect to housing 426, and is typically fixedly coupled to rod 442. Actuator 444 comprises an engaging element 446 that engages track 430. Controller 440 and housing 426 mechanically cooperate such that rotation of actuator 444 with respect to the housing (e.g., by rotation of rod 442) slides the housing longitudinally with respect to the actuator.

Typically, this movement is bidirectional. That is, rotation of actuator 444 in a first direction with respect to housing 426 slides the housing proximally with respect to the actuator, and rotation of the actuator in a second, opposite direction with respect to the housing slides the housing distally with respect to the actuator.

Typically, and as shown, housing 426 is dimensioned to house implant 20 such that track 430 is disposed around at least the part of implant 420. That is, typically, at least part of implant 20 is coincident, along axis ax1, with at least part of track 430.

For some applications, housing 426 defines more than one track 430, rotationally-offset from each other e.g., in order to evenly distribute forces applied by actuator 444 (which for such applications typically comprises a corresponding more than one engaging element 446). For example, and as shown, housing 426 may define two tracks 430*a* and 430*b*, rotationally-offset by 180 degrees from each other, and actuator 444 may comprise a corresponding two engaging elements 446, also rotationally-offset by 180 degrees from each other. For the sake of clarity, reference numerals 430*a* and 430*b* are only used in FIG. 6A.

Figure 7A:
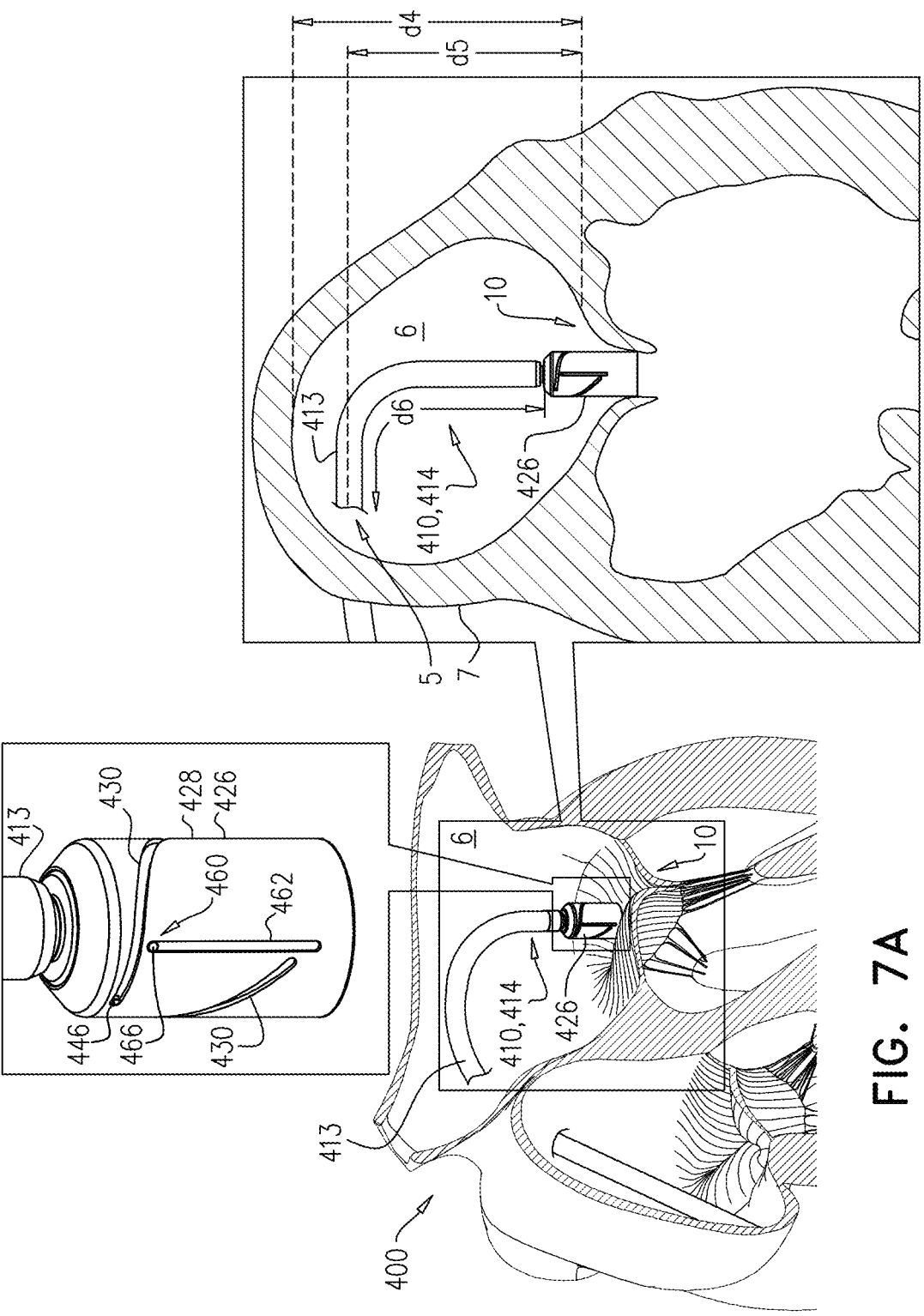
Figure 7B:
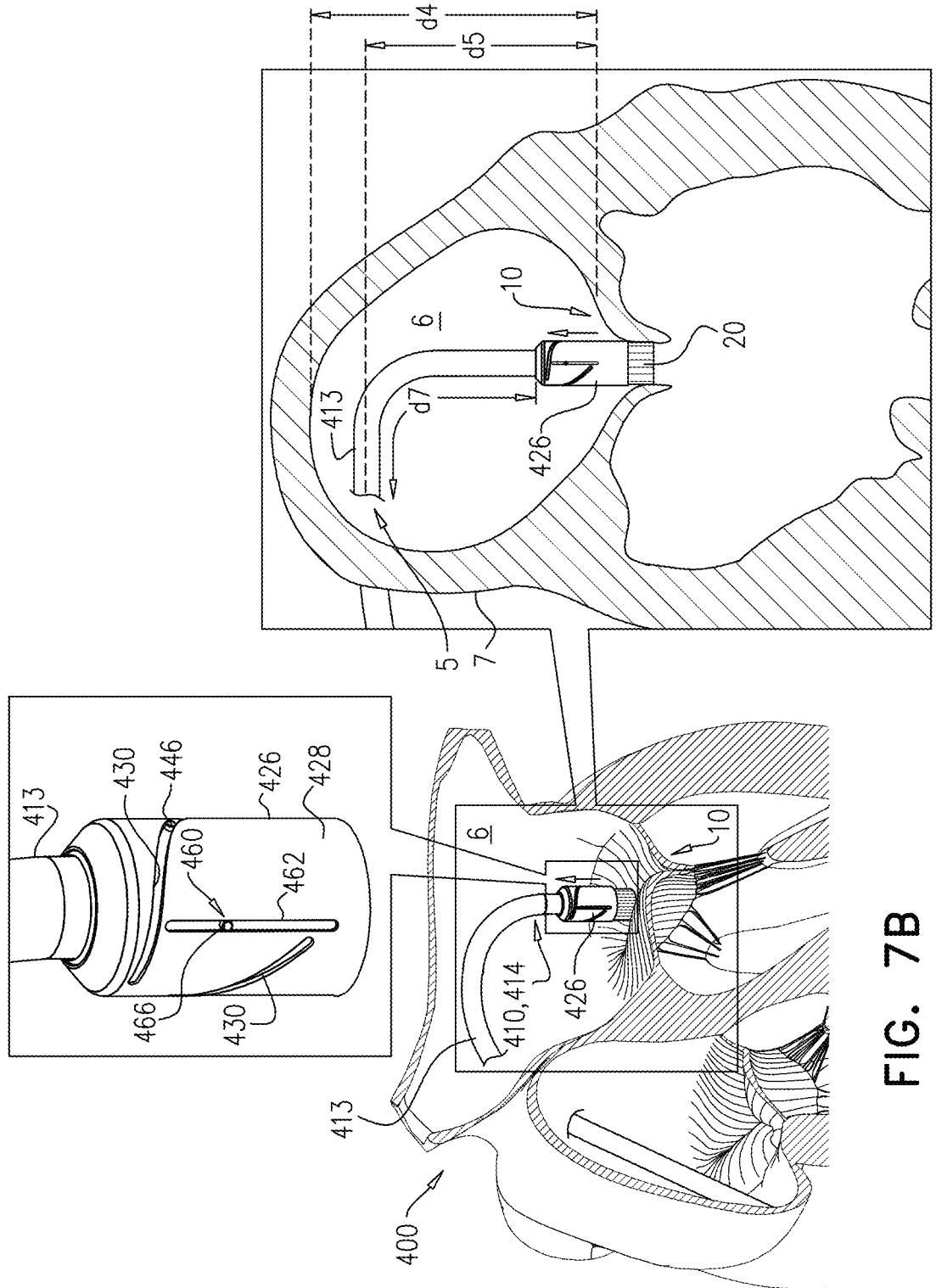
Figure 7C:
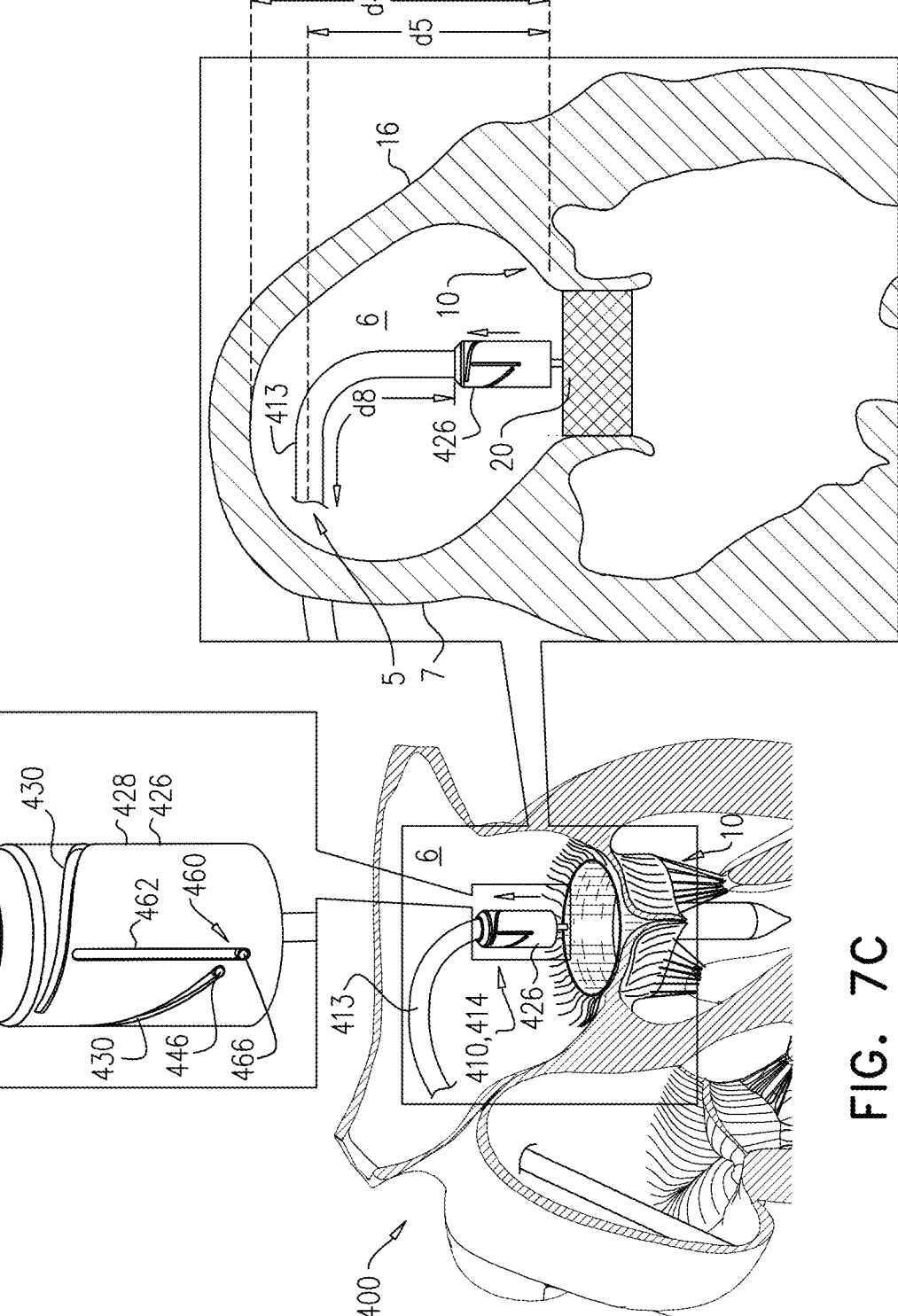

Typically, tool 410 further comprises a catheter 413 (e.g., a mid-portion of the tool), longitudinally disposed between the proximal part of the tool, such as a control handle, and distal part 414. Housing 426 is typically disposed distally to catheter 413. Rod 442 extends through catheter 413, and typically into housing 426. The mechanical cooperation between controller 440 and housing 426 is such that, to retract the housing from implant 20 (i.e., to deploy the part of the implant housed by the housing) rotation of actuator 444 with respect to the housing slides the housing proximally along and over part of the catheter. This is illustrated in FIGS. 7A-C, which show progressive steps in the retraction of housing 426 to deploy implant 20. Distances d6, d7, and d8 are each measured along catheter 413, between a given point on the catheter (e.g., a point of entry into atrium 6) and housing 426. Distance d7 is smaller than distance d6, and distance d8 is smaller than distance d7.

As described hereinabove, the dimensions of left atrium 6 limit maneuverability when implanting an implant at mitral valve 10 transseptally (e.g., transfemorally). For example, the height d4 of atrium 6, and/or the height d5 between the mitral valve and the entry point 5 of a delivery tool through septum 7 (e.g., the fossa ovalis), limit the distance to which the delivery tool can be raised away from the mitral valve in order to withdraw the housing or sheath of the tool from over the implant in order to deploy the implant. In particular, these heights limit the ability to raise the tool away from the mitral valve without moving and/or angling the tool toward entry point 5, and thereby tilting the implant with respect to the mitral valve. It is hypothesized by the inventors that tool 410 facilitates deployment of an implant at the mitral valve, and/or deployment without tilting the implant, because the retraction of housing 426 over catheter 413 replaces at least some of the otherwise required withdrawal of the delivery tool as a whole. For some applications, and as shown in FIGS. 7A-C, once catheter 413 and the implant within are in the correct position (FIG. 7A) deployment of the implant is possible without further movement of catheter 413 (FIGS. 7B-C).

Tool 410 typically further comprises a shaft 450 to which implant 20 is fixable, the shaft being slidably coupled housing 426, and extending proximally from the housing. Shaft 450 thereby serves as a mount for implant 20, and facilitates movement of other parts of tool 410 (e.g., housing 426) with respect to the implant.

Typically, tool 410 is configured in a manner that inhibits housing 426 from rotating in response to rotation of actuator 444, because the differential rotation causes the retraction of the housing. Therefore, tool 410 therefore typically comprises a housing-rotation inhibitor 460. For some applications, and as shown, housing-rotation inhibitor 460 comprises (i) a second track 462 that follows a generally-linear path parallel to longitudinal axis ax1, and (ii) a second engaging element 466. Engaging element 466 is fixedly coupled to shaft 450 (e.g., via a mount 464), and engages track 462, thereby rotationally fixing the shaft with respect to housing 426, while facilitating longitudinal sliding of the shaft with respect to the housing. Therefore, controller 440 and housing 426 mechanically cooperate such that rotation of actuator 444 with respect to the housing slides the track 462 longitudinally with respect to engaging element 466.

For some applications, housing 426 defines more than one second track 462, rotationally-offset from each other, e.g., in order to evenly distribute forces applied to it by, for example, a corresponding more than one engaging element 466. For example, and as shown, housing 426 may define two tracks 462, rotationally-offset by 180 degrees from each other, and tool 410 may comprise a corresponding two engaging elements 466, also rotationally-offset by 180 degrees from each other.

Typically, rod 442 is coaxial with shaft 450. Further typically, shaft 450 is disposed within rod 442 (which is typically disposed within catheter 413). Typically, actuator 444 defines a hole therethrough, through which shaft 450 extends. For example, at least part of shaft 450 may be disposed within housing 426, and the shaft extends distally out of catheter 413, through the hole in actuator 444, and into the housing.

The term "generally helical" is used with respect to the path of track 430 because the path may not be a true helix. For example, for some applications, and as shown, the pitch of the generally-helical path of the track differs along its length. For some such applications, a first portion 432p of the generally-helical path has a first pitch, and a second portion 432d of the generally-helical path, which is distal to the first portion, has a second pitch that is greater than the first pitch. For example, the pitch of the generally-helical path may gradually increase, such that it is progressively greater at progressively distal portions of the generally-helical path. It is hypothesized by the inventors that this facilitates (i) application of greater linear force during the initial stage of deployment from housing 426, while more of implant 20 is disposed in the housing and friction between the implant and housing is greater, and (ii) greater linear movement during later stages of deployment from housing 426, after some of the implant has already exited the housing, and friction between the implant and housing has been reduced. Alternatively or additionally, the distance of track 430 from longitudinal axis ax1 may differ along its length. For example, housing 426 may be wider toward its distal opening, and track 430, defined by the housing, may correspondingly become increasingly further from axis ax1 toward the distal opening of the housing.

Figure 6A:
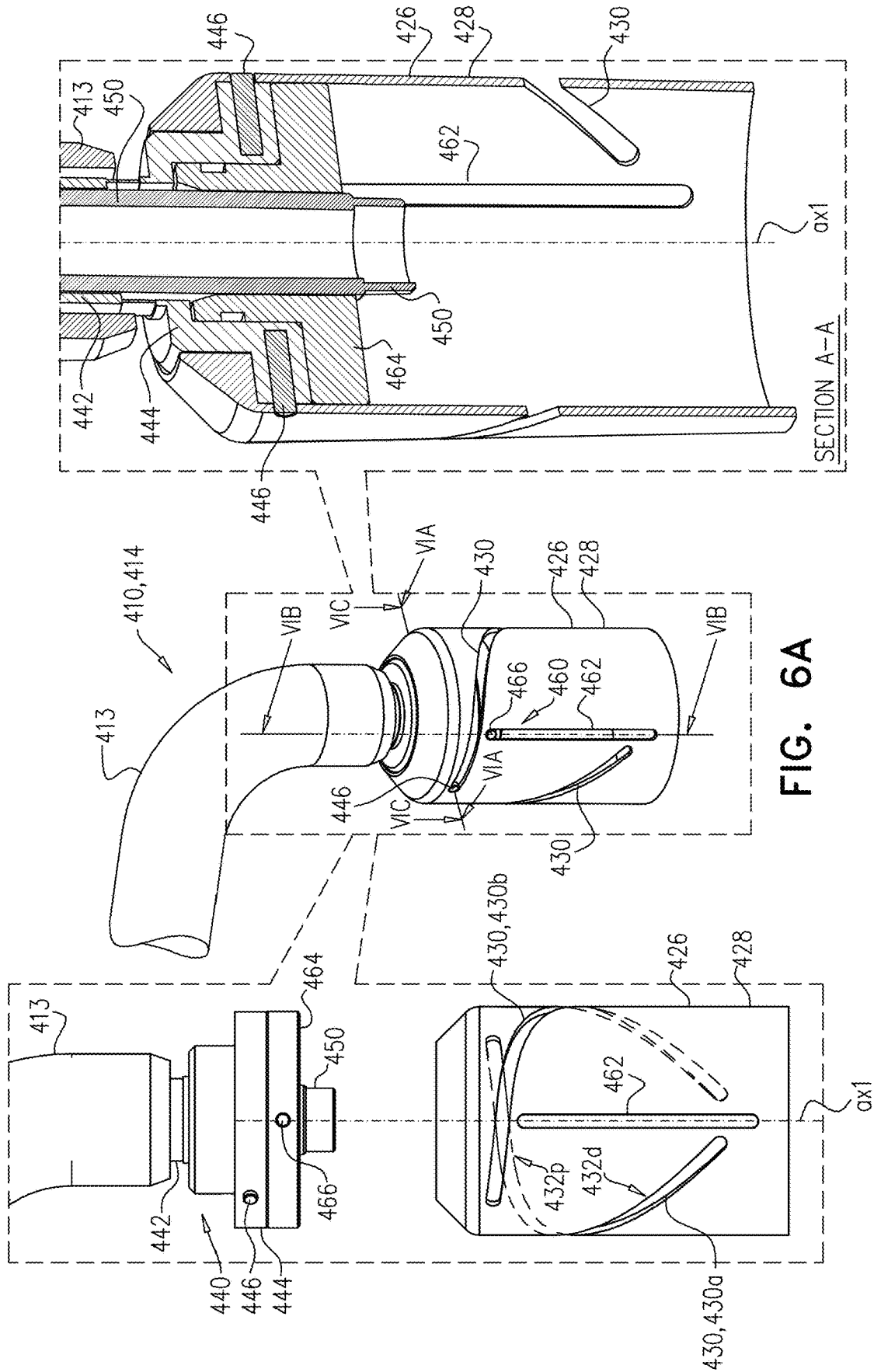
FIGS. 6A-C and 7A-C are schematic illustrations of a tool for use with an implant, in accordance with some applications of the invention.
Figure 6C:
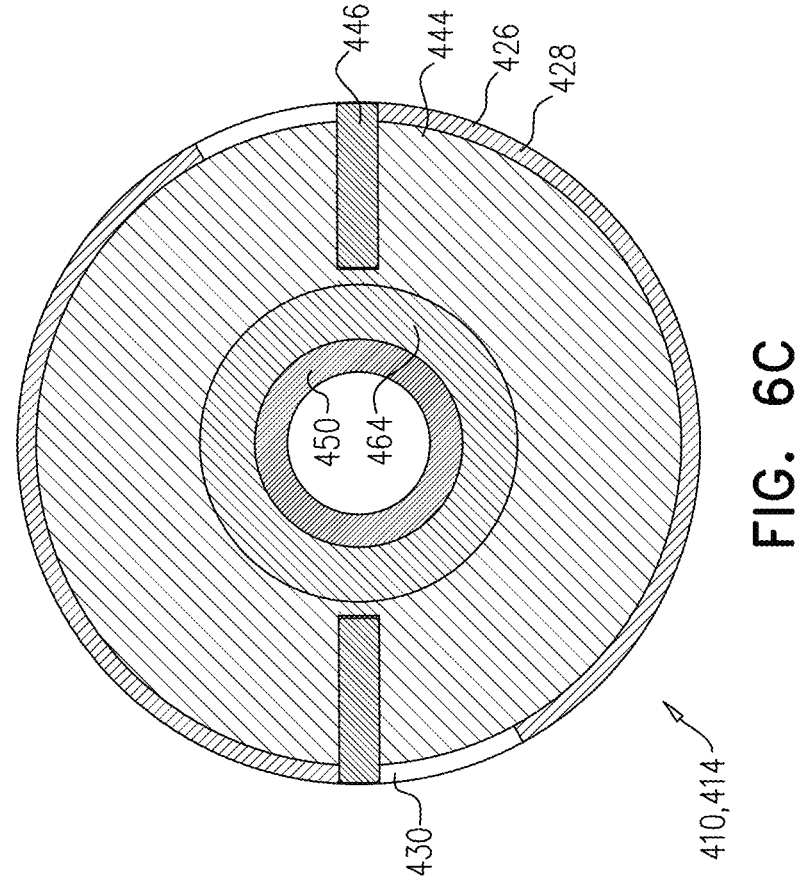
Figure 6B:
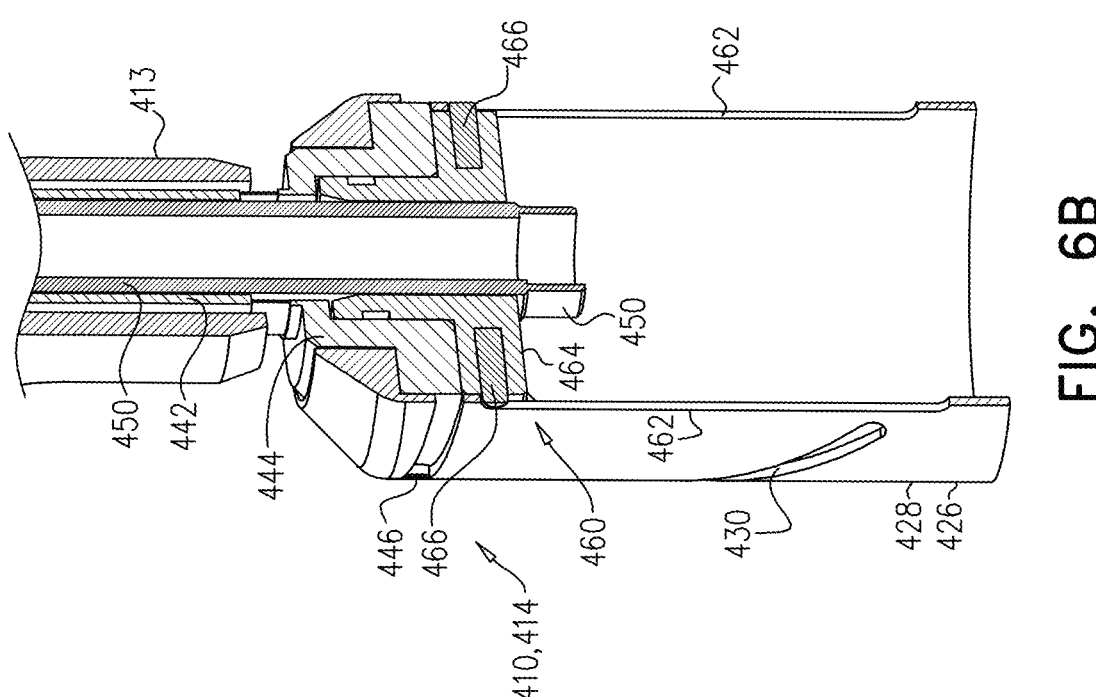
Figure 8:
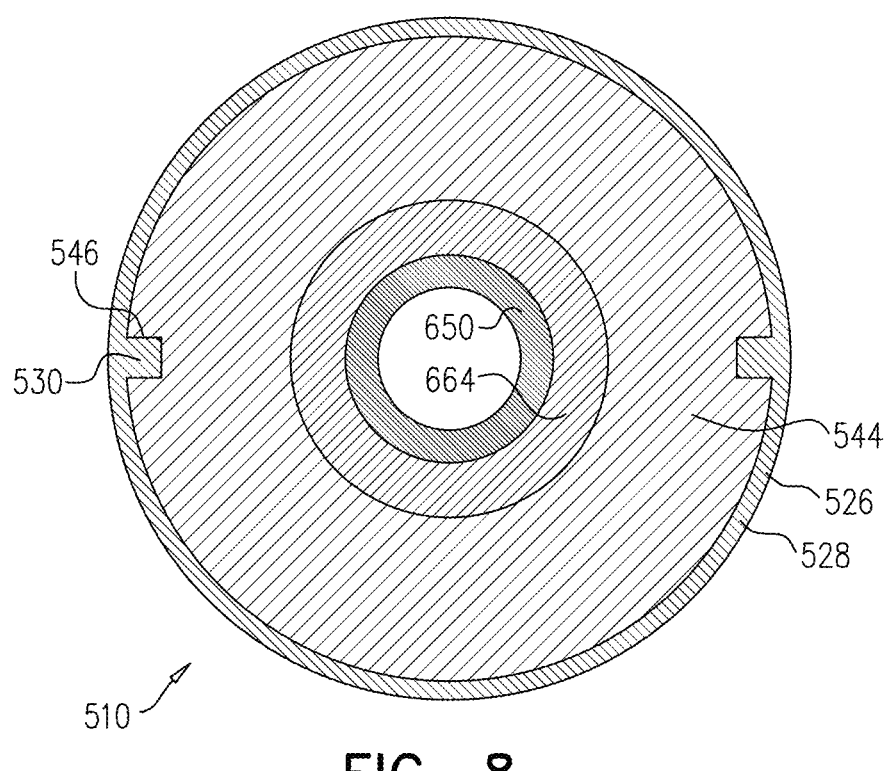
FIG. 8 is a schematic illustration of an alternative tool, in accordance with some applications of the invention.

Typically, and as shown, track 432 is a channel (e.g., cut into housing 426, such as into tubular wall 428 thereof), and engaging element 446 is a spur that engages the track by protruding into the channel. However, alternative tracks and engaging elements may be used. For example, and as shown in FIG. 8, to which reference is now additionally made, the track may be a rail, and the engaging element may be a notch that engages the track by receiving the rail. FIG. 8 is a schematic illustration of alternative tool 510, in accordance with some applications of the invention. Except where noted, tool 510 is identical to tool 410, and its components are identical to identically-named components of tool 410. FIG. 8 shows a transverse cross-section of tool 510 that substantially corresponds to the transverse cross-section of tool 410 that is shown in FIG. 6C. As shown, a track 530 (which substantially corresponds to track 430 of tool 410) is a rail that protrudes radially-inward from a tubular wall 528 of a housing 526, and an engaging element 546 is a notch defined by an actuator 544, the notch receiving the rail.

Second track 462 and second engaging element 466 are shown as a channel and spur, but may, alternatively or additionally, be similarly substituted with a rail and notch, mutatis mutandis. For example, tool 510 may comprise a shaft 550 to which is fixedly coupled an engaging element (not shown in FIG. 8), e.g., via a mount 564.

For some applications, the first track and the first engaging element are of the channel-and-spur type, and the second track and the second engaging element are of the rail-and-notch type. For some applications, the first track and the first engaging element are of the rail-and-notch type, and the second track and the second engaging element are of the channel-and-spur type. For some applications, both are of the channel-and-spur type (e.g., as shown for tool 410). For some applications, both are of the rail-and-notch type.

Reference is again made to FIGS. 1A-8. The components of the systems described herein may be combined in various ways. For example, balloon 120 may be used (in addition to or in place of the above-described components) in system 200 and/or in system 300, mutatis mutandis; balloon 220 may be used (in addition to or in place of the above-described components) in system 100 and/or in system 300, mutatis mutandis; and/or sheath 326 may be used (in addition to or in place of the above-described components) in system 100 or in system 200, mutatis mutandis.

Similarly, tool 410, or elements thereof, may be used in combination with other embodiments described herein. For example, housing 426 may serve as a proximal piece of a sheath (e.g., sheath 226) that also has a distal piece, housing 426 being moved proximally to deploy a proximal part of the housed implant, and the distal piece of the sheath being moved distally to deploy a distal part of the housed implant. That is, for some applications, housing 426 is a proximal housing that is dimensioned to house a first part of the implant, and has a distal opening for deployment of the first part of the implant therethrough; and the tool further comprises a distal housing that is dimensioned to house a second part of the implant, and has a proximal opening, facing the distal opening, for deployment of the second part of the implant therethrough. For such applications, both housings are typically independently slidable with respect to the implant, and also with respect to shaft 450.

The term "diameter," which is used throughout this application (including the specification and the claims), refers to a dimension of the component that is transverse to the longitudinal axis of the component and/or of the system as a whole. The term "diameter" is used because such components typically have a circular transverse cross-section. However, it is to be understood that the descriptions may equally apply to equivalent components that have a non-circular cross-section, mutatis mutandis.

Each of the systems described hereinabove is described as comprising implant 20. However, it is to be noted that the scope of the invention includes systems that do not comprise an implant—i.e., systems that are otherwise the same as those described, but which are provided as delivery systems for an implant that is not included.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   transluminally delivering an implant to a heart of a patient, using a delivery tool,
   (1) the implant:
      comprising (i) a frame that defines a central longitudinal lumen, and (ii) prosthetic valve leaflets disposed within the lumen,
      constrainable, by a constraining force, in a compressed state in which the lumen has a compressed internal diameter, and
      having an expanded state into which the implant automatically transitions upon removal of the constraining force, and in which the lumen has an expanded internal diameter,
   (2) the delivery tool comprising:
      a shaft that extends longitudinally from a proximal part of the delivery tool;
      a nosepiece fixed to the shaft, and arranged with respect to the implant such that the implant extends proximally away from the nosepiece and over the shaft; and an expandable element, which is coupled to the shaft proximally to the nosepiece and which has:

a maximally-expanded state in which the expandable element (i) has a widest part that has an expanded external diameter that is smaller than the expanded internal diameter of the lumen of the frame, and (ii) has a tapered portion that tapers proximally away from the widest part and from the nosepiece, and a non-expanded state in which the widest part has a non-expanded external diameter that is smaller than the expanded external diameter of the expandable element, and (3) wherein during the transluminal delivering, the implant and the delivery tool have a delivery state in which:

the implant is in the compressed state, the expandable element is in the non-expanded state, and a portion of the expandable element is disposed within the lumen of the frame;

implanting the implant in a native valve of the heart of the patient; and following the implanting, while the implant is in its expanded state, withdrawing the expandable element proximally through the lumen of the frame, between the prosthetic valve leaflets, and out of the lumen.

2. The method according to claim 1, wherein the nosepiece is fixed to a distal end of the shaft.

3. The method according to claim 1, wherein:

the delivery tool further comprises a sheath, and transluminally delivering the implant to the heart comprises transluminally delivering the sheath while the sheath houses the implant.

4. The method according to claim 1, wherein the method does not include withdrawing the nosepiece proximally through the lumen while the implant is in its compressed state.

5. The method according to claim 1, wherein transluminally delivering the implant using the delivery tool comprises delivering the implant while a proximal end of the nosepiece is distal to a distal end of the implant.

6. The method according to claim 1, wherein transluminally delivering the implant using the delivery tool comprises delivering the implant while a proximal end of the nosepiece is distal to a distal end of the expandable element.

7. The method according to claim 1, wherein the delivery tool further comprises a distal sheath which is fixed to a proximal end of the nosepiece, and wherein transluminally delivering the implant using the delivery tool comprises delivering the distal sheath while the distal sheath houses a distal portion of the implant.

8. The method according to claim 7, wherein transluminally delivering the implant using the delivery tool comprises delivering the distal sheath while the distal sheath houses a distal portion of the expandable element.

9. A method, comprising:

transluminally delivering an implant to a heart of a patient, using a delivery tool, (1) the implant:

comprising (i) a frame that defines a central longitudinal lumen, and (ii) prosthetic valve leaflets disposed within the lumen, constrainable, by a constraining force, in a compressed state in which the lumen has a compressed internal diameter, and having an expanded state into which the implant automatically transitions upon removal of the constraining force, and in which the lumen has an expanded internal diameter, (2) the delivery tool comprising:

a shaft that extends longitudinally from a proximal part of the delivery tool;

a nosepiece fixed to the shaft, and arranged with respect to the implant such that the implant extends proximally away from the nosepiece and over the shaft; and an expandable element, which is coupled to the shaft proximally to the nosepiece and which has:

a maximally-expanded state in which the expandable element (i) has a widest part that has an expanded external diameter that is less than 90 percent of the expanded internal diameter of the lumen of the frame, and (ii) has a tapered portion that tapers proximally away from the widest part and from the nosepiece, and a non-expanded state in which the widest part has a non-expanded external diameter that is smaller than the expanded external diameter of the expandable element, and (3) wherein during the transluminal delivering, the implant and the delivery tool have a delivery state in which:

the implant is in the compressed state, the expandable element is in the non-expanded state, and a portion of the expandable element is disposed within the lumen; and implanting the implant in a native valve of the heart of the patient.

10. The method according to claim 9, wherein the nosepiece is fixed to a distal end of the shaft.

11. The method according to claim 9, wherein:

the delivery tool further comprises a sheath, and transluminally delivering the implant to the heart comprises transluminally delivering the sheath while the sheath houses the implant.

12. The method according to claim 9, wherein transluminally delivering the implant using the delivery tool comprises delivering the implant while a proximal end of the nosepiece is distal to a distal end of the implant.

13. The method according to claim 9, wherein transluminally delivering the implant using the delivery tool comprises delivering the implant while a proximal end of the nosepiece is distal to a distal end of the expandable element.

14. The method according to claim 9, wherein:

transluminally delivering the implant using the delivery tool comprises delivering the nosepiece arranged with respect to the implant such that the implant extends proximally over the shaft with the shaft within the lumen of the frame, the implant assumes the expanded state upon implantation of the implant, and the method further comprises withdrawing the nosepiece proximally through the lumen while the implant is in its expanded state.

15. The method according to claim 14, wherein the method does not include withdrawing the nosepiece proximally through the lumen while the implant is in its compressed state.

16. The method according to claim 9, wherein the delivery tool further comprises a distal sheath which is fixed to a proximal end of the nosepiece, and wherein transluminally delivering the implant using the delivery tool comprises delivering the distal sheath while the distal sheath houses a distal portion of the implant.

17. The method according to claim 16, wherein transluminally delivering the implant using the delivery tool comprises delivering the distal sheath while the distal sheath houses a distal portion of the expandable element.

\* \* \* \* \*